(12) United States Patent
Araki et al.

(10) Patent No.: US 7,115,690 B2
(45) Date of Patent: Oct. 3, 2006

(54) FLUORINE-CONTAINING POLYMER, RESIST COMPOSITION PREPARED FROM SAME AND NOVEL FLUORINE-CONTAINING MONOMER

(75) Inventors: Takayuki Araki, Settsu (JP); Takuji Ishikawa, Settsu (JP); Meiten Koh, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 126 days.

(21) Appl. No.: 10/815,801

(22) Filed: Apr. 2, 2004

(65) Prior Publication Data

US 2004/0191680 A1    Sep. 30, 2004

Related U.S. Application Data

(63) Continuation-in-part of application No. PCT/JP02/10242, filed on Oct. 2, 2002.

(30) Foreign Application Priority Data

Oct. 3, 2001 (JP) ............................. 2001-307823
Feb. 28, 2002 (JP) ............................. 2002-054964

(51) Int. Cl.
*C08F 12/20* (2006.01)
(52) U.S. Cl. ...................... 526/242; 526/250; 526/309; 430/905
(58) Field of Classification Search ..................... None
See application file for complete search history.

(56) References Cited

FOREIGN PATENT DOCUMENTS

JP      10-231329 A      9/1998
JP      2001-356480 A    12/2001

OTHER PUBLICATIONS

English translation of JP 10-231329.*
International Search Report for PCT/JP02/10242 dated Jan. 21, 2003.

* cited by examiner

*Primary Examiner*—Rosemary Ashton
(74) *Attorney, Agent, or Firm*—Sughrue Mion, PLLC

(57) ABSTRACT

There is provided a fluorine-containing copolymer having an aliphatic monocyclic structure in the polymer trunk chain which has a number average molecular weight of from 500 to 1,000,000 and is represented by the formula (Ma):

$$-(M1)-(M2a)-(N)- \quad \text{(Ma)}$$

in which
the structural unit M1 is a structural unit derived from an ethylenic monomer having 2 or 3 carbon atoms and at least one fluorine atom, the structural unit M2a is at least one structural unit which introduces an aliphatic monocyclic structure in the polymer trunk chain and is represented by the formula (a):

$$-(R^3)_{n1}-CH\underset{R^1}{\overset{(R^2)_{n2}}{\diagup\diagdown}}CH-(R^4)_{n3}- \quad \text{(a)}$$

wherein $R^1$ is at least one hydrocarbon group selected from the group consisting of a divalent hydrocarbon group having 1 to 8 carbon atoms and constituting a ring which may be further substituted with a hydrocarbon group or a fluorine-containing alkyl group and a divalent hydrocarbon group having ether bond which has the sum of carbon atoms and oxygen atoms of 2 to 8, constitutes a ring and may be further substituted with a hydrocarbon group or a fluorine-containing alkyl group; $R^2$ is an alkylene group which has 1 to 3 carbon atoms and constitutes a ring; $R^3$ and $R^4$ are the same or different and each is a divalent alkylene group which has 1 or 2 carbon atoms and constitutes a ring; n1, n2 and n3 are the same or different and each is 0 or 1, the structural unit N is a structural unit derived from a monomer copolymerizable with the monomers to introduce the structural units M1 and M2a, and
the structural units M1, M2a and N are contained in amounts of from 1 to 99% by mole, from 1 to 99% by mole and from 0 to 98% by mole, respectively. The fluorine-containing polymer possesses excellent dry etching resistance and transparency in a vacuum ultraviolet region.

9 Claims, 1 Drawing Sheet

… (1)

FLUORINE-CONTAINING POLYMER, RESIST COMPOSITION PREPARED FROM SAME AND NOVEL FLUORINE-CONTAINING MONOMER

CROSS-REFERENCE TO RELATED APPLICATION

This is a continuation-in-part of PCT international application No. PCT/JP02/10242 filed on Oct. 2, 2002, incorporated herein by reference.

BACKGROUND OF THE INVENTION

The present invention relates to a novel fluorine-containing unsaturated cyclic compound, a novel fluorine-containing polymer having an aliphatic monocyclic structure in its trunk chain, and a chemically amplifying photoresist composition which is obtained from the fluorine-containing polymer, is excellent in transparency and possesses improved dry etching resistance.

As a result of an increasing necessity for high integration of a large scale integrated circuit (LSI), microfabrication technology is required for photolithography. In order to satisfy such requirements, there have been tried to use, as exposure light sources, a deep ultraviolet, a KrF excimer laser beam (wavelength: 248 nm) and a ArF excimer laser beam (wavelength: 193 nm) which have a wavelength shorter than conventional g-rays (wavelength: 436 nm) and i-rays (wavelength: 365 nm). Those light sources are put into practical use.

Recently a process using a $F_2$ laser beam (wavelength: 157 nm) having a wavelength in a vacuum ultraviolet region has been studied in an ultra-microfabrication technology and is considered promising as an exposure technology aiming at a technology node of 0.1 µm.

On the other hand, in the pattern formation, a chemically amplifying resist which becomes advantageous in transparency, resolution, sensitivity and dry etching resistance in cases of energy rays having various wavelengths has been studied. The chemically amplifying resist means, for example, in case of a positive resist, an energy-sensitive composition comprising a resin being soluble in an alkali developing solution and having an introduced substituent which has an effect of inhibiting dissolution of the resin but is deprotected due to action of an acid, and a compound which generates an acid by irradiation of energy rays such as light and electron beam (hereinafter referred to as a photoacid generator). When the composition is irradiated with light or electron beam, an acid is generated from the photoacid generator, and by heating (post-exposure bake, which may be hereinafter referred to as "PEB") after the exposure to light, the substituent which has been giving a dissolution inhibiting effect on the resin is deprotected due to action of an acid. As a result, the exposed portion becomes soluble in alkali, and by treating the exposed portion with an alkali developing solution, a positive resist pattern can be obtained. In that case, the acid acts as a catalyst and exhibits its effect in a very small amount. Also action of the acid becomes active by the PEB and a chemical reaction is accelerated like a chain reaction, and thus sensitivity is enhanced.

Examples of conventional resins for chemically amplifying resist are phenol resins in which a part or the whole of hydroxyl is protected by a protective group such as acetal or ketal (KrF resist), methacrylic acid resins in which an acid-labile ester group is introduced to carboxyl (ArF resist) and the like.

However those conventional resist polymers have strong absorption in a wavelength range of a vacuum ultraviolet region and have a significant problem that transparency against $F_2$ laser beam having a wavelength of 157 nm which is studied in a process for ultra fine pattern is low (an absorption coefficient is high). Therefore for exposing with $F_2$ laser, it is necessary to make a resist film thickness very thin and it is substantially difficult to use the polymers as a single layer $F_2$ resist.

R. R. Kunz, T. M. Bloomstein, et al. suggest in Journal of Photopolymer Science and Technology (Vol. 12, No. 4 (1999) 561–569) that fluorocarbons have good transparency at 157 nm as compared with other various materials and have possibility of use as a $F_2$ resist.

However in that literature, there is only description that existing fluorocarbon polymers are high in transparency at 157 nm, but there is no description as to preferable structure of fluorine-containing polymers. Also, for example, with respect to a fluorine-containing polymer having functional group necessary for a positive type or negative type chemically amplifying resist, neither evaluation of transparency nor synthesis of the polymer was made. Moreover the literature does not suggest a fluorine-containing base polymer material being preferable as a chemically amplifying resist and a preferable resist composition obtained therefrom at all, and there is found no possibility of forming a $F_2$ resist pattern by using a fluorine-containing polymer.

Thereafter A. E. Feiring, et al. of E. I. du Pont de Nemours and Company disclosed in WO00/17712 pamphlet (published Mar. 30, 2000) that a specific fluorine-containing polymer is useful for $F_2$ resist application.

That pamphlet describes the use of a fluorine-containing polymer having a structural unit of fluoroolefin and a structural unit having a polycyclic condensed structure which is mainly a structural unit derived from norbornene.

Also an acid-labile (acid-decomposable) functional group necessary for a positive type resist is introduced to the fluorine-containing polymer by copolymerizing a conventional acrylic, methacrylic, norbornene or vinyl ester monomer with a monomer having an introduced acid-labile (acid-decomposable) functional group.

Further thereafter A. E. Feiring, et al. of E. I. du Pont de Nemours and Company disclosed in WO00/67072 pamphlet (published Nov. 9, 2000) that a fluorine-containing polymer having —C(Rf)(Rf')OH or —C(Rf(Rf')O—Rb is useful for $F_2$ resist application.

In that pamphlet, a structural unit of norbornene in which —C(Rf)(Rf')OH or —C(Rf)(Rf')O—Rb is bonded through a part of —CH$_2$OCH$_2$— is disclosed. Further there is disclosed norbornene derivatives having —C(Rf)(Rf')OH or —C(Rf)(Rf')O—Rb as an example of a fluorine-containing polymer to be used for a resist.

However in those patent publications, there is no description as to the use of a fluorine-containing copolymer comprising a structural unit of fluoroolefin and a structural unit having an aliphatic monocyclic structure in its trunk chain, and further there is no description as to an aliphatic monocyclic structure to which a functional group necessary for a resist is introduced.

Further Katsuyama, et al. of Matsushita Electric Industrial Co., Ltd. proposed a method of forming a pattern with exposure light having a wavelength of from 1 to 180 nm using a resist material containing halogen atom, etc. (JP2000-321774A published Nov. 24, 2000). However there is disclosed only a methacrylic resin having a structural unit of methacrylic acid ester having —$CH_2CF_3$ group and —$CH(CF_3)_2$ group in its side chain as a base resin having halogen atom for a resist, and neither a resin containing fluorine atom in its trunk chain nor a polymer having an aliphatic monocyclic structure in its trunk chain is disclosed. Also there is disclosed no polymer which has, in an aliphatic monocyclic structure, a functional group and is capable of working as a chemically amplifying resist (positive type or negative type).

There is generally known that dry etching resistance of a polymer is enhanced by introducing a norbornene backbone to the polymer. However transparency, particularly transparency in a vacuum ultraviolet region of conventional norbornene derivatives cannot be said to be sufficient.

The present inventors have found that fluoroolefins represented by tetrafluoroethylene have good copolymerizability with unsaturated compounds (monomers) of aliphatic monocyclic structure, and a novel fluorine-containing polymer was obtained. It has been considered that dry etching resistance of monocyclic compounds was insufficient as compared with compounds having polycyclic condensed structure. However the present inventors have found that the copolymer which is obtained in the present invention and comprises fluoroolefin and an unsaturated compound (monomer) of aliphatic monocyclic structure has dry etching resistance higher than that of an unsaturated compound having polycyclic condensed structure, for example, norbornene.

Also it was found that transparency in a vacuum ultraviolet region is excellent as compared with the use of norbornene.

Also studies have been made as to introduction of an acid-reactive functional group necessary for a resist, and as a result, it was found that in addition to the fluoroolefin and unsaturated compound (monomer) of aliphatic monocyclic structure, a specific ethylenic monomer having an acid-reactive functional group has good copolymerizability, which made it possible to introduce an acid-reactive functional group to a polymer. Further the present inventors have found a fluorine-containing polymer in which an acid-reactive functional group is introduced directly to a monocyclic structure and also a novel unsaturated compound of monocyclic structure having an acid-reactive functional group and partly having fluorine atoms. The copolymer comprising such a novel unsaturated compound of monocyclic structure and a fluoroolefin exhibits excellent dry etching resistance and high transparency when used for a resist.

SUMMARY OF THE INVENTION

The first object of the present invention is to provide a novel fluorine-containing polymer having an aliphatic monocyclic structure in its trunk chain.

The second object of the present invention is to provide a novel fluorine-containing unsaturated aliphatic monocyclic compound having functional group.

The third object of the present invention is to provide a chemically amplifying photoresist composition which comprises a fluorine-containing aliphatic monocyclic polymer having an acid-reactive group and a photoacid generator and can be used for a patterning process using $F_2$ laser as light source.

The present inventors have made intensive studies to achieve the above-mentioned objects and as a result, have found a novel fluorine-containing unsaturated aliphatic monocyclic compound and a novel fluorine-containing polymer having an aliphatic monocyclic structure in its trunk chain and have found that the fluorine-containing polymer is useful as a polymer for a resist.

Namely, the present inventors have made various studies with respect to copolymerization of a fluoroolefin, typically tetrafluoroethylene with unsaturated monocyclic hydrocarbon compounds and as a result, have found that a specific unsaturated monocyclic hydrocarbon compound which can constitute a ring in its trunk chain has good copolymerizability with fluoroolefins having 2 or 3 carbon atoms, and have found a novel fluorine-containing polymer.

The first of the present invention relates to novel fluorine-containing polymers. The first novel fluorine-containing polymer is a fluorine-containing polymer having an aliphatic monocyclic structure in the polymer trunk chain which has a number average molecular weight of from 500 to 1,000,000 and is represented by the formula (Ma):

-(M1)-(M2a)-(N)— (Ma)

in which
the structural unit M1 is a structural unit derived from an ethylenic monomer having 2 or 3 carbon atoms and at least one fluorine atom, the structural unit M2a is at least one structural unit which introduces an aliphatic monocyclic structure in the polymer trunk chain and is represented by the formula (a):

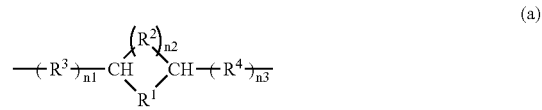

(a)

wherein $R^1$ is at least one hydrocarbon group selected from the group consisting of a divalent hydrocarbon group which has 1 to 8 carbon atoms and constitutes a ring (which may be further substituted with a hydrocarbon group or a fluorine-containing alkyl group) and a divalent hydrocarbon group having ether bond which has the sum of carbon atoms and oxygen atoms of 2 to 8 and constitutes a ring (which may be further substituted with a hydrocarbon group or a fluorine-containing alkyl group); $R^2$ is an alkylene group which has 1 to 3 carbon atoms and constitutes a ring; $R^3$ and $R^4$ are the same or different and each is a divalent alkylene group having 1 or 2 carbon atoms; n1, n2 and n3 are the same or different and each is 0 or 1, the structural unit N is a structural unit derived from a monomer copolymerizable with the monomers to introduce the structural units M1 and M2a, and the structural units M1, M2a and N are contained in amounts of from 1 to 99% by mole, from 1 to 99% by mole and from 0 to 98% by mole, respectively.

The second fluorine-containing polymer of the first invention is a fluorine-containing polymer having an aliphatic monocyclic structure in the polymer trunk chain which has a number average molecular weight of from 500 to 1,000,000 and is represented by the formula (Mb):

-(M1)-(M2b)-(N)— (Mb)

in which
the structural units M1 and N are as defined in the above-mentioned formula (Ma),
the structural unit M2b is at least one structural unit which introduces an aliphatic monocyclic structure in the trunk chain and is represented by the formula (b):

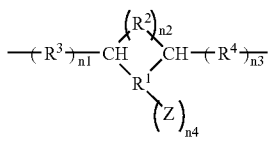

wherein $R^1$, $R^2$, $R^3$, $R^4$, n1, n2 and n3 are as defined in the above-mentioned formula (a); Z are the same or different and each is:

wherein $Z^1$ is at least one functional group selected from the group consisting of OH group, COOH group, a derivative of carboxylic acid group and a functional group protected by a protective group which can convert the functional group to OH group by reaction with an acid; $R^5$ is a divalent organic group; n5 is 0 or 1; n4 is an integer of from 1 to 3, and the structural units M1, M2b and N are contained in amounts of from 1 to 99% by mole, from 1 to 99% by mole and from 0 to 98% by mole, respectively.

The second of the present invention relates to a fluorine-containing unsaturated cyclic compound represented by the formula (1):

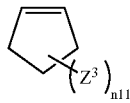

wherein $Z^3$ are the same or different and each is $-Rf^3-Z^4$, in which $Z^4$ is at least one functional group selected from the group consisting of OH group, COOH group, a derivative of carboxylic acid group and a functional group protected by a protective group which can converted the functional group to OH group by reaction with an acid; $Rf^3$ is a fluorine-containing alkylene group which has 1 to 30 carbon atoms and may have ether bond; n11 is an integer of from 1 to 4.

The third of the present invention relates to a photoresist composition which comprises:

(A-1) a fluorine-containing polymer having OH group, COOH group and/or a group which can be dissociated by an acid and converted to OH group or COOH group,
(B) a photoacid generator and
(C) a solvent, in which the fluorine-containing polymer (A-1) is a polymer comprising a structural unit derived from a fluoroolefin and a structural unit derived from a monomer introducing an aliphatic monocyclic structure in the polymer trunk chain.

The fourth of the present invention relates to a photoresist composition which comprises:

(A-2) a fluorine-containing polymer having OH group which has recurring units of an aliphatic monocyclic structure in the polymer trunk chain, in which OH group or a moiety having OH group is bonded to the carbon atom constituting the aliphatic monocyclic structure,
(B) a photoacid generator and
(C) a solvent, in which when in the recurring units of the aliphatic monocyclic structure of the fluorine-containing polymer (A-2), the carbon atom bonded to OH group is named the first carbon atom and a structure consisting of the first carbon atom up to the neighboring fourth carbon atom is assumed to be a model structure, the model structure having OH group satisfies Equation 1:

$$\Delta H = H(M-O^-) + 200 - H(M-OH) \leq 75 \qquad \text{(Equation 1)}$$

and further Equation 2:

$$\Delta H = H(M-O^{31}) + 200 - H(M-OH) \leq 70 \qquad \text{(Equation 2)}$$

wherein H(M-OH) is a produced enthalpy of the model structure, H(M-O$^-$) is a produced enthalpy of the model structure after dissociation of the OH group and a produced enthalpy of hydrogen ion is assumed to be a constant of 200 kJ/mol.

The fifth of the present invention relates to a photoresist composition which comprises:

(A-3) a fluorine-containing polymer having OH group which has recurring units of an aliphatic monocyclic structure in the polymer trunk chain, in which OH group or a moiety having OH group is bonded to the carbon atom constituting the aliphatic monocyclic structure,
(B) a photoacid generator and
(C) a solvent, in which the recurring units of the aliphatic monocyclic structure of the fluorine-containing polymer (A-3) have a structure represented by the formula (50):

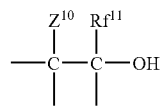

wherein $R^{11}$ is a perfluoroalkyl group having 1 to 20 carbon atoms; $Z^{10}$ is fluorine atom or a perfluoroalkyl group having 1 to 20 carbon atoms.

The OH group in the recurring units of the aliphatic monocyclic structure may be protected by a protective group.

The sixth of the present invention relates to a photoresist composition which comprises:

(A-5) a fluorine-containing polymer having OH group which has recurring units of an aliphatic monocyclic structure in the polymer trunk chain, in which OH group or a moiety having OH group is bonded to the carbon atom constituting the aliphatic monocyclic structure,
(B) a photoacid generator and
(C) a solvent, in which the fluorine-containing polymer (A-5) is a polymer having a structural unit represented by the formula (53):

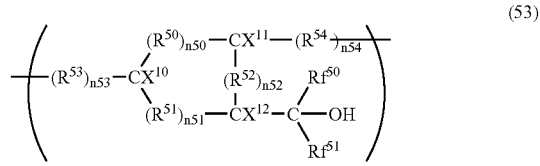

wherein $Rf^{50}$ and $Rf^{51}$ are the same or different and each is a perfluoroalkyl group having 1 to 20 carbon atoms; $X^{10}$ and $X^{11}$ are the same or different and each is H, F, an alkyl group having 1 to 20 carbon atoms or a fluorine-containing alkyl group which has 1 to 20 carbon atoms and may have ether bond; $X^{12}$ is hydrogen atom, fluorine atom, an alkyl group having 1 to 20 carbon atoms, a fluorine-containing alkyl group which has 1 to 20 carbon atoms and may have ether bond, OH group or a group represented by the formula:

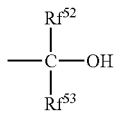

wherein $Rf^{52}$ and $Rf^{53}$ are the same or different and each is a perfluoroalkyl group having 1 to 20 carbon atoms; $R^{50}$ is at least one selected from an alkylene group or fluorine-containing alkylene group which has 1 to 3 carbon atoms and constitutes a ring; $R^{51}$ and $R^{52}$ are the same or different and each is at least one selected from a divalent hydrocarbon group which has 1 to 7 carbon atoms and constitutes a ring, oxygen atom, a divalent hydrocarbon group having ether bond which has the sum of oxygen atoms and carbon atoms of 2 to 7 and constitutes a ring, a divalent fluorine-containing alkylene group which has 1 to 7 carbon atoms and constitutes a ring or a divalent fluorine-containing alkylene group having ether bond which has the sum of oxygen atoms and carbon atoms of 2 to 7 and constitutes a ring; the sum of carbon atoms constituting a trunk chain in $R^{51}$ and $R^{52}$ is not more than 7, and OH group or a group represented by the formula:

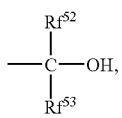

wherein $Rf^{52}$ and $Rf^{53}$ are as defined above, may be bonded to any of carbon atoms in $R^{51}$; $R^{53}$ and $R^{54}$ are the same or different and each is a divalent alkylene group having 1 or 2 carbon atoms or a divalent fluorine-containing alkylene group having 1 or 2 carbon atoms; n50, n51, n52, n53 and n54 are the same or different and each is 0 or 1.

The seventh of the present invention relates to a photoresist composition which comprises:

(A-5) a fluorine-containing polymer having OH group which has recurring units of an aliphatic monocyclic structure in the polymer trunk chain, in which OH group or a moiety having OH group is bonded to the carbon atom constituting the aliphatic monocyclic structure, (B) a photoacid generator and (C) a solvent, in which the fluorine-containing polymer (A-5) is a polymer having a structural unit represented by the formula (54):

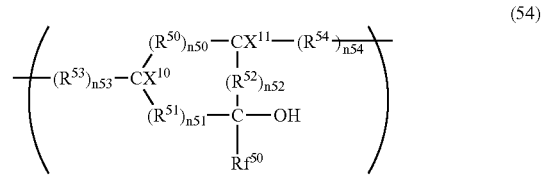

wherein $Rf^{50}$ is a perfluoroalkyl group having 1 to 20 carbon atoms; $X^{10}$ and $X^{11}$ are the same or different and each is H, F, an alkyl group having 1 to 20 carbon atoms or a fluorine-containing alkyl group which has 1 to 20 carbon atoms and may have ether bond; $R^{50}$ is at least one selected from an alkylene group or fluorine-containing alkylene group which has 1 to 3 carbon atoms and constitutes a ring; $R^{51}$ and $R^{52}$ are the same or different and each is at least one selected from a divalent hydrocarbon group which has 1 to 7 carbon atoms and constitutes a ring, oxygen atom, a divalent hydrocarbon group having ether bond which has the sum of oxygen atoms and carbon atoms of 2 to 7 and constitutes a ring, a divalent fluorine-containing alkylene group which has 1 to 7 carbon atoms and constitutes a ring or a divalent fluorine-containing alkylene group having ether bond which has the sum of oxygen atoms and carbon atoms of 2 to 7 and constitutes a ring; the sum of carbon atoms constituting a trunk chain in $R^{51}$ and $R^{52}$ is not more than 7, and OH group or a group represented by the formula:

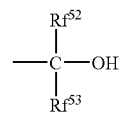

wherein $Rf^{52}$ and $Rf^{53}$ are the same or different and each is a perfluoroalkyl group having 1 to 20 carbon atoms, may be bonded to any of carbon atoms in $R^{51}$; $R^{53}$ and $R^{54}$ are the same or different and each is a divalent alkylene group having 1 or 2 carbon atoms or a divalent fluorine-containing alkylene group having 1 or 2 carbon atoms; n50, n51, n52, n53 and n54 are the same or different and each is 0 or 1.

It is preferable that in the formula (53), $X^{12}$ is fluorine atom or a perfluoroalkyl group having 1 to 20 carbon atoms and that in $R^{51}$ or $R^{52}$ of the formula (54), at least one fluorine atom or perfluoroalkyl group having 1 to 20 carbon atoms is bonded to at least one of neighboring carbon atoms of the carbon atom bonded to the OH group.

Further in the formula (54), also preferred is a structural unit having, in the structure of $R^{51}$, at least one structural unit represented by the formula:

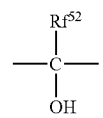

wherein $Rf^{52}$ is as defined above.

The eighth of the present invention relates to a fluorine-containing polymer having a number average molecular weight of from 500 to 1,000,000 which is represented by the formula (61):

-(M3-1)-(N3-1)- (61)

in which M3-1 is a structural unit represented by the formula (53):

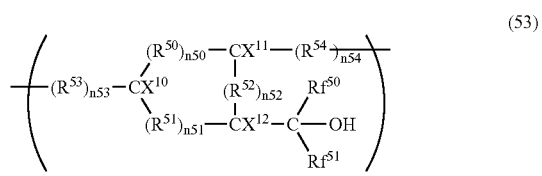

(53)

wherein $Rf^{50}$ and $Rf^{51}$ are the same or different and each is a perfluoroalkyl group having 1 to 20 carbon atoms; $X^{10}$ and $X^{11}$ are the same or different and each is H, F, an alkyl group having 1 to 20 carbon atoms or a fluorine-containing alkyl group which has 1 to 20 carbon atoms and may have ether bond; $X^{12}$ is hydrogen atom, fluorine atom, an alkyl group having 1 to 20 carbon atoms, a fluorine-containing alkyl group which has 1 to 20 carbon atoms and may have ether bond, OH group or a group represented by the formula:

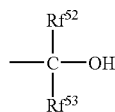

wherein $Rf^{52}$ and $Rf^{53}$ are the same or different and each is a perfluoroalkyl group having 1 to 20 carbon atoms; $R^{50}$ is at least one selected from an alkylene group or fluorine-containing alkylene group which has 1 to 3 carbon atoms and constitutes a ring; $R^{51}$ and $R^{52}$ are the same or different and each is at least one selected from a divalent hydrocarbon group which has 1 to 7 carbon atoms and constitutes a ring, oxygen atom, a divalent hydrocarbon group having ether bond which has the sum of oxygen atoms and carbon atoms of 2 to 7 and constitutes a ring, a divalent fluorine-containing alkylene group which has 1 to 7 carbon atoms and constitutes a ring or a divalent fluorine-containing alkylene group having ether bond which has the sum of oxygen atoms and carbon atoms of 2 to 7 and constitutes a ring; the sum of carbon atoms constituting a trunk chain in $R^{51}$ and $R^{52}$ is not more than 7, and OH group or a group represented by the formula:

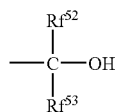

wherein $Rf^{52}$ and $Rf^{53}$ are as defined above, may be bonded to any of carbon atoms in $R^{51}$; $R^{53}$ and $R^{54}$ are the same or different and each is a divalent alkylene group having 1 or 2 carbon atoms or a divalent fluorine-containing alkylene group having 1 or 2 carbon atoms; n50, n51, n52, n53 and n54 are the same or different and each is 0 or 1, N3-1 is a structural unit derived from a monomer copolymerizable with the monomer to introduce the structural unit M3-1, and the structural units M3-1 and N3-1 are contained in amounts of from 0.1 to 100% by mole and from 0 to 99.9% by mole, respectively.

The ninth of the present invention relates to a fluorine-containing polymer having a number average molecular weight of from 500 to 1,000,000 which is represented by the formula (61):

-(M3-1)-(N3-1)- (61)

in which M3-1 is a structural unit represented by the formula (54):

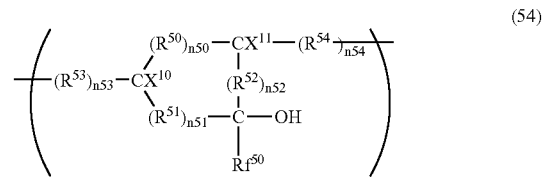

(54)

wherein $Rf^{50}$ is a perfluoroalkyl group having 1 to 20 carbon atoms; $X^{10}$ and $X^{11}$ are the same or different and each is H, F, an alkyl group having 1 to 20 carbon atoms or a fluorine-containing alkyl group which has 1 to 20 carbon atoms and may have ether bond; $R^{50}$ is at least one selected from an alkylene group or fluorine-containing alkylene group which has 1 to 3 carbon atoms and constitutes a ring; $R^{51}$ and $R^{52}$ are the same or different and each is at least one selected from a divalent hydrocarbon group which has 1 to 7 carbon atoms and constitutes a ring, oxygen atom, a divalent hydrocarbon group having ether bond which has the sum of oxygen atoms and carbon atoms of 2 to 7 and constitutes a ring, a divalent fluorine-containing alkylene group which has 1 to 7 carbon atoms and constitutes a ring or a divalent fluorine-containing alkylene group having ether bond which has the sum of oxygen atoms and carbon atoms of 2 to 7 and constitutes a ring; the sum of carbon atoms constituting a trunk chain in $R^{51}$ and $R^{52}$ is not more than 7, and OH group or a group represented by the formula:

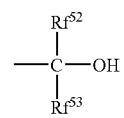

wherein $Rf^{52}$ and $Rf^{53}$ are the same or different and each is a perfluoroalkyl group having 1 to 20 carbon atoms, may be bonded to any of carbon atoms in $R^{51}$; $R^{53}$ and $R^{54}$ are the same or different and each is a divalent alkylene group having 1 or 2 carbon atoms or a divalent fluorine-containing alkylene group having 1 or 2 carbon atoms; n50, n51, n52, n53 and n54 are the same or different and each is 0 or 1, N3-1 is a structural unit derived from a monomer copolymerizable with the monomer to introduce the structural unit M3-1, and the structural units M3-1 and N3-1 are contained in amounts of from 0.1 to 100% by mole and from 0 to 99.9% by mole, respectively.

It is preferable that in the formula (53), $X^{12}$ is fluorine atom or a perfluoroalkyl group having 1 to 20 carbon atoms, or that in $R^{51}$ or $R^{52}$ of the formula (54), at least one of fluorine atom or a perfluoroalkyl group having 1 to 20 carbon atoms is bonded to at least one of neighboring carbon atoms of the carbon atom bonded to OH group.

Further in the formula (54), also preferred is a structural unit having, in the structure of $R^{51}$, at least one structural unit represented by the formula:

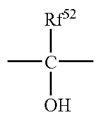

wherein $Rf^{52}$ is as defined above.

Further it is preferable that the above-mentioned structural unit M3-1 is a structural unit satisfying the above-mentioned Equation 1 and further Equation 2.

The tenth of the present invention relates to a fluorine-containing cyclopentene having OH group which is represented by the formula (70):

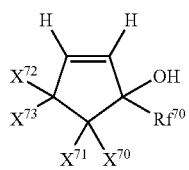

wherein $Rf^{70}$ is a perfluoroalkyl group having 1 to 20 carbon atoms; $X^{70}$ is fluorine atom or a perfluoroalkyl group having 1 to 20 carbon atoms; $X^{71}$ is hydrogen atom, fluorine atom, a hydrocarbon group having 1 to 20 carbon atoms or a perfluoroalkyl group having 1 to 20 carbon atoms; $X^{72}$ is hydrogen atom, fluorine atom, OH group, a hydrocarbon group having 1 to 20 carbon atoms or a perfluoroalkyl group having 1 to 20 carbon atoms; $X^{73}$ is hydrogen atom, fluorine atom, a hydrocarbon group having 1 to 20 carbon atoms or a perfluoroalkyl group having 1 to 20 carbon atoms; when $X^{72}$ is OH group, $X^{73}$ is not fluorine atom.

In the above-mentioned formula (70), it is preferable that both of $X^{70}$ and $X^{71}$ are fluorine atoms or perfluoroalkyl groups having 1 to 20 carbon atoms or $X^{72}$ is OH group and $X^{73}$ is a perfluoroalkyl group having 1 to 20 carbon atoms.

DETAILED DESCRIPTION

Figure 1:
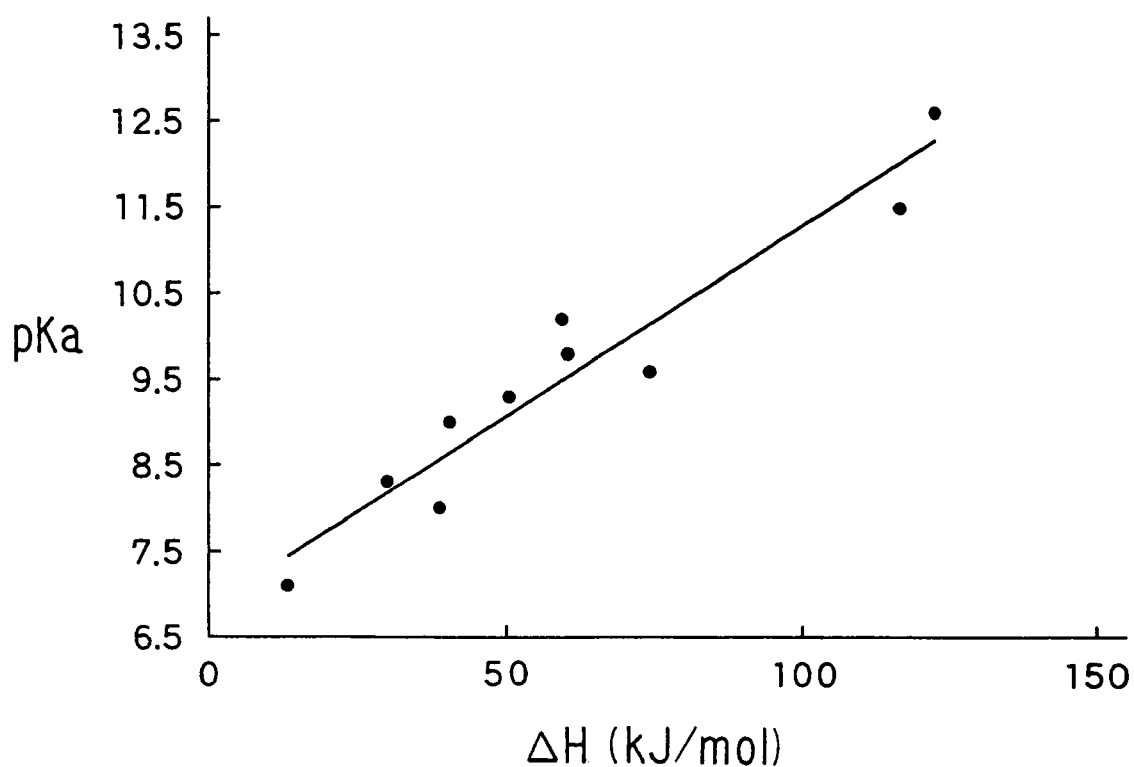
FIG. 1 is a graph in which ΔH and pKa calculated in Experimental Example 1 are plotted.

First, the first novel fluorine-containing polymer of the present invention is explained below.

The first novel fluorine-containing polymer is, as mentioned above, a fluorine-containing polymer having an aliphatic monocyclic structure in the polymer trunk chain which has a number average molecular weight of from 500 to 1,000,000 and is represented by the formula (Ma):

-(M1)-(M2a)-(N)— (Ma)

in which the structural unit M1 is a structural unit derived from an ethylenic monomer having 2 or 3 carbon atoms and at least one fluorine atom, the structural unit M2a is at least one structural unit which introduces an aliphatic monocyclic structure in the polymer trunk chain and is represented by the formula (a):

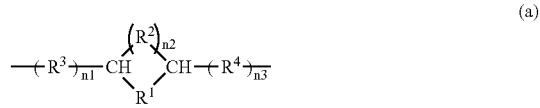

wherein $R^1$ is at least one hydrocarbon group selected from the group consisting of a divalent hydrocarbon group which has 1 to 8 carbon atoms and constitutes a ring (which may be further substituted with a hydrocarbon group or a fluorine-containing alkyl group) and a divalent hydrocarbon group having ether bond which has the sum of carbon atoms and oxygen atoms of 2 to 8 and constitutes a ring (which may be further substituted with a hydrocarbon group or a fluorine-containing alkyl group); $R^2$ is an alkylene group which has 1 to 3 carbon atoms and constitutes a ring; $R^3$ and $R^4$ are the same or different and each is a divalent alkylene group having 1 or 2 carbon atoms; n1, n2 and n3 are the same or different and each is 0 or 1, the structural unit N is a structural unit derived from a monomer copolymerizable with the monomers to introduce the structural units M1 and M2a, and the structural units M1, M2a and N are contained in amounts of from 1 to 99% by mole, from 1 to 99% by mole and from 0 to 98% by mole, respectively.

In the structural unit M2a introducing the monocyclic structure, the divalent hydrocarbon groups $R^1$ and $R^2$ constitute a ring, and two neighboring carbon atoms of the divalent hydrocarbon group $R^1$ may be bonded to each other without $R^2$.

The divalent hydrocarbon group $R^1$ in the structural unit M2a is a divalent hydrocarbon group which constitutes a ring and has 1 to 8 carbon atoms, and hydrogen atom thereof may be substituted with a hydrocarbon group (for example, a hydrocarbon group having 1 to 20 carbon atoms, preferably an alkyl group having 1 to 5 carbon atoms) or a fluorine-containing alkyl group (for example, a fluorine-containing alkyl group which has 1 to 20 carbon atoms and may have ether bond, preferably a fluorine-containing alkyl group which has 1 to 5 carbon atoms and may have ether bond or a perfluoroalkyl group which may have ether bond). $R^1$ may have an unsaturated bond.

The divalent hydrocarbon group $R^1$ may have ether bond, and in that case, is a group which has the sum of carbon atoms and oxygen atoms of from 2 to 8 and constitutes a ring. Hydrogen atoms of $R^1$ also may be substituted with hydrocarbon groups or fluorine-containing alkyl groups similar to those mentioned above, and $R^1$ may have an unsaturated bond.

In the first fluorine-containing polymer of the present invention, the structural unit M2a constituting a ring does not have functional group.

Examples of preferred structural unit M2a are structural units derived from unsaturated aliphatic monocyclic compounds such as:

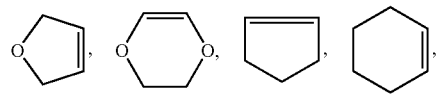

-continued

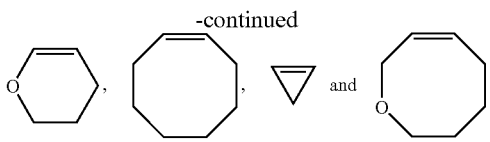

The structural unit M2a encompasses those in which hydrogen atoms other than the hydrogen atoms bonded to the carbon atoms of carbon-carbon double bond are substituted with a hydrocarbon group (for example, a hydrocarbon group having 1 to 20 carbon atoms, preferably an alkyl group having 1 to 5 carbon atoms) or a fluorine-containing alkyl group (for example, a fluorine-containing alkyl group which has 1 to 20 carbon atoms and may have ether bond, preferably a fluorine-containing alkyl group which has 1 to 5 carbon atoms and may have ether bond or a perfluoroalkyl group which may have ether bond).

Among them, preferred are unsaturated compounds constituting a three-membered ring (in the formula (a), any of n1, n2 and n3 are 0 and the number of carbon atoms of $R^1$ constituting a ring is 1), five-membered ring (in the formula (a), any of n1, n2 and n3 are 0 and the number of carbon atoms of $R^1$ constituting a ring is 3) or eight-membered ring (in the formula (a), any of n1, n2 and n3 are 0 and the number of carbon atoms of $R^1$ constituting a ring is 6) from the viewpoint of good copolymerizability with fluoroolefins, and particularly preferred are three-membered ring and eight-membered ring.

More concretely it is preferable that the structural unit M2a is a structural unit represented by the formula (a-1):

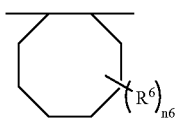

(a-1)

wherein $R^6$ is selected from hydrogen atom, an alkyl group having 1 to 5 carbon atoms or a fluorine-containing alkyl group which has 1 to 5 carbon atoms and may have ether bond; n6 is 0 or an integer of from 1 to 12, or the formula (a-2):

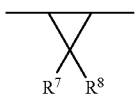

(a-2)

wherein $R^7$ and $R^8$ are the same or different and each is hydrogen atom, an alkyl group having 1 to 5 carbon atoms or a fluorine-containing alkyl group which has 1 to 5 carbon atoms and may have ether bond.

The second novel fluorine-containing polymer of the present invention is, as mentioned above, a fluorine-containing polymer having an aliphatic monocyclic structure in the polymer trunk chain which has a number average molecular weight of from 500 to 1,000,000 and is represented by the formula (Mb):

—(M1)-(M2b)-(N)— (Mb)

in which
the structural units M1 and N are as defined in the above-mentioned formula (Ma),
the structural unit M2b is at least one structural unit which introduces an aliphatic monocyclic structure in the polymer trunk chain and is represented by the formula (b):

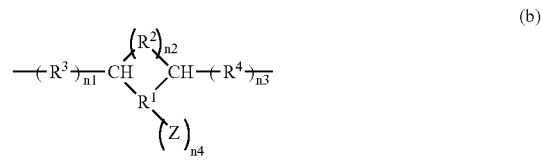

(b)

wherein $R^1$, $R^2$, $R^3$, $R^4$, n1, n2 and n3 are as defined in the above-mentioned formula (a); Z are the same or different and each is:

wherein $Z^1$ is at least one functional group selected from the group consisting of OH group, COOH group, a derivative of carboxylic acid group and a functional group protected by a protective group which can convert the functional group to OH group by reaction with an acid; $R^5$ is a divalent organic group; n5 is 0 or 1; n4 is an integer of from 1 to 3, and the structural units M1, M2b and N are contained in amounts of from 1 to 99% by mole, from 1 to 99% by mole and from 0 to 98% by mole, respectively.

Those fluorine-containing polymers have a moiety Z having functional group which is introduced to carbon atom constituting a ring structure equal to the ring structure of the above-mentioned structural unit M2a having a ring structure, and photosensitivity necessary for resist application and various useful functions for other applications can be imparted to the polymer.

Particularly in the resist application, it is preferable to introduce the functional group directly to the ring structure because a polymer having excellent dry etching resistance and transparency can be obtained.

The moiety Z having functional group is represented by the formula:

and the functional group $Z^1$ is at least one functional group selected from the group consisting of OH group, COOH group, a derivative of carboxylic acid group and a functional group protected by a protective group which can convert the functional group to OH group by reaction with an acid.

Among them, the derivative of carboxylic acid group is selected from carboxylic acid esters, functional groups protected by a protective group which can convert the functional group to COOH group due to reaction with an acid, carboxylic acid halides and acid amides. Preferred are carboxylic acid esters and functional groups protected by a protective group which can convert the functional group to COOH group due to reaction with an acid. The derivative of carboxylic acid group is selected, for example, from —COOR$^{10}$, wherein $R^{10}$ is an alkyl group having 1 to 10 carbon atoms or —COO—P group mentioned infra.

The functional group (abbreviated to —COO—P) protecting the above-mentioned functional group with a protective group (—P) which can convert the functional group to COOH group due to reaction with an acid is a functional group necessary, for example, for the use in positive type resist application, and has a function that the protective group (—P) is released due to reaction with an acid generated from a photoacid generator and converts the functional group to COOH group, thereby making a polymer soluble in an alkali developing solution though the whole polymer is insoluble in an alkali developing solution due to action of the protective group before the reaction with an acid.

Examples of the functional group (—COO—P) having a protective group which converts the functional group to COOH group due to reaction with an acid are:

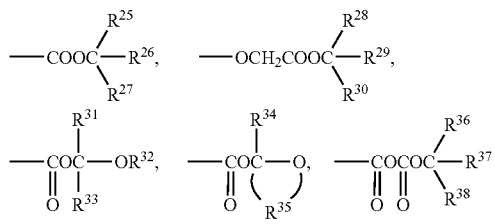

and the like, wherein $R^{25}$, $R^{26}$, $R^{27}$, $R^{28}$, $R^{29}$ $R^{30}$, $R^{31}$, $R^{32}$, $R^{36}$, $R^{37}$ and $R^{38}$ are the same or different and each is a hydrocarbon group having 1 to 10 carbon atoms; $R^{33}$ and $R^{34}$ are the same or different and each is H or a hydrocarbon group having 1 to 10 carbon atoms; $R^{35}$ is a divalent hydrocarbon group having 2 to 10 carbon atoms. More concretely there are preferably:

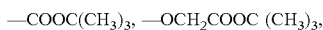

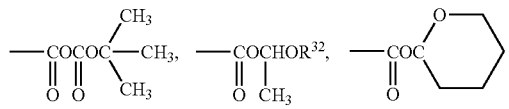

and the like, wherein $R^{32}$ is as defined above.

The functional group (abbreviated to —O—P) protecting the above-mentioned functional group with a protective group (—P) which can convert the functional group to —OH group due to reaction with an acid is a functional group necessary, for example, for the use in positive type resist application, and has a function that the protective group (—P) is released due to reaction with an acid generated from a photoacid generator and converts the functional group to OH group, thereby making a polymer soluble in an alkali developing solution though the whole polymer is insoluble in an alkali developing solution due to action of the protective group before the reaction with an acid.

Examples of the functional group (—O—P) having a protective group which converts the functional group to —OH group due to reaction with an acid are preferably groups represented by:

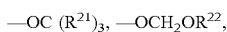

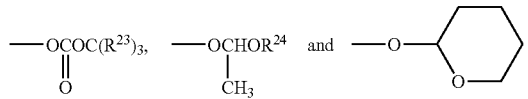

wherein $R^{21}$, $R^{22}$, $R^{23}$ and $R^{24}$ are the same or different and each is an alkyl group having 1 to 5 carbon atoms. More concretely there are preferably:

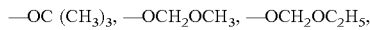

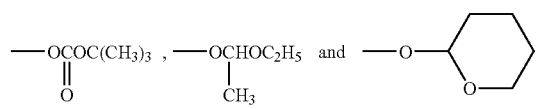

and among them, from the viewpoint of good reactivity with an acid, preferred are:

—OC(CH$_3$)$_3$,

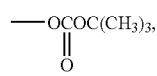

and further from the viewpoint of good transparency, preferred are —OC(CH$_3$)$_3$, —OCH$_2$OCH$_3$ and —OCH$_2$OC$_2$H$_5$.

The moiety Z having functional group may have $R^5$, or the moiety Z may not have $R^5$ and the functional group $Z^1$ may be bonded directly to the ring structure.

When the moiety Z have $R^5$, $R^5$ may be one selected from divalent organic groups. Examples thereof are preferably a divalent hydrocarbon group which has 1 to 30 carbon atoms and may have ether bond and a fluorine-containing divalent alkylene group having 1 to 30 carbon atoms and ether bond.

Examples of preferred moiety Z having functional group are those represented by the formula:

—(R$^9$)$_{n7}$—COOR$^{10}$, wherein $R^9$ is an alkylene group which has 1 to 10 carbon atoms and may have ether bond or a fluorine-containing alkylene group which has 1 to 10 carbon atoms and may have ether bond; $R^{10}$ is hydrogen atom or an alkyl group having 1 to 10 carbon atoms; n7 is 0 or 1. More concretely there are:

—COOR$^{10}$, —CH$_2$COOR$^{10}$, —CH$_2$CH$_2$COOR$^{10}$,

—CH$_2$CH(CH$_3$)COOR$^{10}$,

—CF$_2$COOR$^{10}$, —CF$_2$CF$_2$COOR$^{10}$,
—CH$_2$CH$_2$CF$_2$CF$_2$COOR$^{10}$,

—OCH$_2$COOR$^{10}$ and the like.

Also Z is preferably an alcohol structure represented by the formula:

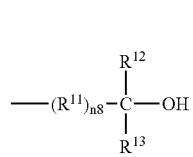

wherein $R^{11}$ is an alkylene group which has 1 to 5 carbon atoms and may have ether bond or a fluorine-containing alkylene group which has 1 to 5 carbon atoms and may have ether bond; $R^{12}$ and $R^{13}$ are the same or different and each is hydrogen atom, an alkyl group having 1 to 10 carbon atoms, an aryl group having 3 to 10 carbon atoms, a fluorine-containing alkyl group which has 1 to 10 carbon atoms and may have ether bond or a fluorine-containing aryl group which has 3 to 10 carbon atoms and may have ether bond; n8 is 0 or 1. Among them, preferred is a structure having fluorine atom, for example, a structure represented by the formula:

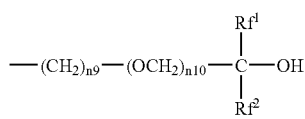

wherein $Rf^1$ is a fluorine-containing alkyl group which has 1 to 10 carbon atoms and may have ether bond; $Rf^2$ is hydrogen atom, an alkyl group having 1 to 10 carbon atoms, an aryl group having 3 to 10 carbon atoms or a fluorine-containing alkyl group which has 1 to 10 carbon atoms and may have ether bond; n9 is 0 or an integer of from 1 to 5; n10 is 0 or 1, from the viewpoint of transparency and solubility in a developing solution in the case of resist application.

In the above-mentioned fluorine-containing alcohol structure, it is further preferable that $Rf^1$ and $Rf^2$ are the same or different and each is a perfluoroalkyl group having 1 to 5 carbon atoms, from the viewpoint of transparency and solubility in a developing solution.

Examples of preferred alcohol structure are:

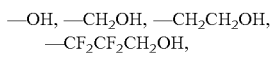

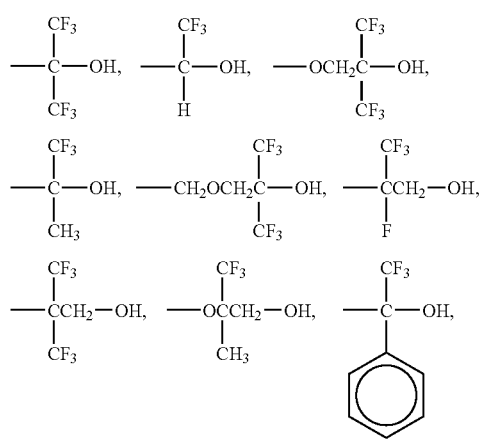

and the like.

In the second fluorine-containing polymer of the present invention, example of preferred structural unit M2b forming a ring is a structural unit represented by the formula (b-1):

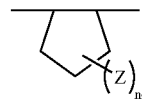

(b-1)

wherein Z and n4 are as defined in the formula (b), and examples of the moiety having functional group are the same as those preferably exemplified supra.

Also the present inventors have found that when a specific diallyl compound having functional group is subjected to cyclic copolymerization with a fluoroolefin, a fluorine-containing copolymer having a monocyclic structure in the polymer trunk chain can be obtained.

Thereby structural units represented by the formula (b-2):

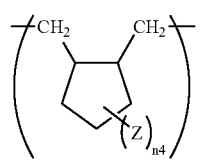

(b-2)

and/or the formula (b-3):

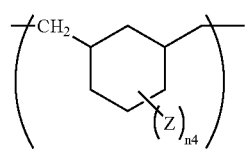

(b-3)

wherein Z and n4 are as defined above, can be obtained.

Concretely when, for example, a diallyl compound represented by:

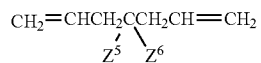

wherein $Z^5$ is the same as the above-mentioned Z and $Z^6$ is H or is the same as the above-mentioned Z, is subjected to cyclic copolymerization with a fluoroolefin, structural units represented by the formula (b-4):

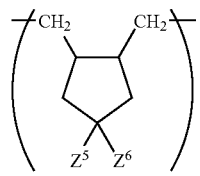

(b-4)

and/or the formula (b-5):

$$\left(\begin{array}{c}\text{CH}_2\\ \\ Z^5\quad Z^6\end{array}\right) \quad \text{(b-5)}$$

wherein $Z^5$ and $Z^6$ are as defined above, can be obtained.

In the above-mentioned formulae (b-4) and (b-5), it is preferable from the viewpoint of copolymerizability that $Z^5$ and $Z^6$ are the same or different and each is at least one selected from COOH or a derivative of carboxylic acid group.

Example of preferred derivative of carboxylic acid group is one selected from carboxylic acid esters, functional groups protected by a protective group which can convert the functional group to COOH group due to reaction with an acid, acid halides and acid amides.

In the fluorine-containing polymer of the present invention, the structural unit M1 derived from a fluoroolefin is at least one structural unit selected from structural units derived from fluorine-containing ethylenic monomers having 2 or 3 carbon atoms. Examples thereof are, for instance, tetrafluoroethylene, chlorotrifluoroethylene, vinylidene fluoride, vinyl fluoride, trifluoroethylene, hexafluoropropylene and the like.

Among them, preferred are structural units derived from tetrafluoroethylene and chlorotrifluoroethylene because transparency and dry etching resistance can be improved in resist application.

In the polymers of the formulae (Ma) and (Mb) of the present invention, the structural unit M1, the structural unit M2a or M2b and the structural unit N are contained in amounts of from 1 to 99% by mole, from 1 to 99% by mole and from 0 to 98% by mole, respectively. Provided that (M1)+(M2a) or (M1)+(M2b) is 100% by mole, a percent by mole ratio of (M1)/(M2a) or (M1)/(M2b) is preferably 80/20 to 20/80, more preferably 70/30 to 30/70, further preferably 60/40 to 40/60.

The present inventors have found that a specific ethylenic monomer having functional group can be copolymerized in addition to the fluoroolefin and the above-mentioned monomer being capable of introducing a monocyclic structure, thereby making it possible to introduce the functional group to the fluorine-containing polymer having a monocyclic structure in its trunk chain.

Accordingly photosensitivity necessary in resist application and various useful functions necessary in other applications can be imparted to the polymer.

The structural unit derived from an ethylenic monomer having functional group which is copolymerized with the fluoroolefin and the monomer introducing the monocyclic structure is a structural unit derived from an ethylenic monomer and represented by the formula (N-1):

$$-\!\!+\!\!(CX^1X^2-CX^3)\!\!\!\!\!\!-\!\!\!\!\!\!\!\!\!\!\!\!\!\!\!\!\!\!\!\!\!\!\!\!\!\!\!\! \atop (CX^4X^5)_a(O)_b-(Rf)_c-Z^2 \quad \text{(N-1)}$$

wherein $X^1$ and $X^2$ are the same or different and each is H or F; $X^3$ is H, F, CH$_3$ or CF$_3$; $X^4$ and $X^5$ are the same or different and each is H, F or CF$_3$; Rf is a fluorine-containing alkylene group having 1 to 40 carbon atoms or a fluorine-containing alkylene group having 2 to 100 carbon atoms and ether bond; a is 0 or an integer of from 1 to 3; b and c are the same or different and each is 0 or 1; $Z^2$ is at least one functional group selected from the group consisting of OH group, COOH group, a derivative of carboxylic acid group and a functional group protected by a protective group which can convert the functional group to OH group due to reaction with an acid.

Examples thereof are, for instance, as follows.

(i) Structural unit derived from acrylic monomer and represented by:

$$-\!\!+\!\!(CX^1X^2-CX^3)\!\!\!\!\!\!-\!\!\!\!\!\!\!\!\!\!\!\!\!\!\!\!\!\!\!\!\!\!\!\!\!\! \atop COO-R$$

wherein $X^1$ and $X^2$ are the same or different and each is H or F; $X^3$ is H, F, CH$_3$ or CF$_3$; R is selected from hydrogen atom, a hydrocarbon group having 1 to 20 carbon atoms, a fluorine-containing alkyl group having 1 to 20 carbon atoms, a fluorine-containing alkyl group having 2 to 100 carbon atoms and ether bond or a fluorine-containing aryl group having 3 to 20 carbon atoms.

In the above-mentioned formula, examples of preferred —R are:

hydrogen atom,

—C(CH$_3$)$_3$, —CH$_2$CH$_2$OH, —(CH$_2$)$_m$(CF$_2$)$_n$—F,
—(CH$_2$)$_m$(CF$_2$)$_n$—H,

—(CH$_2$)$_m$(CF$_2$)$_n$—Cl, (m is an integer of from 1 to 5, n is an integer of from 1 to 10)

—CH(CF$_3$)$_2$, —CH$_2$CFHCF$_3$, —(CH$_2$)$_m$(CF$_2$)$_n$—CF(CF$_3$)$_2$, (m is an integer of from 1 to 5, n is an integer of from 1 to 10)

$$-\!\!-\!\!CH_2CF(OCF_2CF)_m\!\!-\!\!F, \atop CF_3 \quad\quad CF_3$$

(m is an integer of from 1 to 10)

$$\begin{array}{cc} CF_3 & CF_3 \\ | & | \\ -\!\!-\!\!C-\!\!CF_3, & -\!\!-\!\!CH_2C-\!\!CF_3 \\ | & | \\ CF_3 & CH_3 \end{array}$$

and the like.

Examples thereof are, for instance, acrylic acid, methacrylic acid, α-fluoroacrylic acid, α-trifluoromethylacrylic acid, acrylic acid esters, α-fluoroacrylic acid esters, methacrylic acid esters, α-trifluoromethylacrylic acid esters, hydroxyethyl acrylate, hydroxyethyl methacrylate, glycidyl acrylate, glycidyl methacrylate, acrylamides, methacrylamides and the like.

The introduction of the structural unit derived therefrom is preferred because it is possible to enhance solubility in a solvent, photosensitivity with a photoacid generator, adhesion to a substrate and compatibility with a photoacid generator and other additives.

It is preferable that at least any one of $X^1$, $X^2$ and $X^3$ has fluorine atom and/or $X^3$ is a trifluoromethyl group, from the viewpoint of transparency and dry etching resistance. It is particularly preferable that $X^3$ is fluorine atom or a trifluoromethyl group.

(ii) Structural unit derived from fluorine-containing ethylenic monomer having functional group and represented by:

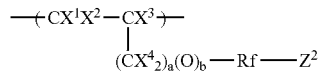

wherein $X^1$, $X^2$, $X^3$, $X^4$, a, b, Rf and $Z^2$ are as defined in the formula (N-1).

Particularly preferred is a structural unit represented by:

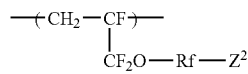

wherein Rf and $Z^2$ are as defined in the formula (N-1).

Concretely there are preferably structural units derived from fluorine-containing ethylenic monomers such as:

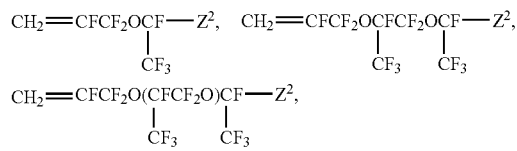

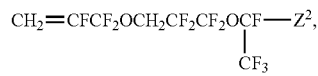

and the like, wherein $Z^2$ is as defined in the formula (N-1). Also preferred is a structural unit represented by the formula:

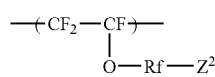

wherein Rf and $Z^2$ are as defined in the formula (N-1). Concretely there are preferably structural units derived from monomers such as:

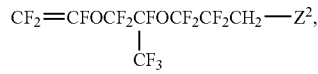

$CF_2$=$CFO(CF_2)_3Z^2$, $CF_2$=$CFO(CF_2)_3CH_2$-$Z^2$, $CF_2$=$CFOCF_2CF_2OCF_2$-$Z^2$, $CF_2$=$CFOCF_2CF_2OCF_2CH_2$-$Z^2$, $CF_2$=$CFOCF_2CF_2CH_2OCF_2CF_2$-$Z^2$, $CF_2$=$CFOCF_2CF_2CH_2OCF_2CF_2CH_2$-$Z^2$,

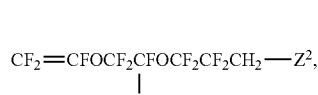

$CF_2$=$CFO(CF_2)_3Z^2$, $CF_2$=$CFO(CF_2)_3CH_2$-$Z^2$, $CF_2$=$CFOCF_2CF_2OCF_2$-$Z^2$, $CF_2$=$CFOCF_2CF_2OCF_2CH_2$-$Z^2$, $CF_2$=$CFOCF_2CF_2CH_2OCF_2CF_2$-$Z^2$, $CF_2$=$CFOCF_2CF_2CH_2OCF_2CF_2CH_2$-$Z^2$ and the like, wherein $Z^2$ is as defined in the formula (N-1).

Examples of the other fluorine-containing ethylenic monomer having functional group are:

$CF_2$=$CFCF_2$—O—Rf-$Z^2$, $CF_2$=$CF$—Rf-$Z^2$, $CH_2$=$CH$—Rf-$Z^2$, $CH_2$=$CHO$—Rf-$Z^2$ and the like, wherein Rf and $Z^2$ are as defined in the formula (N-1).

More concretely there are:

$CF_2$=$CFCF_2OCF_2CF_2CF_2$-$Z^2$, $CF_2$=$CFCF_2OCF_2CF_2CF_2CH_2$-$Z^2$,

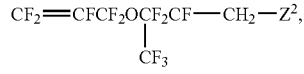

$CF_2$=$CFCF_2$-$Z^2$, $CF_2$=$CFCF_2CH_2$-$Z^2$, $CH_2$=$CHCF_2OF_2CH_2CH_2$-$Z^2$, $CH_2$=$CHCF_2CF_2$-$Z^2$, $CH_2$=$CHCF_2CF_2CH_2$-$Z^2$,
$CH_2$=$CHCF_2CF_2CF_2CF_2$-$Z^2$, $CH_2$=$CHCF_2CF_2CF_2CF_2CH_2$-$Z^2$, $CH_2$=$CHO$—$CH_2CF_2CF_2$-$Z^2$, $CH_2$=$CHOCH_2CF_2CF_2CH_2$-$Z^2$ and the like, wherein $Z^2$ is as defined in the formula (N-1).

Examples of the functional group $Z^2$ contained in the above-mentioned respective structural units N1 are preferably the same as the examples of the above-mentioned functional group $Z^1$.

The fluorine-containing polymer of the present invention having the structural unit N1 having functional group is represented by the formula (Ma-1):

-(M1)-(M2a)-(N1)-(N)—           (Ma-1)

wherein M1 and M2a are as defined in the above-mentioned formula (Ma) and the structural unit N1 is the same as the formula (N-1). Examples of preferred structural units M1, M2a and N1 are the same as the preferred examples mentioned supra.

Further the structural unit N1 having functional group may be introduced to a fluorine-containing polymer having functional group on the ring, namely, the polymer is represented by the formula (Mb-1):

-(M1)-(M2b)-(N1)-(N)—           (Mb-1)

wherein M1 and M2b are as defined in the formula (Mb) and the structural unit N1 is the same as the formula (N-1). Examples of preferred structural units M1, M2b and N1 are preferably the same as the preferred examples mentioned supra. The polymer represented by the formula (Mb-1) is preferred because functional groups can be introduced in a higher content and resolution can be improved in the case of use in resist application.

With respect to proportions of each structural unit in the polymers of the formulae (Ma-1) and (Mb-1) of the present invention, the structural units M1, M2a or M2b, N1 and N are contained in amounts of from 1 to 98% by mole, from 1 to 98% by mole, from 1 to 98% by mole and from 0 to 97% by mole, respectively. It is preferable that when (M1)+(M2a)+(N1) or (M1)+(M2b)+(N1) is 100% by mole, a percent by mole ratio of ((M1)+(M2a))/(N1) or ((M1)+(M2b))/(N1) is 99/1 to 20/80, more preferably 95/5 to 30/70, further preferably 90/10 to 40/60.

In the formulae (Ma), (Mb), (Ma-1) and (Mb-1) of the present invention, the structural unit N is an optional component copolymerizable with the other structural units.

Examples of the optional component are, for instance,
(i) Structural units derived from fluorine-containing ethylenic monomers (excluding M1)

For example, there are preferably structural units derived from monomers such as:

$CF_2=C(CF_3)_2$, $CH_2=C(CF_3)_2$, $CF_2=CFO(CF_2CFO)_n-C_3F_7$,
             |
             $CF_3$ $CF_2=CFO(CF_2)_nX$, (n: 1 to 10)

$CH_2=CFCF_2O(CFCF_2O)_{n1}CFHCF_3$   (n1: 0 to 10),
          |
          $CF_3$ $CH_2=CF\text{-}(CF_2)_mX$, $CH_2=CH\,(CF_2)_mX$, $CF_2=CF(CF_2)_mX$, and the like, wherein X is selected from H, F and Cl, m is from 2 to 10.

(ii) Structural units derived from ethylenic monomers having no fluorine

The structural units derived from ethylenic monomers having no fluorine may be introduced to the polymer within a range not lowering transparency and dry etching resistance (within a range where the refractive index does not increase).

The introduction of these structural units is preferred since adhesion to a substrate is improved, solubility in a general-purpose solvent is enhanced and compatibility with, for example, a photoacid generator and additives to be added as case demands can be improved.

Examples of the non-fluorine-containing ethylenic monomer are as follows.

α-Olefins:
Ethylene, propylene, butene, vinyl chloride, vinylidene chloride and the like.

Vinyl ether or vinyl ester monomers:
$CH_2=CHOR$, $CH_2=CHOCOR$ (R: hydrocarbon group having 1 to 20 carbon atoms) and the like.

Allyl monomers:
$CH_2=CHCH_2Cl$,                        $CH_2=CHCH_2OH$,
$CH_2=CHCH_2COOH$, $CH_2=CHCH_2Br$ and the like.

Allyl ether monomers:
$CH_2=CHCH_2OR$
(R: hydrocarbon group having 1 to 20 carbon atoms), $CH_2=CHCH_2OCH_2CH_2COOH$,

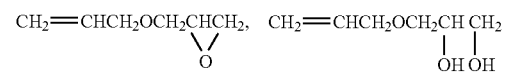

and the like.

The molecular weight of the fluorine-containing polymers of the formulae (Ma), (Mb), (Ma-1) and (Mb-1) of the present invention can be selected in a range of from 500 to 1,000,000 in number average molecular weight depending on application, purpose and form in use of the polymer. Preferred molecular weight is from 1,000 to 700,000, more preferably from about 2,000 to about 500,000. When the molecular weight is too low, heat resistance and mechanical properties of the obtained polymer coating film easily becomes insufficient, and a too high molecular weight is apt to be disadvantageous from the viewpoint of processability. Particularly in the case of aiming at forming a thin coating film by using the polymer as a coating material, a too high molecular weight is disadvantageous from the viewpoint of film forming property. The molecular weight is preferably not more than 300,000, particularly preferably not more than 200,000.

The fluorine-containing polymers of the formulae (Ma), (Mb), (Ma-1) and (Mb-1) of the present invention can be obtained by various processes, for example, by copolymerizing, through known process, monomers corresponding to the respective structural units, namely, the fluoroolefin (M1), the unsaturated compound having a monocyclic structure or the diene compound (M2) being capable of undergoing cyclic polymerization, the ethylenic monomer (N1) having functional group as case demands and the monomer (N) corresponding to the optional component. For the polymerization, radical polymerization method, anion polymerization method, cation polymerization method and the like can be employed. Among them, the radical polymerization method is preferably used from the point that each monomer for obtaining the polymer of the present invention has good radical polymerizability, control of composition and molecular weight is easy and production in an industrial scale is easy.

Namely, in order to initiate the polymerization, means for initiation is not limited particularly as far as the polymerization proceeds radically. The polymerization is initiated, for example, with an organic or inorganic radical polymerization initiator, heat, light, ionizing radiation or the like. The polymerization can be carried out by solution polymerization, bulk polymerization, suspension polymerization, emulsion polymerization or the like. The molecular weight is controlled by the contents of monomers to be used for the polymerization, the content of polymerization initiator, the content of chain transfer agent, temperature, etc. The components of the copolymer to be produced can be controlled by the starting monomer components.

The second of the present invention relates to a novel fluorine-containing unsaturated aliphatic monocyclic compound having functional group.

The novel fluorine-containing unsaturated cyclic compound of the present invention is a compound represented by the formula (1):

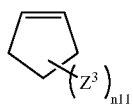

(1)

wherein $Z^3$ are the same or different and each is $-Rf^3-Z^4$, in which $Z^4$ is at least one functional group selected from the group consisting of OH group, COOH group, a derivative of carboxylic acid group and a functional group protected by a protective group which can convert the functional group to OH group due to reaction with an acid; $Rf^3$ is a fluorine-containing alkylene group which has 1 to 30 carbon atoms and may have ether bond; n11 is an integer of from 1 to 4.

The compound of the formula (1) of the present invention is a fluorine-containing unsaturated cyclic compound having functional group, and the moiety $Z^3$ having functional group and bonded to the cyclic structure is characterized by having a fluorine-containing alkylene group $Rf^3$, which is preferred because copolymerizability with fluoroolefins becomes better and transparency of the obtained fluorine-containing polymer becomes excellent.

Examples of preferred functional group $Z^4$ are the same as the examples of the functional group $Z^1$ contained in the structural unit of the formula (b) in the above-mentioned fluorine-containing polymer.

Examples of preferred fluorine-containing alkylene group $Rf^3$ are:

—(CF$_2$)$_n$—, —(CH$_2$)$_m$—(CF$_2$)$_n$— (m and n are integers of from 1 to 10),

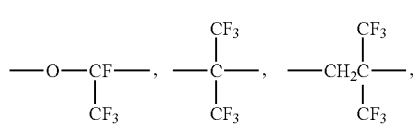

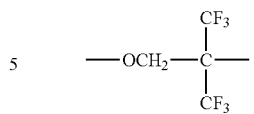

and the like.

The first of the preferred fluorine-containing unsaturated cyclic compounds of the present invention is represented by the formula (2):

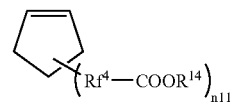

(2)

wherein $Rf^4$ is a perfluoroalkylene group which has 1 to 10 carbon atoms and may have ether bond; $R^{14}$ is hydrogen atom or an alkyl group having 1 to 10 carbon atoms; n11 is as defined in the formula (1).

Examples thereof are:

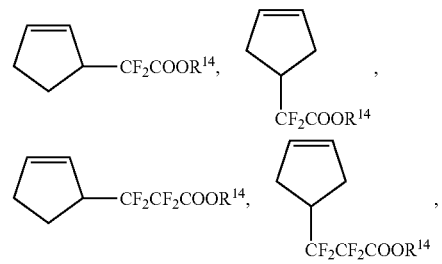

and the like.

Those unsaturated cyclic compounds may be synthesized by any processes. For example, synthesis can be carried out by the following process.

First, a halide $X^4-Rf^4-COOR^{14}$, in which $X^4$ is selected from bromine or iodine, is reacted at low temperature directly with a metal such as zinc, magnesium or Li or with an organometallic compound comprising the above-mentioned metal such as a Grignard reagent or an alkyl lithium compound, thus preparing a fluorine-containing alkylation agent $X^4MRf^4-COOR^{14}$, in which $X^4$ is bromine or iodine, M is a metal.

Next, a halide of cyclopentene:

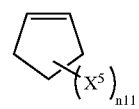

wherein $X^5$ is selected from chlorine, bromine and iodine, is reacted at low temperature with the previously prepared fluorine-containing alkylation agent $X^4MRf^4$—$COOR^{14}$ and thereby a fluorine-containing cyclopentene compound having carboxylic acid or derivative of carboxylic acid corresponding thereto can be obtained.

The second of the preferred fluorine-containing unsaturated cyclic compound of the present invention is a cyclopentene compound having a fluorine-containing alcohol structure which is represented by the formula (3):

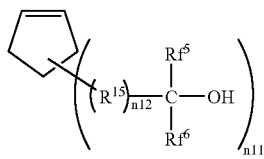

(3)

wherein $R^{15}$ is an alkylene group which has 1 to 5 carbon atoms and may have ether bond or a fluorine-containing alkylene group which has 1 to 5 carbon atoms and may have ether bond; $Rf^5$ is a fluorine-containing alkyl group which has 1 to 10 carbon atoms and may have ether bond; $Rf^6$ is hydrogen atom, an alkyl group having 1 to 10 carbon atoms or a fluorine-containing alkyl group which has 1 to 10 carbon atoms and may have ether bond; n12 is 0 or 1; n11 is as defined in the formula (1).

Particularly preferred is a cyclopentene compound having a fluorine-containing alcohol structure which is represented by the formula (4):

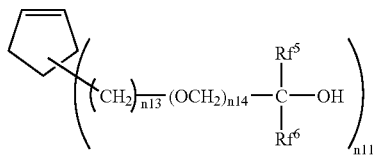

(4)

wherein $Rf^5$ and $Rf^6$ are as defined in the above-mentioned formula; n13 is 0 or an integer of from 1 to 5; n14 is 0 or 1; n11 is as defined in the formula (1).

Further it is preferable that $Rf^5$ and $Rf^6$ are the same or different and each is a perfluoroalkyl group having 1 to 5 carbon atoms.

Those cyclopentene compounds having a fluorine-containing alcohol structure are particularly useful monomers for resist application because particularly high transparency can be imparted to the polymer obtained by copolymerization and solubility in a developing solution can also be imparted because of high acidity of OH group.

Examples of those cyclopentene compounds having a fluorine-containing alcohol structure are:

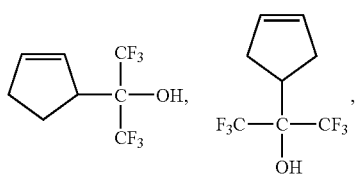

-continued

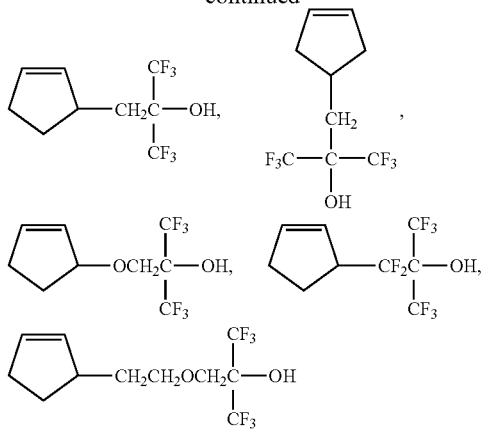

and the like.

Those unsaturated cyclic compounds may be synthesized by any processes. For example, synthesis can be carried out by the following process.

First, a magnesium metal is reacted directly with a halide of cyclopentene compound:

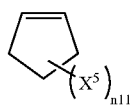

wherein $X^5$ is selected from chlorine, bromine and iodine, to synthesize a cyclopentene magnesium halide (Grignard reagent) and then hexafluoro acetone is reacted therewith, and thus an unsaturated cyclic compound can be produced.

The third of the present invention relates to the photoresist composition, preferably the chemically amplifying photoresist composition which comprises a fluorine-containing aliphatic monocyclic polymer having an acid-reactive group and a photoacid generator and can be used for a patterning process using $F_2$ laser as light source.

The chemically amplifying photoresist comprises a resin (polymer) component and a photoacid generator. An acid is generated from the acid generator at an energy-exposed portion of the resist and a catalytic action of the acid is used. In the chemically amplifying positive photoresist, an acid generated at an energy-exposed portion is scattered by the following heat-treatment (post exposure bake: hereinafter abbreviated to PEB) to release an acid-labile or acid-decomposable functional group of the resin and re-generate an acid, thereby making the energy-exposed portion soluble in alkali. The chemically amplifying negative photoresist generally has a functional group being capable of undergoing condensation reaction by an acid and is alkali-soluble. The negative photoresist contains a crosslinking agent in addition to the resin component and acid generator.

The photoresist composition of the present invention (preferably chemically amplifying photoresist composition) can be used as the above-mentioned positive type and negative type photoresists and comprises:

(A-1) a fluorine-containing polymer having OH group, COOH group and/or a group which can be dissociated by an acid and converted to OH group or COOH group, (B) a photoacid generator and
(C) a solvent, in which the fluorine-containing polymer (A-1) is a polymer comprising a structural unit derived from a fluoroolefin and a structural unit derived from a monomer introducing an aliphatic monocyclic structure in the polymer trunk chain, preferably, among the above-mentioned polymers having an aliphatic monocyclic structure in the polymer trunk chain, a fluorine-containing polymer having, as a functional group, OH group, COOH group and/or a functional group protected by a protective group which can convert the functional group to OH group or COOH group by reaction with an acid.

It has been considered that when a polymer having a monocyclic structure was used for a resist, dry etching resistance was insufficient. The present inventors have found that enough dry etching resistance can be obtained by copolymerizing a structural unit having a monocyclic structure in its trunk chain with a fluoroolefin.

The fluorine-containing polymer (A-1) to be used in the photoresist composition of the present invention (preferably chemically amplifying photoresist composition) is selected from those having a functional group working for a positive or negative resist among the above-mentioned fluorine-containing polymers having functional group of the formula (Mb) and/or (Ma-1).

The functional group working for a resist represents OH group, COOH group, a functional group (—O—P) protected by a protective group (—P) which can convert the functional group to OH group by reaction with an acid or a functional group (—COO—P) protected by a protective group (—P) which can convert the functional group to COOH group by reaction with an acid, and at least one of them is selected.

Examples of the protected functional groups —O—P and —COO—P are preferably the same as those described in the above-mentioned explanation with respect to the functional group of the fluorine-containing polymer.

When the fluorine-containing polymer is used for the photoresist composition (preferably chemically amplifying photoresist composition), the content of the above-mentioned functional group in the polymer (when a plurality of functional groups are used, the sum thereof) varies depending on the polymer backbone and kind of the functional group and is from 5 to 80% by mole, preferably from 20 to 70% by mole, more preferably from 30 to 60% by mole based on the whole structural units. When the content is too low, it is not preferred because solubility in a developing solution and resolution become insufficient. When the content is too high, it is not preferred because transparency and dry etching resistance are lowered.

The fluorine-containing polymer (A-1) to be used in the photoresist composition (preferably chemically amplifying photoresist composition) can be selected from the preferred examples of the above-mentioned fluorine-containing polymers (functional group is selected from those mentioned above).

As a result of further studies by the present inventors, it was found that a fluorine-containing polymer having a specific monocyclic structure having hydroxyl (OH) group in trunk chain is well dissolved in an alkaline developing solution which is used in a developing step of photoresist process.

Also it was found that a composition comprising the above fluorine-containing polymer or the fluorine-containing polymer having protected OH group and a photoacid generator is useful as a photoresist composition.

Namely, the fourth of the present invention relates to a photoresist composition which comprises:
(A-2) a fluorine-containing polymer having OH group which has recurring units of an aliphatic monocyclic structure in the polymer trunk chain, in which OH group or a moiety having OH group is bonded to the carbon atom constituting the aliphatic monocyclic structure,
(B) a photoacid generator and
(C) a solvent, in which when in the recurring units of aliphatic monocyclic structure of the fluorine-containing polymer (A-2), the carbon atom bonded to OH group is named the first carbon atom and a structure consisting of the first carbon atom up to the neighboring fourth carbon atom is assumed to be a model structure, the model structure having OH group satisfies Equation 1:

$$\Delta H = H(M-O^-) + 200 - H(M-OH) \leq 75 \qquad \text{(Equation 1),}$$

preferably Equation 2:

$$\Delta H = H(M-O^-) + 200 - H(M-OH) \leq 70 \qquad \text{(Equation 2)}$$

wherein H(M-OH) is a produced enthalpy of the model structure, H(M-O$^-$) is a produced enthalpy of the model structure after dissociation of the OH group and a produced enthalpy of hydrogen ion is assumed to be a constant of 200 kJ/mol.

It has been generally said that with respect to a relation between an acidity and alkali solubility, when an acidity is increased, namely when an acid dissociation constant pKa is decreased, alkali solubility becomes high. However, it is not always said that any of compositions having a smaller pKa have high solubility in alkali. For example, solubility of a resist in a developing solution is not determined only by pKa of a OH group-containing monomer.

For example, a pKa value of OH group of phenol which is a representative example of hydrocarbon compound having OH group is 10 and solubility in a developing solution is good. However among fluorine-containing polymers obtained by copolymerizing a OH group-containing monomer having a pKa value of about 10, there are some polymers insoluble in a developing solution.

As mentioned above, it has been difficult to select a compound having an optimum solubility in a developing solution only by a pKa value.

The present inventors have made another approach to the above-mentioned problem taking account of produced energy of OH group before and after the acid dissociation and have found that a fluorine-containing polymer having OH group which has, in its trunk chain, recurring units satisfying a specific equation of $\Delta H$ (difference in produced energy) defined above has unexpectedly excellent solubility in a developing solution. This equation of $\Delta H$ mentioned above was firstly found by the present inventors.

Conventional hydrocarbon compounds having OH group have a pKa value of not less than 12, generally from 14 to 16. However those hydrocarbon compounds do not have enough correlation between the above-mentioned difference in produced enthalpy ($\Delta H$) of OH group before and after the dissociation and the actually measured pKa value.

As mentioned above, the present inventors actually measured pKa values of various fluorine-containing compounds having OH group and on the other hand, suggested the above-mentioned $\Delta H$. As a result of investigation with respect to a relation between the $\Delta H$ and the actually measured pKa value, the present inventors have found that the pKa value of particularly a fluorine-containing compound having OH group which has a pKa value of not more than 12 has a good proportional relation with the ΔH, and further have found that a pKa value of OH group of a fluorine-containing compound having OH group can be conjectured by calculating ΔH of the compound according to the equation (Equation1 or Equation 2).

When paying attention to application as a polymer for a resist, it is necessary for the polymer to have high solubility in an alkaline developing solution such as an aqueous solution of 2.38% by weight of tetramethylammonium hydroxide which is generally used in a developing step. On the other hand, in F2 resist application, transparency at 157 nm in a vacuum ultraviolet region is required and the use of carboxyl group and phenolic hydroxyl group which have been used for conventional resists as a group soluble in a developing solution is disadvantageous from the viewpoint of transparency. Therefore, in the polymer structure, it is necessary to select a structure including OH group and its neighboring structure which gives high transparency and excellent solubility in a developing solution.

Hitherto studies have been made with respect to the use of a fluorine-containing polymer to which a norbornene backbone having —C(CF$_3$)$_2$OH group as a group soluble in a developing solution is introduced, as a polymer for F2 resist possessing improved transparency and solubility in a developing solution (WO00/67072, etc.). However though the OH group of this fluorine-containing polymer has solubility in a developing solution by an effect of two CF$_3$ groups, a dissolving rate of the polymer itself is insufficient only by the introduction of —C(CF$_3$)$_2$OH.

The present inventors have studied various fluorine-containing monomers having OH group and structural units derived therefrom taking advantage of the above-mentioned relation between ΔH and pKa value. As a result, the present inventors defined a model structure of not only —C(CF$_3$)$_2$OH portion but also its neighboring structure and calculated ΔH thereof and have found that when the ΔH is not more than a specific value, the polymer possesses good solubility in a developing solution.

Based on those new findings, further studies have been made, and it was found that the fluorine-containing polymer having, in the polymer trunk chain, recurring units of aliphatic monocyclic structure having OH group which satisfies the above-mentioned equation of ΔH (Equation 1 or Equation 2) or the fluorine-containing polymer having a functional group protecting the OH group is excellent in solubility in a developing solution while maintaining excellent transparency as the resist polymer.

Next, a method of calculating a difference ΔH in produced energy before and after acid dissociation in the present invention is explained below.

First, the aliphatic monocyclic structural unit having OH group in the polymer is selected. Provided that the carbon atom bonded to OH group of the aliphatic monocyclic structural unit is the first carbon atom, attention is paid only to the neighboring carbon atoms and the carbon atom adjacent to the first carbon atom is assumed to be the second carbon atom and the carbon atom adjacent to the second carbon atom is assumed to be the third carbon atom. A structure up to the fourth carbon atom is selected. If an atomic valence on the fourth carbon atom is insufficient, structure subjected to replacement with hydrogen atom is assumed to be the model structure. When the number of carbon atoms constituting the aliphatic monocyclic structural unit is few and the fourth carbon atom is not present, the aliphatic monocyclic structural unit is assumed to be a model structure.

The reason why the structure up to the fourth carbon atom is assumed to be the model structure is that even if a structure including the fifth or more carbon atoms which are far from OH is considered, it does not have an effect greatly on the ΔH value, and for comparing ΔH, the structure up to the fourth carbon atom suffices. Also in case of a large model structure, there arises a problem that a sufficient accuracy is difficult to obtain by a software of calculation method of molecular orbital available on the market, which is not preferable.

If technical problems of the calculation are solved, the ΔH value of the whole fluorine-containing monomer having the aliphatic monocyclic structure may be calculated without using the model structure.

For example, in the case of a structure which is represented by the formula:

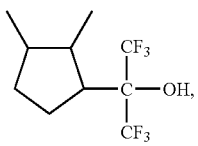

when the carbon atoms are numbered, the structure is represented by:

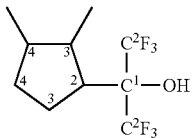

and the structure including carbon atoms up to the fourth carbon atom (C$^4$) constitutes a ring. A structure having hydrogen atoms bonded to the carbon atoms (C$^3$ and C$^4$) having insufficient atomic valence is used as the model structure.

Then the calculation of molecular orbital of the adopted model structure is first carried out to calculate a produced enthalpy: H(M-OH) before the acid dissociation.

Each produced enthalpy is calculated using the semi-empirical calculation method of molecular orbital: AM1 method (described in Journal of American Chemical Society, 107, p3902 (1985) by M. J. S. Dewar, E. G. Zoebisch, E. F.Heary and J. J. P. Stewart,). In the present invention, the calculation is carried out using MOPAC calculation software MOPAC97 (software for calculation of molecular orbital) available from FUJITSU LIMITED which uses CS Chem3D (R) Version 4.0 available from Cambridge Soft Corporation.

With respect to the same model structure in which OH has been dissociated, a produced enthalpy H(M-O$^-$) after the acid dissociation is calculated by the same method as above. The produced enthalpy of hydrogen ion is set at 200 kJ/mol as a constant.

The ΔH values of the respective aliphatic monocyclic structures (model structure) having OH group in the fluorine-containing polymer are determined unambiguously by the above-mentioned calculation.

It is a surprise that the above-mentioned Equation 1 and Equation 2 can be applied on the fluorine-containing polymer having, in its trunk chain, a structural unit derived from a fluorine-containing ethylenic monomer having OH group and also the fluorine-containing polymer having, in its trunk chain, a structural unit derived from a fluorine-containing norbornene derivative.

In the case of the fluorine-containing polymer prepared by copolymerizing a fluorine-containing ethylenic monomer having OH group, the model structure thereof is determined by the following method.

Provided that the carbon atom bonded to OH group is the first carbon atom, attention is paid only to the neighboring carbon atoms and the carbon atom adjacent to the first carbon atom is assumed to be the second carbon atom and the carbon atom adjacent to the second carbon atom is assumed to be the third carbon atom. A structure up to the third or the fourth carbon atom is selected. If an atomic valence on the third or the fourth carbon atom is insufficient, a structure subjected to replacement with hydrogen atom is assumed to be the model structure.

The reason why the structure up to the fourth carbon atom at maximum is assumed to be the model structure is the same as mentioned above. If technical problems of the calculation are solved, the ΔH value of the whole fluorine-containing ethylenic monomer may be calculated without using the model structure, which is also as mentioned above. However if the number of fluorine atoms in the structure increases, accuracy of the MOPAC calculation (explained infra) is lowered. Therefore, when the number of fluorine atoms in the model structure up to the fourth carbon is not less than seven, it is preferable that the calculation is carried out using a structure up to the third carbon as the model structure.

For example, in the case of a fluorine-containing ethylenic monomer having OH group which is represented by the formula:

CH$_2$=CHCH$_2$C(CF$_3$)$_2$OH, when the carbon atoms are numbered, the monomer is represented by:

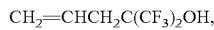
C$^4$H$_2$=C$^3$HC$^2$H$_2$C$^1$(C$^2$F$_3$)$_2$OH and the structure including carbon atoms up to the fourth carbon atom (C$^4$) and having six or less fluorine atoms can be used for the calculation. Therefore the whole molecular structure CH$_2$=CHCH$_2$C(CF$_3$)$_2$OH is used for the calculation.

Also in the case of the following fluorine-containing ethylenic monomer:

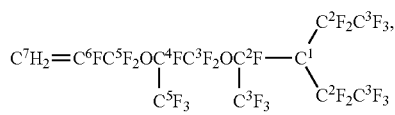

when carbon atoms up to the fourth carbon atom (C$^4$) are used, the number of fluorine atoms is not less than seven.

Therefore the model structure up to the third carbon atom (C$^3$), namely:

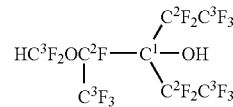

is used for the calculation of the structural unit derived from the fluorine-containing ethylenic monomer having OH group.

Next, in the case of a fluorine-containing polymer having a structural unit derived from a fluorine-containing norbornene derivative in its trunk chain, the model structure is basically selected according to the same definition as in the aliphatic monocyclic structural unit.

For example, in the case of:

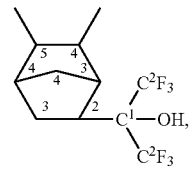

when carbon atoms up to the fourth one is used, the model structure of the structural unit derived from a fluorine-containing norbornene derivative is represented by:

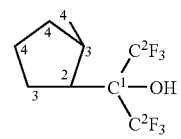

and, the structure subjected to bonding of hydrogen to the carbon (C$^4$) due to insufficient atomic valence can be used as the model structure.

In this case, too, if technical problems of the calculation are solved because a percentage of replacement with fluorine atom is small, the ΔH value of the whole structural unit derived from a fluorine-containing norbornene derivative may be calculated.

The fluorine-containing polymer (A-2) for the photoresist composition of the present invention has a structural unit having not more than 75 kJ/mol of the ΔH value calculated by the above-mentioned method among the aliphatic monocyclic structures (model structure) having OH group. This polymer is preferable as a photoresist being excellent in transparency and being high in solubility in an aqueous solution (developing solution) of 2.38% by weight of tetramethylammonium hydroxide in which fluorine-containing polymers have been said to be hardly dissolved.

The ΔH value is preferably not more than 70 kJ/mol, more preferably not more than 50 kJ/mol. When the ΔH value is too large, solubility in a developing solution of the polymer obtained by polymerization becomes insufficient, and at forming a resist pattern, a sufficient resolution is not obtained, a fine pattern is not obtained and scum and residue easily remain in the resist. A lower limit of the ΔH value is −110 kJ/mol, preferably not less than −65 kJ/mol, more preferably not less than −40 kJ/mol.

The photoresist composition of the fifth of the present invention is a photoresist composition which comprises:

(A-3) a fluorine-containing polymer having OH group which has recurring units of an aliphatic monocyclic structure in the polymer trunk chain, in which OH group or a moiety having OH group is bonded to the carbon atom constituting the aliphatic monocyclic structure,
(B) a photoacid generator and
(C) a solvent, in which the recurring units of the aliphatic monocyclic structure of the fluorine-containing polymer (A-3) have a structure represented by the formula (50):

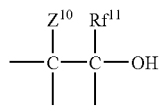
(50)

wherein $Rf^{11}$ is a perfluoroalkyl group having 1 to 20 carbon atoms; $Z^{10}$ is fluorine atom or a perfluoroalkyl group having 1 to 20 carbon atoms.

The fluorine-containing polymer (A-3) having such a structure of the formula (50) exhibits better solubility in an aqueous solution of 2.38% by weight of tetramethylammonium hydroxide which is generally used as a developing solution for a resist, because of effects of $Rf^{11}$ and in addition, the group $Z^{10}$ bonded to the neighboring carbon atom of the carbon atom bonded to $Rf^{11}$ and therefore, is preferred as a resist polymer.

In the structure of the formula (50), $Rf^{11}$ is a perfluoroalkyl group and examples thereof are $F(CF_2)_{n1}$ (n1 is an integer of from 1 to 20),

(n2 is an integer of from 1 to 6) and

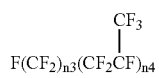

(n3 and n4 are integers which make the sum of carbon atoms being not more than 20), and among them, $CF_3$, $C_2F_5$, $C_3F_7$, $C_4F_9$, $(CF_3)_2CF$ and the like are preferred.

In the structure of the formula (50), $Z^{10}$ is selected from fluorine atom or a perfluoroalkyl group having 1 to 20 carbon atoms. Examples of preferred perfluoroalkyl group are the same as those of $Rf^{11}$, and particularly preferred are F, $CF_3$ and $C_2F_5$.

The structure of the formula (50) may be present in the form of a side chain on the aliphatic monocyclic structure constituting the fluorine-containing polymer (A-3) or in the form of a part of the ring structure forming the aliphatic monocyclic structure. Also at least one OH group may be present in one molecule of the monocyclic structure, and the aliphatic monocyclic structure may have two or more OH groups.

Example of the preferred structure of the formula (50) in the recurring units of aliphatic monocyclic structure of the fluorine-containing polymer (A-3) is a structure represented by the formula (51):

(51)

wherein $Rf^{11}$ and $Rf^{12}$ are the same or different and each is a perfluoroalkyl group having 1 to 20 carbon atoms; $Z^{10}$ is fluorine atom or a perfluoroalkyl group having 1 to 20 carbon atoms.

In the structure of the formula (51), examples of the $Rf^{12}$ are preferably the same as those of the $Rf^{11}$. $Rf^{11}$ and $Rf^{12}$ may be the same or different.

Also the structure of the formula (51) may be present in the form of a side chain on the aliphatic monocyclic structure constituting the fluorine-containing polymer (A-3) or in the form of a part of the ring structure forming the aliphatic monocyclic structure. At least one OH group may be present in one molecule of the monocyclic structure, and the aliphatic monocyclic structure may have two or more OH groups.

Also preferable example of the structure of the formula (50) in the recurring units of aliphatic monocyclic structure of the fluorine-containing polymer (A-3) is a structure represented by the formula (52):

(52)

wherein $Rf^{11}$ is a perfluoroalkyl group having 1 to 20 carbon atoms; $Z^{10}$ and $Z^{11}$ are the same or different and each is fluorine atom or a perfluoroalkyl group having 1 to 20 carbon atoms.

In the structure of the formula (52), examples of the $Z^{11}$ are preferably the same as those of the above-mentioned $Z^{10}$. $Z^{10}$ and $Z^{11}$ may be the same or different.

Also the structure of the formula (52) may be present in the form of a side chain on the aliphatic monocyclic structure constituting the fluorine-containing polymer (A-3) or in the form of a part of the ring structure forming the aliphatic monocyclic structure. At least one OH group may be present in one molecule of the monocyclic structure, and the aliphatic monocyclic structure may have two or more OH groups.

In the fluorine-containing polymer having the structure of the formula (50), (51) or (52), though the ΔH value of the structure may exceed 75 kJ/mol, many structural units having the ΔH value of not more than 75 kJ/mol are contained in the polymer and as a matter of course, the ΔH value of the polymer is preferably not more than 75 kJ/mol, more preferably not more than 70 kJ/mol, particularly preferably not more than 50 kJ/mol.

Example of the preferred structure of the recurring unit of the aliphatic monocyclic structure contained in the fluorine-containing polymer which is used for the photoresist composition of the present invention is the structural unit of the formula (53):

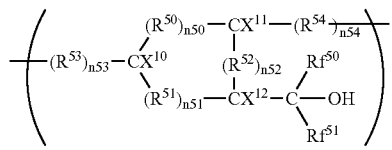
(53)

wherein $Rf^{50}$ and $Rf^{51}$ are the same or different and each is a perfluoroalkyl group having 1 to 20 carbon atoms; $X^{10}$ and $X^{11}$ are the same or different and each is H, F, an alkyl group having 1 to 20 carbon atoms, preferably 1 to 5 carbon atoms or a fluorine-containing alkyl group which has 1 to 20 carbon atoms, preferably 1 to 5 carbon atoms and may have ether bond; $X^{12}$ is hydrogen atom, fluorine atom, an alkyl group having 1 to 20 carbon atoms, a fluorine-containing alkyl group which has 1 to 20 carbon atoms and may have ether bond, OH group or a group represented by the formula:

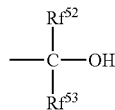

wherein $Rf^{52}$ and $Rf^{53}$ are the same or different and each is a perfluoroalkyl group having 1 to 20 carbon atoms; $R^{50}$ is at least one selected from an alkylene group or fluorine-containing alkylene group which has 1 to 3 carbon atoms and constitutes a ring; $R^{51}$ and $R^{52}$ are the same or different and each is at least one selected from a divalent hydrocarbon group which has 1 to 7 carbon atoms and constitutes a ring, oxygen atom, a divalent hydrocarbon group having ether bond which has the sum of oxygen atoms and carbon atoms of 2 to 7 and constitutes a ring, a divalent fluorine-containing alkylene group which has 1 to 7 carbon atoms and constitutes a ring or a divalent fluorine-containing alkylene group having ether bond which has the sum of oxygen atoms and carbon atoms of 2 to 7 and constitutes a ring; and the sum of carbon atoms constituting a trunk chain in $R^{51}$ and $R^{52}$ is not more than 7, and OH group or a group represented by the formula:

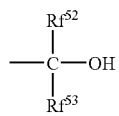

wherein $Rf^{52}$ and $Rf^{53}$ are as defined above, may be bonded to any of carbon atoms in $R^{51}$; $R^{53}$ and $R^{54}$ are the same or different and each is a divalent alkylene group having 1 or 2 carbon atoms or a divalent fluorine-containing alkylene group having 1 or 2 carbon atoms; n50, n51, n52, n53 and n54 are the same or different and each is 0 or 1, or the structural unit represented by the formula (54):

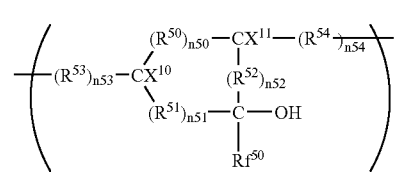
(54)

wherein $Rf^{50}$, $X^{10}$, $X^{11}$, $R^{50}$, $R^{51}$, $R^{52}$, $R^{53}$, $R^{54}$, n50, n51, n52, n53 and n54 are as defined in the above-mentioned formula (53). The fluorine-containing polymer having the structural unit (53) or (54) is referred to as (A-5).

Also it is preferable that the structural unit (53) or (54) contains any of the above-mentioned structures of the formula (50), (51) and (52).

Concretely it is preferable that $X^{12}$ in the formula (53) is $Z^{10}$ in the formula (51), wherein $Z^{10}$ is fluorine atom or a perfluoroalkyl group having 1 to 20 carbon atoms.

It is preferable that at least one $Z^{10}$ of the formula (50), wherein $Z^{10}$ is fluorine atom or a perfluoroalkyl group having 1 to 20 carbon atoms, is bonded to any one of neighboring carbon atoms of the carbon atom bonded to OH group of the formula (54) or it is preferable that one or two of $Z^{10}$ and of $Z^{11}$ of the formula (52), wherein $Z^{10}$ and $Z^{11}$ are the same or different and each is fluorine atom or a perfluoroalkyl group having 1 to 20 carbon atoms, are bonded to both neighboring carbon atoms of the carbon atom bonded to OH group of the formula (54).

Those fluorine-containing polymers having recurring unit of monocyclic structure represented by the formula (53) or (54) are novel substances which have not been disclosed in prior literatures and patent publications. Also the above-mentioned preferred structural units of the formula (53) and (54) are novel substances which have not been disclosed in prior literatures and patent publications.

More concretely examples thereof are those mentioned below, and calculated ΔH values of some of them are also mentioned below.

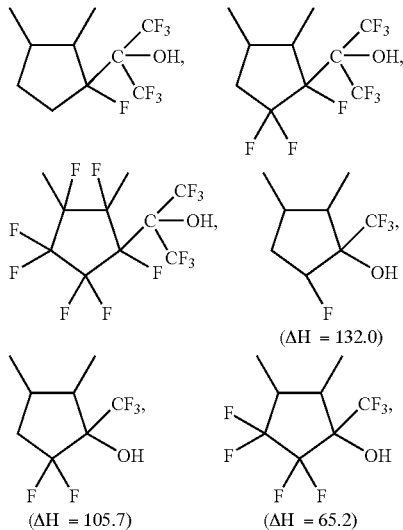

-continued

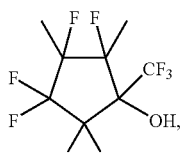 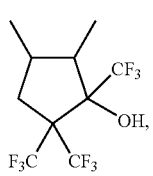

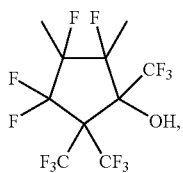 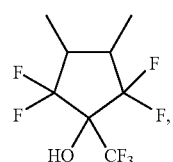

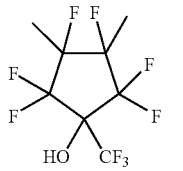 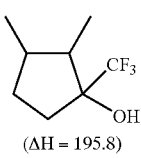

and ($\Delta H = 195.8$)

Also in the photoresist composition of the present invention, two or more OH groups or moieties having OH group may be bonded in the aliphatic monocyclic structure having OH group. For example, preferred is the monocyclic structure of the formula (53), in which a group:

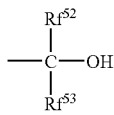

wherein $Rf^{52}$ and $Rf^{53}$ are the same or different and each is a perfluoroalkyl group having 1 to 20 carbon atoms, is bonded instead of $X^{12}$, and/or at least one group:

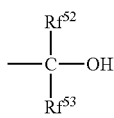

wherein $R^{52}$ and $R^{53}$ are as defined above, is bonded to any of carbon atoms of $R^{51}$ (in case where n51 is 1). Also preferred is the monocyclic structural unit of the formula (54), in which OH group is bonded to any of carbon atoms of $R^{51}$ (in case where n51 is 1) and/or at least one structural unit:

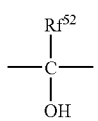

wherein $R^{52}$ is as defined above, is contained in the structure of $R^{51}$ (in case where n51 is 1).

Examples thereof are:

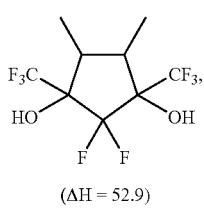 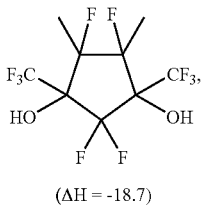

($\Delta H = 52.9$)   ($\Delta H = -18.7$)

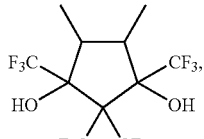 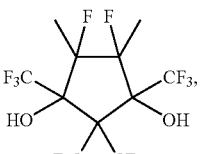

($\Delta H = 24.8$)

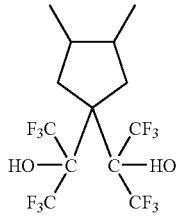

($\Delta H = 3.9$)

and the like. It is preferable that the fluorine-containing polymer has those structural units. The fluorine-containing polymers having recurring units of those monocyclic structures are novel substances which have not been disclosed in any of literatures and patent publications.

Among them, a monomer:

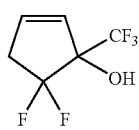

which can introduce a structural unit:

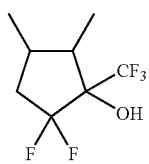

is also a novel compound. Example of a preparation process thereof is as shown in the following preparation scheme (1).

Preparation scheme (1)

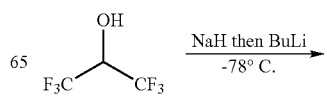

-continued

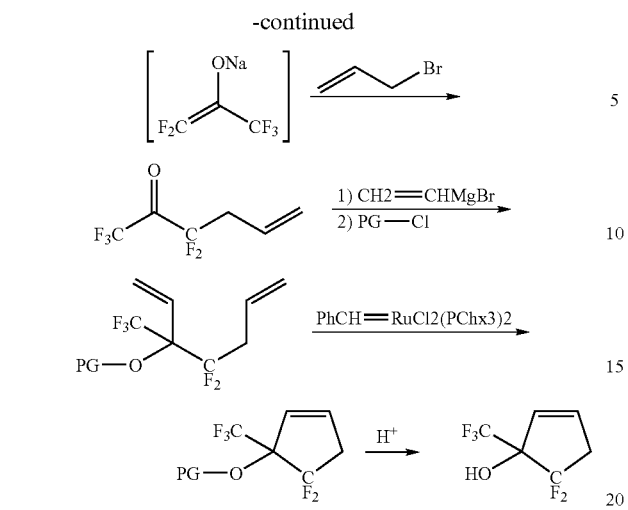

PG——: EtOH₂——
(Protection group)

Also a monomer:

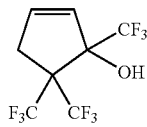

which can introduce a structural unit:

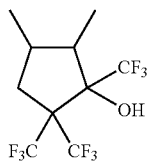

is a novel compound. Example of a preparation process thereof is as shown in the following preparation scheme (2).

Preparation scheme (2)

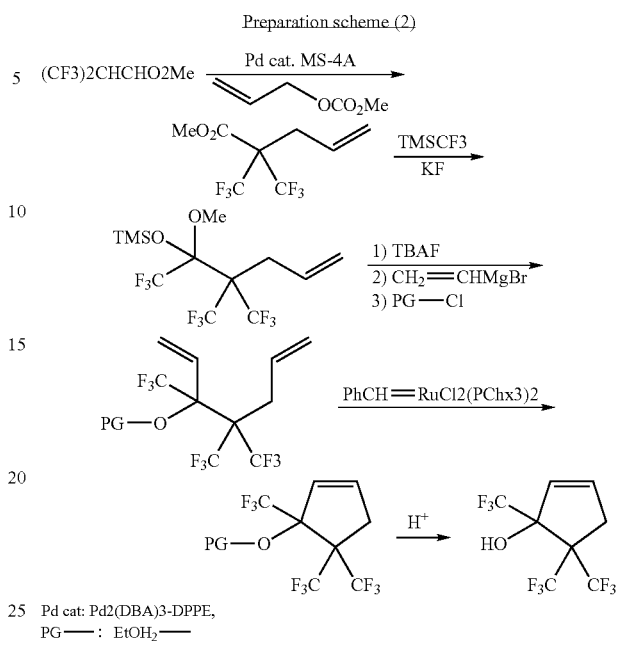

Pd cat: Pd2(DBA)3-DPPE,
PG——: EtOH₂——

Also a monomer:

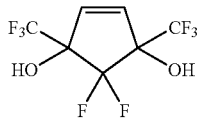

which can introduce a structural unit:

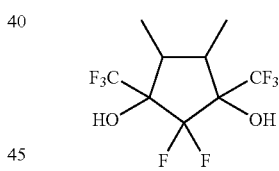

is a novel compound. Example of a preparation process thereof is as shown in the following preparation scheme (3).

Preparation scheme (3)

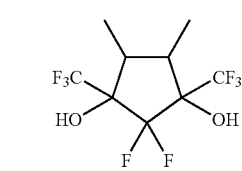

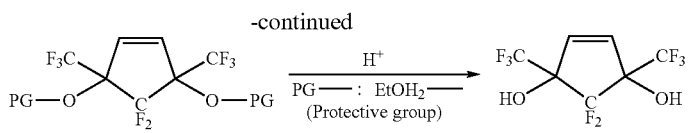

(MEC-31 is a fluorinating agent available from DAIKIN INDUSTRIES, LTD.)

Also a monomer represented by:

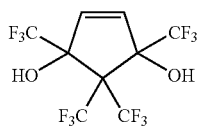

which can introduce a structural unit represented by:

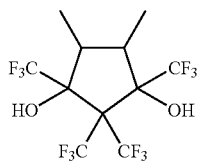

is a novel compound, and example of a preparation process thereof is the following preparation scheme (4).

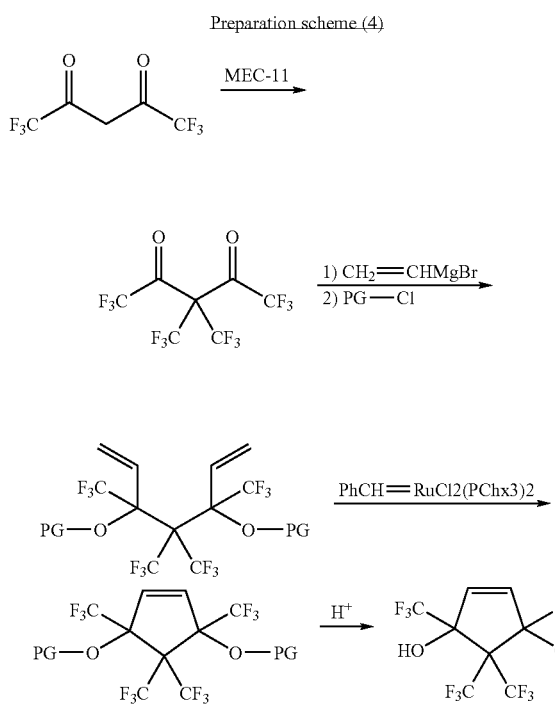

(MEC-11 is a fluorinating agent available from DAIKIN INDUSTRIES, LTD.)

Also a structural unit represented by:

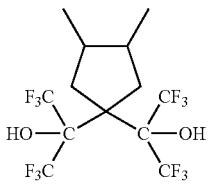

can be obtained by cyclic polymerization of a diene compound represented by:

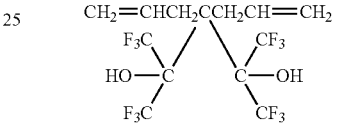

and further can be obtained by (co)polymerization of a novel monomer represented by:

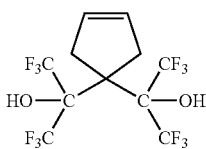

and example of a preparation process thereof is the following preparation scheme (5).

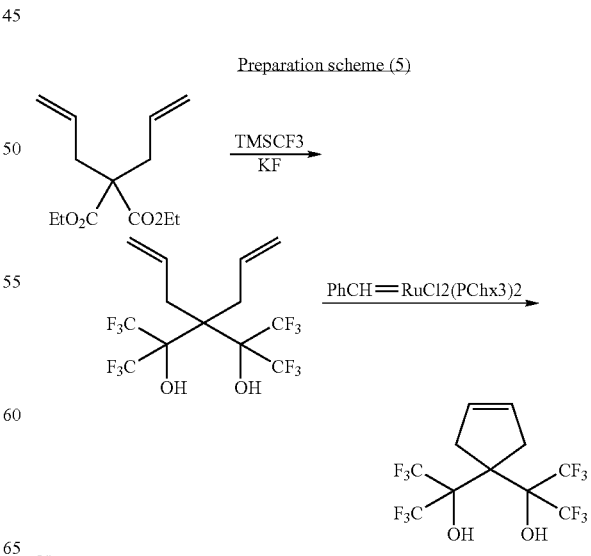

or

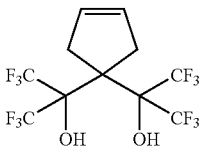

-continued

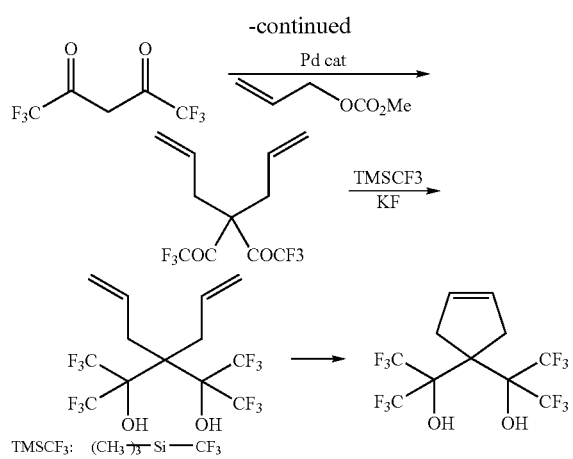

It is preferable that the fluorine-containing polymer having OH group for the photoresist composition of the present invention has at least one of the aliphatic monocyclic structure satisfying the above-mentioned Equation 1, aliphatic monocyclic structures having the structures of the formulae (50) to (52) or the monocyclic structures of the formula (53) to (54) (which are generically referred to as "structural unit M3"). The fluorine-containing polymer is a homopolymer consisting of the structural unit M3 of monocyclic structure having OH group or a copolymer comprising the structural unit M3 and a structural unit copolymerizable therewith (the above-mentioned M1, N, etc.). Concretely it is preferable that the fluorine-containing polymer is a fluorine-containing polymer having a number average molecular weight of from 500 to 1,000,000 which is represented by the formula (60):

-(M3)-(N3)-  (60)

wherein M3 is at least one recurring unit selected from recurring units of the aliphatic monocyclic structure satisfying the above-mentioned Equation1 or 2, aliphatic monocyclic structures having the structures of the formula (50) to (52) or the monocyclic structures of the formula (53) to (54); N3 is a structural unit derived from a monomer copolymerizable with the monomer to introduce the structural unit M3, and the structural units M3 and N3 are contained in amounts of from 0.1 to 100% by mole and from 0 to 99.9% by mole, respectively.

Particularly the fluorine-containing polymer having the recurring unit selected from the monocyclic structures of the formula (53) to (54) is a novel substance which has not been disclosed in literatures and patent publications.

Namely, the novel fluorine-containing polymer of the present invention is a fluorine-containing polymer having a number average molecular weight of from 500 to 1,000,000 which is represented by the formula (61):

-(M3-1)-(N3-1)-  (61)

wherein M3-1 is at least one structural unit selected from the monocyclic structural units of the formulae (53) and (54); N3-1 is a structural unit derived from a monomer copolymerizable with the monomer to introduce the structural unit M3-1, and the structural units M3-1 and N3-1 are contained in amounts of from 0.1 to 100% by mole and from 0 to 99.9% by mole, respectively.

Examples of the structural unit M3-1 of the fluorine-containing polymer of the present invention are the same as those mentioned above as preferred examples of the formulae (53) and (54).

In the formulae (60) and (61), the copolymerizable components N3 and N3-1 are optional components and are not particularly limited as far as they are monomers copolymerizable with the structural units M3 and M3-1. The structural units N3 and N3-1 may be optionally selected depending on required characteristics of intended fluorine-containing polymer.

It is particularly preferable that the structural unit N3 or N3-1 is the structural unit M1 in the above-mentioned novel fluorine-containing polymer (Ma) (the structural unit derived from an ethylenic monomer having 2 or 3 carbon atoms and at least one fluorine atom), and examples thereof are preferably the same as the above-mentioned preferred examples of the structural unit M1. When those structural units are used, a polymer which has excellent transparency and dry etching resistance and is preferred as a photoresist polymer can be obtained.

Examples of the structural unit N3 are preferably the same as the above-mentioned examples of the structural units N and N1 (examples mentioned in (i) and (ii) of the structural unit N and examples of N1) explained in the first of the present invention (fluorine-containing polymer having an aliphatic monocyclic structure in its trunk chain).

In the fluorine-containing polymer of the present invention (fluorine-containing polymer used for a photoresist composition), various combinations and proportions of the structural unit M3 or M3-1 and the structural unit N3 or N3-1 can be selected from the above-mentioned examples depending on intended application, physical properties (particularly glass transition point, hardness, etc.), functions (transparency, refractive index), etc.

One of the fluorine-containing polymers of the present invention (fluorine-containing polymers used for a photoresist composition) contains the structural unit M3 or M3-1 as an essential component and has functions due to the structural unit M3 or M3-1 itself such as maintaining a low refractive index and imparting transparency to the polymer, and functions due to hydroxyl such as imparting solubility in a solvent, solubility in an aqueous alkaline solution (developing solution), adhesion to a substrate and crosslinkability because OH group and fluorine atom can be introduced to the cyclic structural unit. In addition, dry etching resistance also becomes good because of the cyclic structural unit. Therefore even if the fluorine-containing polymer of the present invention contains a larger amount of the structural unit M3 or M3-1 or in the extreme case, even if the polymer consists of the structural unit M3 or M3-1 (100% by mole), transparency and the dry etching resistance can be maintained.

Further in the case of the copolymer of the present invention comprising the structural unit M3 or M3-1 and the structural unit N3 or N3-1 of a copolymerizable monomer, when the structural unit N3 or N3-1 is selected from the above-mentioned examples, a fluorine-containing polymer having a higher glass transition point, a higher transparency (particularly in a vacuum ultraviolet region) and a higher dry etching resistance can be obtained.

In the copolymer comprising the structural unit M3 or M3-1 and the structural unit N3 or N3-1, the proportion of the structural unit M3 or M3-1 may be not less than 0.1% by mole based on the whole monomers constituting the fluorine-containing polymer. In order to impart solubility in an alkaline solution (developing solution) to the fluorine-containing polymer, it is preferable that the structural unit M3 or M3-1 is contained in an amount of not less than10% by mole, preferably not less than 20% by mole, more preferably not less than 30% by mole. An upper limit thereof is (not more than) 100% by mole.

The fluorine-containing polymer of the present invention (fluorine-containing polymer used for a photoresist composition) is preferable particularly for the resist application since transparency and dry etching resistance are not lowered even if the proportion of the structural unit M3 or M3-1 is increased.

Also in the case of the above-mentioned application requiring transparency, preferred combinations and proportions of the structural unit M3 or M3-1 and the structural unit N3 or N3-1 are those which can make the fluorine-containing polymer non-crystalline.

The molecular weight of the fluorine-containing polymer of the present invention (fluorine-containing polymer used for a photoresist composition) can be selected, for example, within a range of from 500 to 1,000,000 in number average molecular weight. Preferred molecular weight is from 1,000 to 500,000, particularly from 2,000 to 200,000.

When the molecular weight is too low, mechanical properties easily become insufficient, and the resist film is apt to be insufficient in strength. If the molecular weight is too high, solubility in a solvent is lowered, and film forming property and leveling property are easily lowered particularly at forming a thin coating film. For coating applications, most preferable number average molecular weight is selected within a range of from 5,000 to 100,000.

With respect to transparency, it is preferable that the polymer is transparent in the case of vacuum ultraviolet light having a wavelength of not more than 200 nm. For example, an absorption coefficient at 157 nm is not more than 3.0 $\mu m^{-1}$, preferably not more than 2.0 $\mu m^{-1}$, particularly preferably not more than 1.0 $\mu m^{-1}$. Such a fluorine-containing polymer is preferable as a base polymer for a $F_2$ resist.

Also it is preferable that the fluorine-containing polymer is soluble in general-purpose solvents, for example, in at least one of ketone solvents, acetic acid ester solvents, alcohol solvents, aromatic solvents, glycol ether solvents or glycol ester solvents or in a solvent mixture containing at least one of the above-mentioned general-purpose solvents.

The fluorine-containing polymer of the present invention (fluorine-containing polymer used for a photoresist composition) can be obtained by polymerizing a monomer capable of introducing the structural unit M3 or M3-1, for example, an unsaturated compound containing an aliphatic monocyclic structure having OH group, by cyclic (co)polymerization of an ethylenic diene monomer having OH group or by (co)polymerizing, through known method, a monomer capable of introducing the structural unit M3 or M3-1 and a monomer which is a copolymerizable component as the structural unit N3 or N3-1. For the polymerization, radical polymerization method, anion polymerization method, cation polymerization method and the like can be employed. Among them, the radical polymerization method is preferably used from the point that each monomer exemplified to obtain the fluorine-containing polymer having OH group of the present invention has good radial polymerizability, control of composition and molecular weight is easy and production in an industrial scale is easy.

In order to initiate the radical polymerization, means for initiation is not limited particularly as far as the polymerization proceeds radically. The polymerization is initiated, for example, with an organic or inorganic radical polymerization initiator, heat, light, ionizing radiation or the like.

The polymerization can be carried out by solution polymerization, bulk polymerization, suspension polymerization, emulsion polymerization or the like. The molecular weight is controlled by the contents of monomers to be used for the polymerization, the content of polymerization initiator, the content of chain transfer agent, temperature, etc. The components of the copolymer can be controlled by the starting monomer components.

Further in the fluorine-containing polymer which is used for the photoresist composition of the present invention, a part or the whole of OH groups may be protected by a protective group which can undergo conversion to OH group by reaction with an acid. The protective group undergoes conversion to OH group by an acid generated from a photoacid generator and thereby the polymer can work as a positive type resist.

Namely, the present invention relates to the photoresist composition which comprises:

(A-4) a fluorine-containing polymer having functional group protected by a protective group which can convert the functional group to OH group by reaction with an acid, (B) a photoacid generator and (C) a solvent, in which the fluorine-containing polymer (A-4) is a fluorine-containing polymer having functional group comprising OH group contained in the recurring unit of aliphatic monocyclic structure of any of the above-mentioned fluorine-containing polymers (A-2), (A-3) and (A-5) and the protective group protecting the OH group.

Examples of the preferred acid-labile group which is used as a protective group are groups represented by:

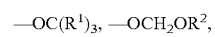

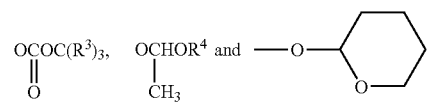

wherein $R^1$, $R^2$, $R^3$ and $R^4$ are the same or different and each is an alkyl group having 1 to 5 carbon atoms.

More concretely there are preferably:

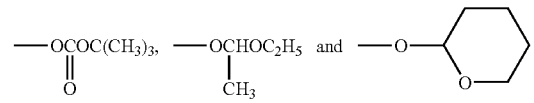

and from the viewpoint of good acid-reactivity, preferred are —$OC(CH_3)_3$,

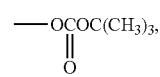

—$OCH_2OCH_3$ and —$OCH_2OC_2H_5$ and from the viewpoint of good transparency, preferred are —$OC(CH_3)_3$, —$OCH_2OCH_3$ and —$OCH_2OC_2H_5$.

The fluorine-containing polymer having only OH group can be used as a negative type resist in combination with a known crosslinking agent.

Also in the case of use for a positive type resist, when OH is present together with another acid-labile group, for example, a functional group which is converted to COOH group due to action of an acid, solubility in a developing solution and a dissolving rate can be adjusted and resolution can be enhanced.

Also the introduction of OH group and COOH group to the fluorine-containing polymer is preferred since adhesion to a substrate can be improved.

In the photoresist composition of the present invention (preferably a chemically amplifying photoresist composition), the photoacid generator (B) is a compound which generates acid or cation by irradiating the photoacid generator itself or the photoresist composition containing the photoacid generator with radiation. The photoacid generators can be used in a mixture of two or more thereof.

Examples of the photoacid generator (B) are, for instance, known compounds such as an organic halogen compound, sulfonic acid ester, onium salt, diazonium salt, disulfone compound and a mixture thereof.

Examples thereof are, for instance, haloalkyl group-containing s-triazine derivatives such as tris(trichloromethyl)-s-triazine, tris(tribromomethyl)-s-triazine, tris(dibromomethyl)-s-triazine and 2,4-bis(tribromomethyl)-6-p-methoxyphenyl-s-triazine, halogen-substituted paraffin hydrocarbons such as 1,2,3,4-tetrabromobutane, 1,1,2,2-tetrabromoethane, carbon tetrabromide and iodoform, halogen-substituted cycloparaffin hydrocarbons such as hexabromocyclohexane, hexachlorocyclohexane and hexabromocyclododecane, haloalkyl group-containing benzene derivatives such as bis(trichloromethyl)benzene and bis(tribromomethyl)benzene, haloalkyl group-containing sulfone compounds such as tribromomethylphenyl sulfone and trichloromethylphenyl sulfone, halogen-containing sulfolane compounds such as 2,3-dibromosulfolane, haloalkyl group-containing isocyanurates such as tris(2,3-dibromopropyl)isocyanurate, sulfonium salts such as triphenylsulfonium chloride, triphenylsulfoniummethane sulfonate, triphenylsulfoniumtrifluoromethane sulfonate, triphenylsulfonium-p-toluene sulfonate, triphenylsulfoniumtetrafluoro borate, triphenylsulfoniumhexafluoro arcenate and triphenylsulfoniumhexafluoro phosphonate, iodonium salts such as diphenyl-iodonium-trifluoromethane-sulfonate, diphenyl-iodonium-p-toluene-sulfonate, diphenyliodonium tetrafluoroborate, diphenyliodonium hexafluoroarcenate and diphenyliodonium hexafluorophosphonate, sulfonic acid esters such as methyl p-toluenesulfonate, ethyl p-toluenesulfonate, butyl p-toluenesulfonate, phenyl p-toluenesulfonate, 1,2,3-tris(p-toluenesulfonyloxy)benzene, p-toluenesulfonic acid benzoin ester, methyl methanesulfonate, ethyl methanesulfonate, butyl methanesulfonate, 1,2,3-tris(methanesulfonyloxy)benzene, phenyl methanesulfonate, methane sulfonic acid benzoin ester, methyl trifluoromethanesulfonate, ethyl trifluoromethanesulfonate, butyl trifluoromethanesulfonate, 1,2,3-tris(trifluoromethanesulfonyloxy)benzene, phenyl trifluoromethanesulfonate and benzoin trifluoromethanesulfonate, disulfones such as diphenyldisulfone, sulfonediazides such as bis(phenylsulfonyl)diazomethane, bis(2,4-dimethylphenylsulfonyl)diazomethane, bis(cyclohexylsulfonyl)diazomethane, cyclohexylsulfonyl-(2-methoxyphenylsulfonyl)diazomethane, cyclohexylsulfonyl-(3-methoxyphenylsulfonyl)diazomethane, cyclohexylsulfonyl-(4-methoxyphenylsulfonyl)diazomehtane, cyclopentylsulfonyl-(2-methoxyphenylsulfonyl)diazomethane, cyclopentylsulfonyl-(3-methoxyphenylsulfonyl)diazomethane, cyclopentylsulfonyl-(4-methoxyphenylsulfonyl)diazomethane, cyclohexylsulfonyl-(2-fluorophenylsulfonyl)diazomethane, cyclohexylsulfonyl-(3-fluorophenylsulfonyl)diazomethane, cyclohexylsulfonyl-(4-fluorophenylsulfonyl)diazomethane, cyclopentylsulfonyl-(2-fluorophenylsulfonyl)diazomethane, cyclopentylsulfonyl-(3-fluorophenylsulfonyl)diazomethane, cyclopentylsulfonyl-(4-fluorophenylsulfonyl)diazomethane, cyclohexylsulfonyl-(2-chlorophenylsulfonyl)diazomethane, cyclohexylsulfonyl-(3-chlorophenylsulfonyl)diazomethane, cyclohexylsulfonyl-(4-chlorophenylsulfonyl)diazomethane, cyclopentylsulfonyl-(2-chlorophenylsulfonyl)diazomethane, cyclopentylsulfonyl-(3-chlorophenylsulfonyl)diazomethane, cyclopentylsulfonyl-(4-chlorophenylsulfonyl)diazomethane, cyclohexylsulfonyl-(2-trifluoromethyphenylsulfonyl)diazomethane, cyclohexylsulfonyl-(3-trifluoromethylphenylsulfonyl)diazomethane, cyclohexylsulfonyl-(4-trifluoromethylphenylsulfonyl)diazomethane, cyclopentylsulfonyl-(2-trifluoromethylphenylsulfonyl)diazomethane, cyclopentylsulfonyl-(3-trifluoromethylphenylsulfonyl)diazomethane, cyclopentylsulfonyl-(4-trifluoromethylphenylsulfonyl)diazomethane, cyclohexylsulfonyl-(2-trifluoromethoxyphenylsulfonyl)diazomethane, cyclohexylsulfonyl-(3-trifluoromethoxyphenylsulfonyl)diazomethane, cyclohexylsulfonyl-(4-trifluoromethoxyphenylsulfonyl)diazomethane, cyclopentylsulfonyl-(2-trifluoromethoxyphenylsulfonyl)diazomethane, cyclopentylsulfonyl-(3-trifluoromethoxyphenylsulfonyl)diazomethane, cyclopentylsulfonyl-(4-trifluoromethoxyphenylsulfonyl)diazomethane, cyclohexylsulfonyl-(2,4,6-trimethylphenylsulfonyl)diazomethane, cyclohexylsulfonyl-(2,3,4-trimethylphenylsulfonyl)diazomethane, cyclohexylsulfonyl-(2,4,6-triethylphenylsulfonyl)diazomethane, cyclohexylsulfonyl-(2,3,4-triethylphenylsulfonyl)diazomethane, cyclopentylsulfonyl-(2,4,6-trimethylphenylsulfonyl)diazomethane, cyclopentylsulfonyl-(2,3,4-trimethylphenylsulfonyl)diazomethane, cyclopentylsulfonyl-(2,4,6-triethylphenylsulfonyl)diazomethane, cyclopentylsulfonyl-(2,3,4-triethylphenylsulfonyl)diazomethane, phenylsulfonyl-(2-methoxylphenylsulfonyl)diazomethane, phenylsulfonyl-(3-methoxylphenylsulfonyl)diazomethane, phenylsulfonyl-(4-methoxylphenylsulfonyl)diazomethane, bis(2-methoxylphenylsulfonyl)diazomethane, bis(3-methoxylphenylsulfonyl)diazomethane, bis(4-methoxylphenylsulfonyl)diazomethane, phenylsulfonyl-(2,4,6-trimethylphenylsulfonyl)diazomethane, phenylsulfonyl-(2,3,4-trimethylphenylsulfonyl)diazomethane, phenylsulfonyl-(2,4,6-triethylphenylsulfonyl)diazomethane, phenylsulfonyl-(2,3,4-triethylphenylsulfonyl)diazomethane, 2,4-dimethylphenylsulfonyl-(2,4,6-trimethylphenylsulfonyl)diazomethane, 2,4-dimethylphenylsulfonyl-(2,3,4-trimethylphenylsulfonyl)diazomethane, phenylsulfonyl-(2-fluorophenylsulfonyl)diazomethane, phenylsulfonyl-(3-fluorophenylsulfonyl)diazomethane and phenylsulfonyl-(4-fluorophenylsulfonyl)diazomethane, o-nitrobenzyl esters such as o-nitrobenzyl-p-toluenesulfonate, sulfone hydrazides such as N,N'-di(phenylsulfonyl)hydrazide and the like.

Examples of the preferable photoacid generator are compounds generating any of sulfonic acid, sulfenic acid or sulfinic acid. Examples thereof are onium sulfonates such as triphenylsulfonium-p-toluenesulfonate and diphenyliodonium-p-toluenesulfonate, sulfonic acid esters such as phenyl p-toluenesulfonate and 1,2,3-tris(p-toluenesulfonyloxy)benzene, disulfones such as diphenyldisulfone, sulfonediazides such as bis(phenylsulfonyl)diazomethane, bis(2,4-dimethylphenylsulfonyl)diazomethane, bis(cyclohexylsulfonyl)diazomethane, cyclohexylsulfonyl-(2-methoxyphenylsulfonyl)diazomethane, cyclohexylsulfonyl-(3-methoxyphenylsulfonyl)diazomethane, cyclohexylsulfonyl-(4-methoxyphenylsulfonyl)diazomehtane, cyclopentylsulfonyl-(2-methoxyphenylsulfonyl)diazomethane, cyclopentylsulfonyl-(3-methoxyphenylsulfonyl)diazomethane, cyclopentylsulfonyl-(4-methoxyphenylsulfonyl)diazomethane, cyclohexylsulfonyl-(2-fluorophenylsulfonyl)diazomethane, cyclohexylsulfonyl-(3-fluorophenylsulfonyl)diazomethane, cyclohexylsulfonyl-(4-fluorophenylsulfonyl)diazomethane, cyclopentylsulfonyl-(2-fluorophenylsulfonyl)diazomethane, cyclopentylsulfonyl-(3-fluorophenylsulfonyl)diazomethane, cyclopentylsulfonyl-(4-fluorophenylsulfonyl)diazomethane, cyclohexylsulfonyl-(2-chlorophenylsulfonyl)diazomethane, cyclohexylsulfonyl-(3-chlorophenylsulfonyl)diazomethane, cyclohexylsulfonyl-(4-chlorophenylsulfonyl)diazomethane, cyclopentylsulfonyl-(2-chlorophenylsulfonyl)diazomethane, cyclopentylsulfonyl-(3-chlorophenylsulfonyl)diazomethane, cyclopentylsulfonyl-(4-chlorophenylsulfonyl)diazomethane, cyclohexylsulfonyl-(2-trifluoromethylphenylsulfonyl)diazomethane, cyclohexylsulfonyl-(3-trifluoromethylphenylsulfonyl)diazomethane, cyclohexylsulfonyl-(4-trifluoromethylphenylsulfonyl)diazomethane, cyclopentylsulfonyl-(2-trifluoromethylphenylsulfonyl)diazomethane, cyclopentylsulfonyl-(3-trifluoromethylphenylsulfonyl)diazomethane, cyclopentylsulfonyl-(4-trifluoromethylphenylsulfonyl)diazomethane, cyclohexylsulfonyl-(2-trifluoromethoxyphenylsulfonyl)diazomethane, cyclohexylsulfonyl-(3-trifluoromethoxyphenylsulfonyl)diazomethane, cyclohexylsulfonyl-(4-trifluoromethoxyphenylsulfonyl)diazomethane, cyclopentylsulfonyl-(2-trifluoromethoxyphenylsulfonyl)diazomethane, cyclopentylsulfonyl-(3-trifluoromethoxyphenylsulfonyl)diazomethane, cyclopentylsulfonyl-(4-trifluoromethoxyphenylsulfonyl)diazomethane, cyclohexylsulfonyl-(2,4,6-trimethylphenylsulfonyl)diazomethane, cyclohexylsulfonyl-(2,3,4-trimethylphenylsulfonyl)diazomethane, cyclohexylsulfonyl-(2,4,6-triethylphenylsulfonyl)diazomethane, cyclohexylsulfonyl-(2,3,4-triethylphenylsulfonyl)diazomethane, cyclopentylsulfonyl-(2,4,6-trimethylphenylsulfonyl)diazomethane, cyclopentylsulfonyl-(2,3,4-trimethylphenylsulfonyl)diazomethane, cyclopentylsulfonyl-(2,4,6-triethylphenylsulfonyl)diazomethane, cyclopentylsulfonyl-(2,3,4-triethylphenylsulfonyl)diazomethane, phenylsulfonyl-(2-methoxylphenylsulfonyl)diazomethane, phenylsulfonyl-(3-methoxylphenylsulfonyl)diazomethane, phenylsulfonyl-(4-methoxylphenylsulfonyl)diazomethane, bis(2-methoxylphenylsulfonyl)diazomethane, bis(3-methoxylphenylsulfonyl)diazomethane, bis(4-methoxylphenylsulfonyl)diazomethane, phenylsulfonyl-(2,4,6-trimethylphenylsulfonyl)diazomethane, phenylsulfonyl-(2,3,4-trimethylphenylsulfonyl)diazomethane, phenylsulfonyl-(2,4,6-triethylphenylsulfonyl)diazomethane, phenylsulfonyl-(2,3,4-triethylphenylsulfonyl)diazomethane, 2,4-dimethylphenylsulfonyl-(2,4,6-trimethylphenylsulfonyl)diazomethane, 2,4-dimethylphenylsulfonyl-(2,3,4-trimethylphenylsulfonyl)diazomethane, phenylsulfonyl-(2-fluorophenylsulfonyl)diazomethane, phenylsulfonyl-(3-fluorophenylsulfonyl)diazomethane and phenylsulfonyl-(4-fluorophenylsulfonyl)diazomethane, o-nitrobenzyl esters such as o-nitrobenzyl-p-toluenesulfonate, and the like. Particularly sulfonediazides are preferable.

Further in addition to the above-mentioned examples, a photoacid generator of onium salts having fluorine atom can be used. For example, there are preferably used a fluoroalkyl onium salt represented by the formula:

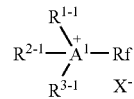

wherein $A^1$ is an element selected from iodine, sulfur, selenium, tellurium, nitrogen and phosphorus;

when $A^1$ is iodine, $R^{2-1}$ and $R^{3-1}$ are not present and $R^{1-1}$ is an alkyl group having 1 to 15 carbon atoms or an aryl group having 6 to 15 carbon atoms;

when $A^1$ is sulfur, selenium or tellurium, $R^{3-1}$ is not present and $R^{1-1}$ and $R^{2-1}$ are independently an alkyl group having 1 to 15 carbon atoms, an aryl group having 6 to 20 carbon atoms, a dialkylamino group having 2 to 30 carbon atoms, an alkylarylamino group having 7 to 35 carbon atoms or a diarylamino group having 12 to 40 carbon atoms and $R^{1-1}$ and $R^{2-1}$ may be bonded to each other to constitute a ring;

when $A^1$ is nitrogen or phosphorus, $R^{1-1}$, $R^{2-1}$ and $R^{3-1}$ are independently an alkyl group having 1 to 15 carbon atoms, an aryl group having 6 to 20 carbon atoms, a dialkylamino group having 2 to 30 carbon atoms, an alkylarylamino group having 7 to 35 carbon atoms or a diarylamino group having 12 to 40 carbon atoms and $R^{1-1}$, $R^{2-1}$ and $R^{3-1}$ may be bonded to each other to form one or more rings, or $R^{3-1}$ may not be present and $R^{1-1}$ and $R^{2-1}$ may be bonded to each other to constitute an aromatic ring including $A^1$;

the above-mentioned alkyl group, an alkyl group of the dialkylamino group and an alkyl group of the alkylarylamino group may be substituted with an aryl group, halogen atom, oxygen atom, nitrogen atom, sulfur atom or silicon atom, may be branched or may constitute a ring, and the above-mentioned aryl group, an aryl group of the alkylarylamino group and an aryl group of the diarylamino group may be substituted with an alkyl group, haloalkyl group, halogen atom, alkoxyl group, aryloxy group, nitro group, amide group, cyano group, alkanoyl group, aroyl group, alkoxycarbonyl group, aryloxycarbonyl group or acyloxy group;

$R_f$ is a perfluoroalkyl group having 1 to 15 carbon atoms which may be branched or may constitute a ring, or is the perfluoroalkyl group in which a part of its fluorine atoms is substituted with hydrogen atoms;

$X^-$ is a conjugated base of Brønsted acid, or a fluoroalkyl onium salt represented by the formula:

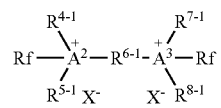

wherein $A^2$ and $A^3$ are the same or different and each is an element selected from iodine, sulfur, selenium, tellurium, nitrogen and phosphorus;

when $A^2$ or $A^3$ is iodine, $R^{4-1}$, $R^{5-1}$, $R^{7-1}$ and $R^{8-1}$ are not present;

when $A^2$ or $A^3$ is sulfur, selenium or tellurium, $R^{5-1}$ and $R^{8-1}$ are not present and $R^{4-1}$ and $R^{7-1}$ are independently an alkyl group having 1 to 15 carbon atoms, an aryl group having 6 to 20 carbon atoms, a dialkylamino group having 2 to 30 carbon atoms, an alkylarylamino group having 7 to 35 carbon atoms or a diarylamino group having 12 to 40 carbon atoms;

when $A^2$ or $A^3$ is nitrogen or phosphorus, $R^{4-1}$, $R^{5-1}$, $R^{7-1}$ and $R^{8-1}$ are independently an alkyl group having 1 to 15 carbon atoms, an aryl group having 6 to 20 carbon atoms, a dialkylamino group having 2 to 30 carbon atoms, an alkylarylamino group having 7 to 35 carbon atoms or a diarylamino group having 12 to 40 carbon atoms, and $R^{4-1}$ and $R^{5-1}$ or $R^{7-1}$ and $R^{8-1}$ may be bonded to each other, respectively to constitute a ring;

the above-mentioned alkyl group, an alkyl group of the dialkylamino group and an alkyl group of the alkylarylamino group may be substituted with an aryl group, halogen atom, oxygen atom, nitrogen atom, sulfur atom or silicon atom, may be branched or may constitute a ring, and the above-mentioned aryl group, an aryl group of the alkylarylamino group and an aryl group of the diarylamino group may be substituted with an alkyl group, haloalkyl group, halogen atom, alkoxyl group, aryloxy group, nitro group, amide group, cyano group, alkanoyl group, aroyl group, alkoxycarbonyl group, aryloxycarbonyl group or acyloxy group;

$R^{6-1}$ is an alkylene group having 1 to 15 carbon atoms which may be substituted with an aryl group, halogen atom, oxygen atom, nitrogen atom, sulfur atom or silicon atom, may be branched or may constitute a ring;

$R^f$ is a perfluoroalkyl group having 1 to 15 carbon atoms which may be branched or may constitute a ring, or is the perfluoroalkyl group in which a part of its fluorine atoms is substituted with hydrogen atoms;

$X^-$ is a conjugated base of Brφnsted acid and the like.

Examples thereof are fluoroalkyl onium salts having iodine atom as its center element:

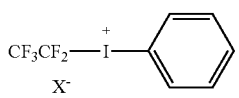
(I-1)

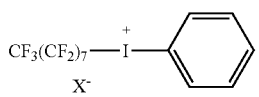
(I-2)

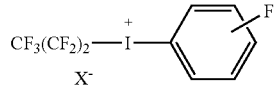
(I-3)

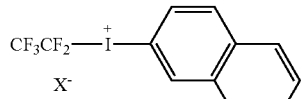
(I-4)

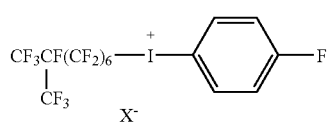
(I-5)

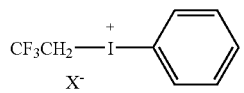
(I-6)

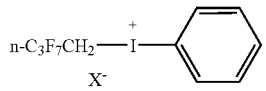
(I-7)

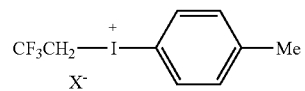
(I-8)

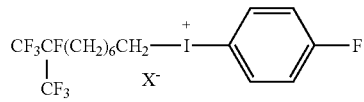
(I-9)

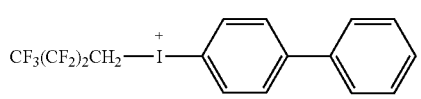
(I-10)

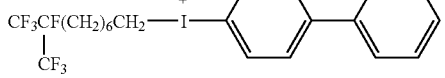
(I-11)

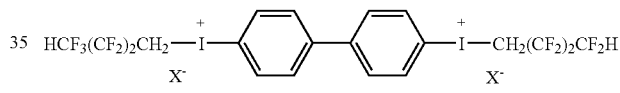
(I-12)

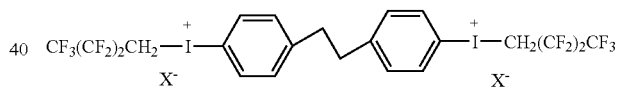
(I-13)

Fluoroalkyl onium salt having sulfur atom as its center element:

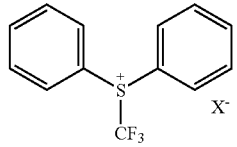
(S-1)

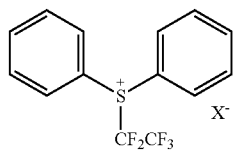
(S-2)

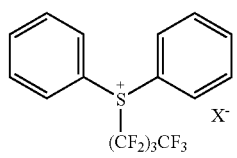
(S-3)

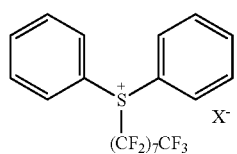
(S-4)
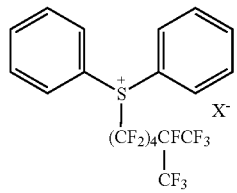
(S-5)
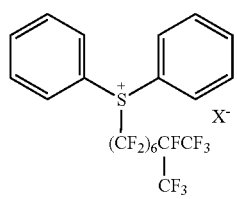
(S-6)
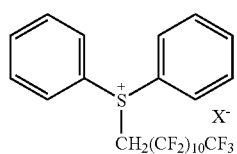
(S-7)
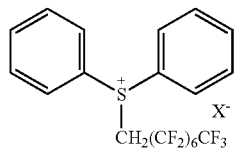
(S-8)
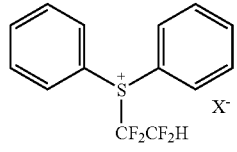
(S-9)
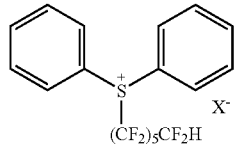
(S-10)
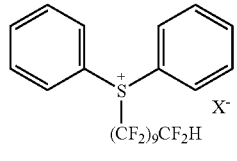
(S-11)
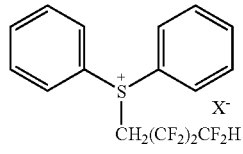
(S-12)
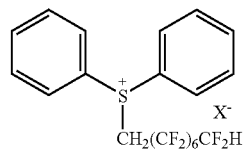
(S-13)
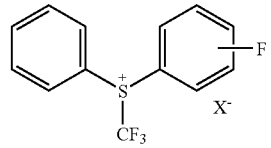
(S-14)
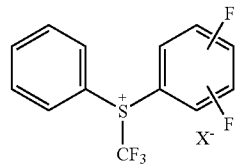
(S-15)
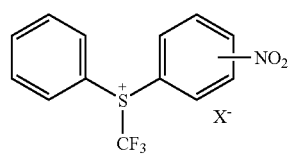
(S-16)
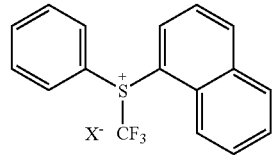
(S-17)
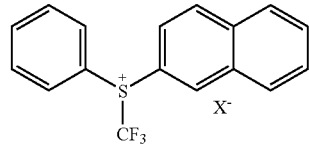
(S-18)
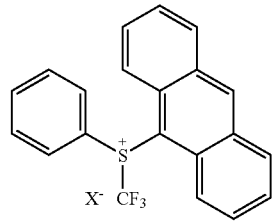
(S-19)
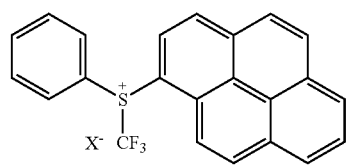
(S-20)
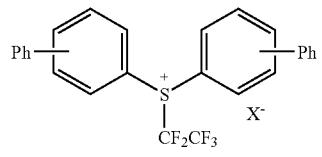
(S-21)

-continued
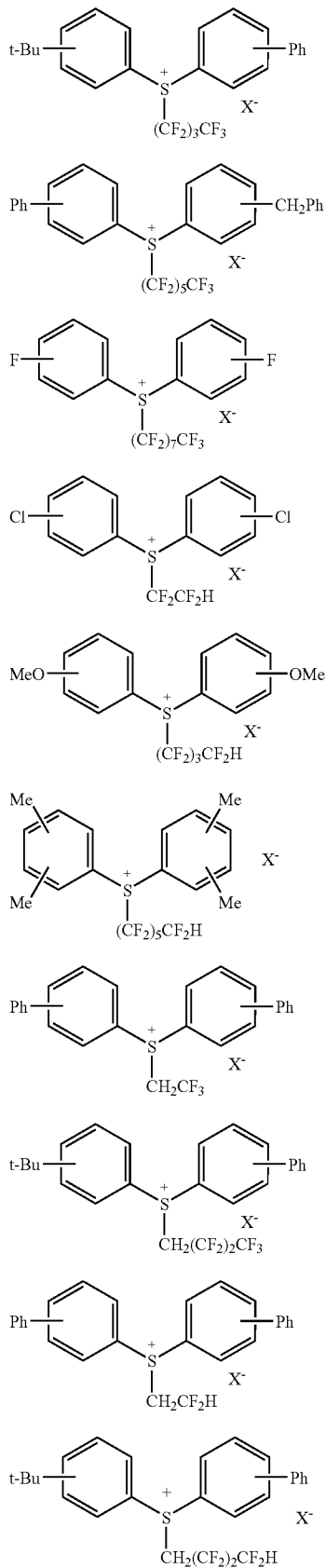
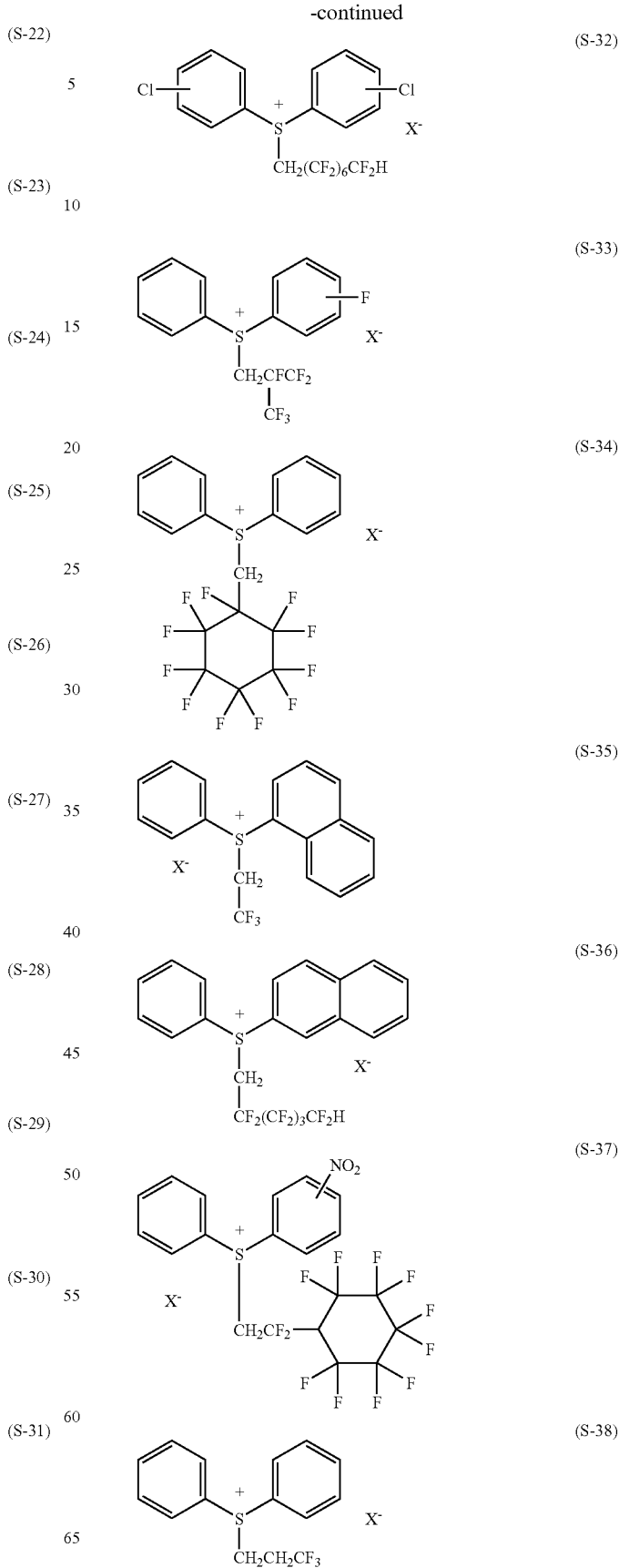

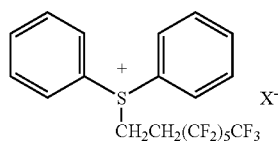 (S-39)
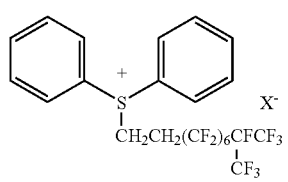 (S-40)
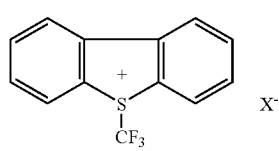 (S-41)
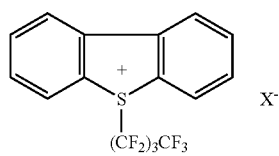 (S-42)
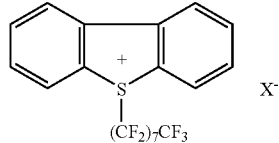 (S-43)
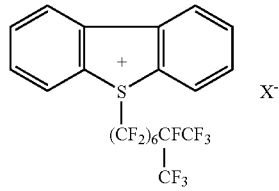 (S-44)
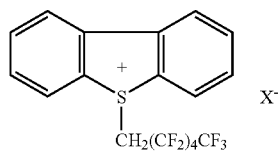 (S-45)
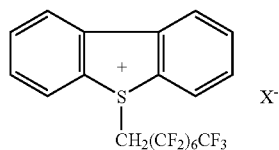 (S-46)
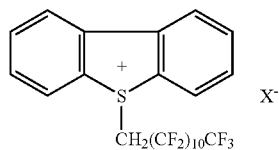 (S-47)
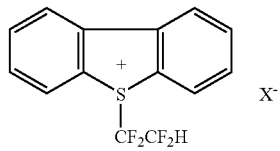 (S-48)
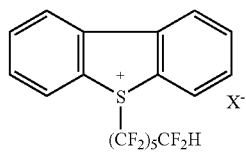 (S-49)
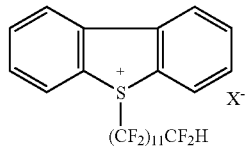 (S-50)
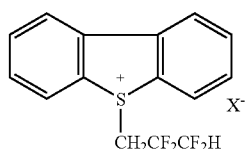 (S-51)
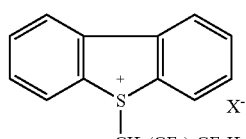 (S-52)
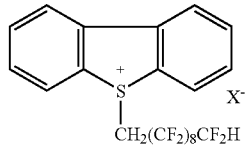 (S-53)
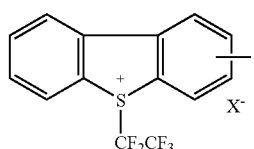 (S-54)
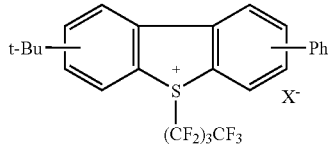 (S-55)
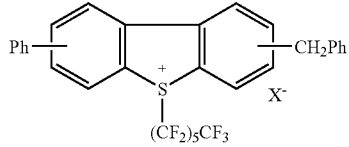 (S-56)
(S-57)

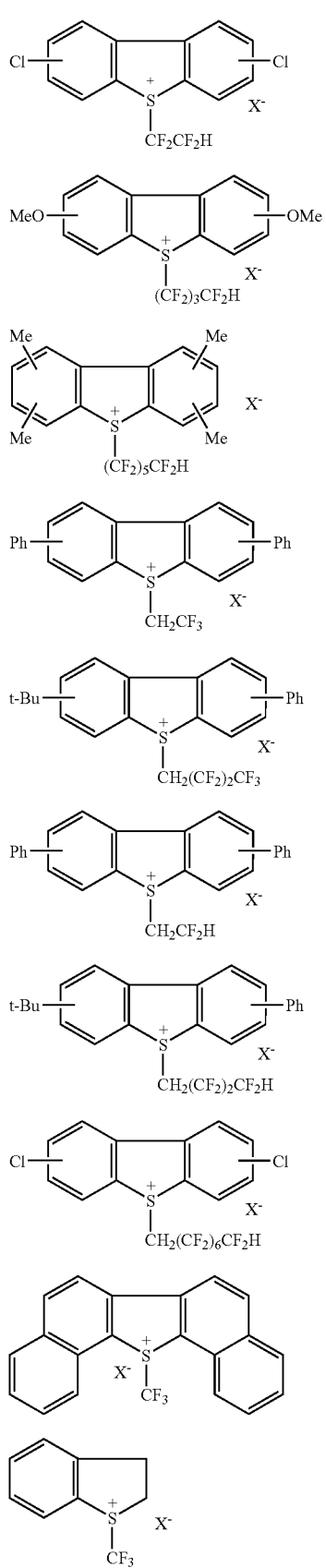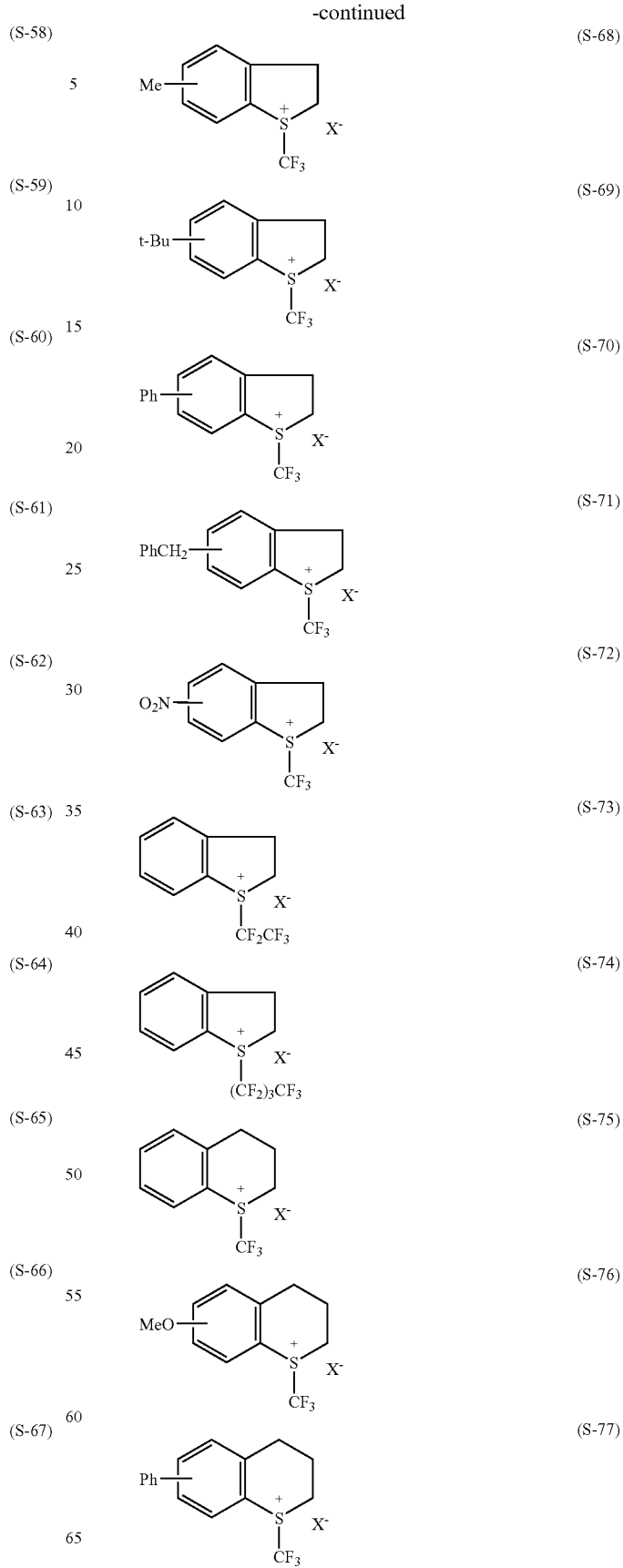

-continued
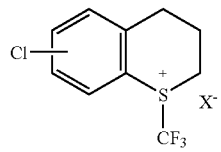 (S-78)
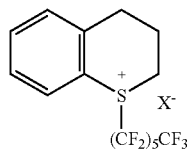 (S-79)
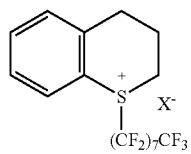 (S-80)
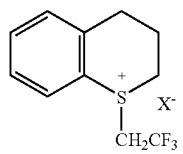 (S-81)
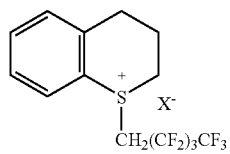 (S-82)
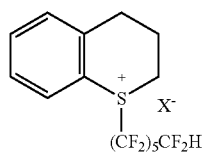 (S-83)
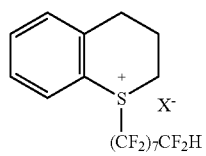 (S-84)
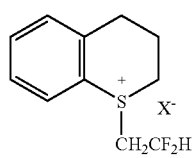 (S-85)
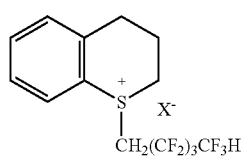 (S-86)
-continued
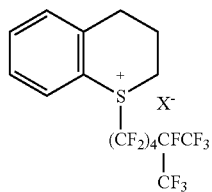 (S-87)
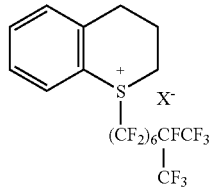 (S-88)
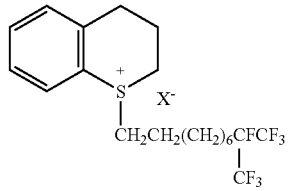 (S-89)
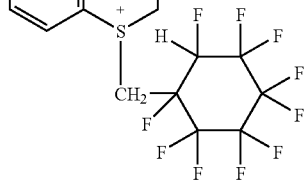 (S-90)
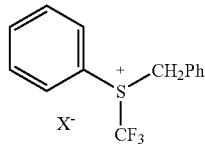 (S-91)
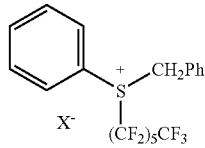 (S-92)
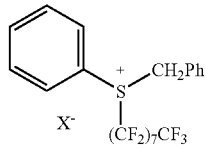 (S-93)
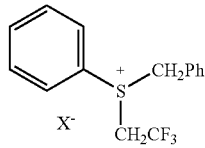 (S-94)

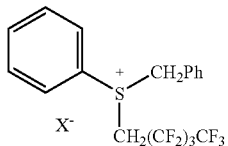 (S-95)
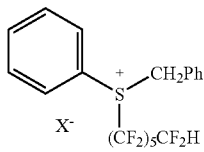 (S-96)
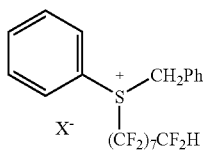 (S-97)
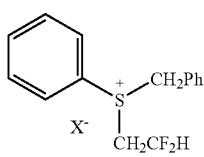 (S-98)
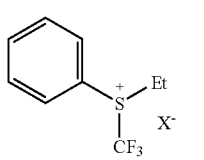 (S-99)
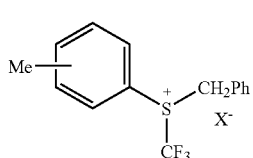 (S-100)
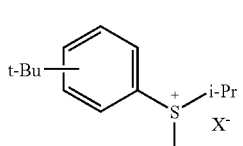 (S-101)
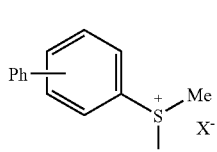 (S-102)
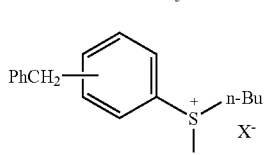 (S-103)
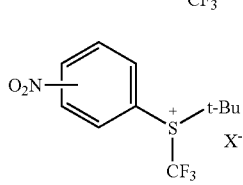 (S-104)
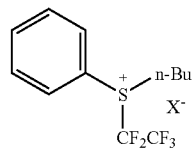 (S-105)
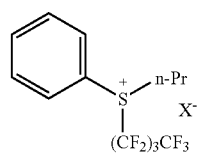 (S-106)
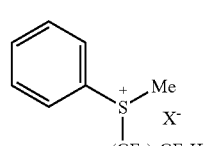 (S-107)
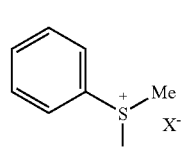 (S-108)
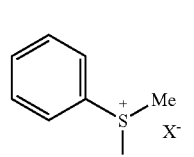 (S-109)
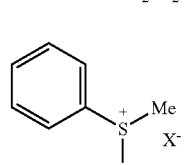 (S-110)
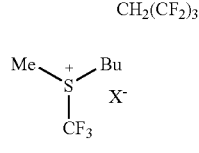 (S-111)
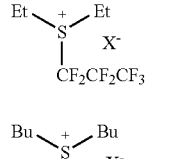 (S-112)
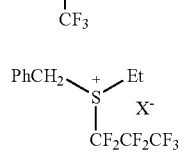 (S-113)
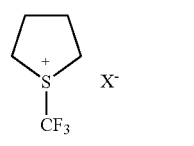 (S-114)
(S-115)

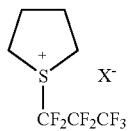 (S-116)
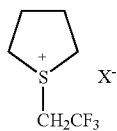 (S-117)
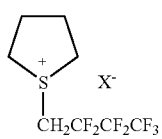 (S-118)
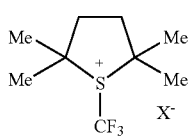 (S-119)
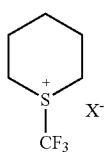 (S-120)
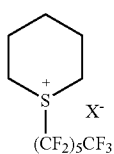 (S-121)
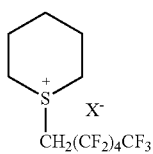 (S-122)
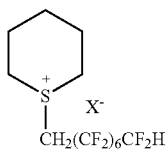 (S-123)
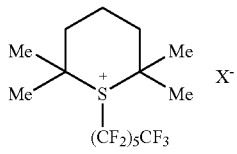 (S-124)
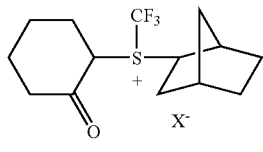 (S-125)
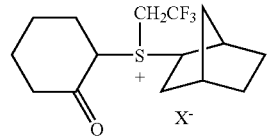 (S-126)
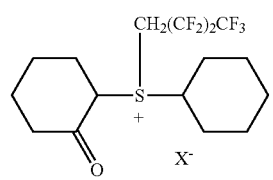 (S-127)
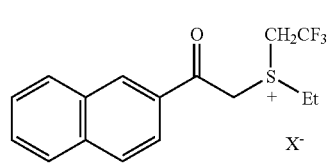 (S-128)
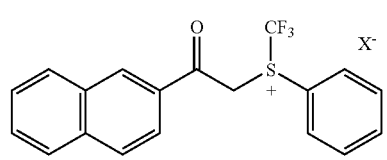 (S-129)
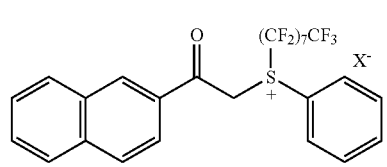 (S-130)
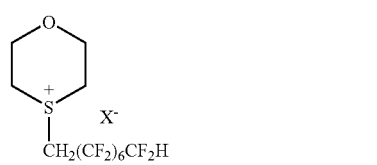 (S-131)
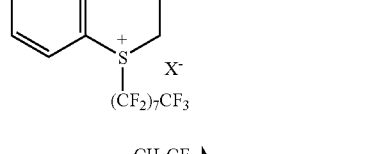 (S-132)
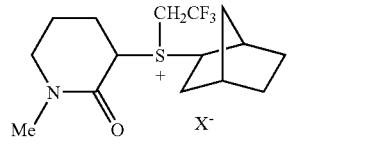 (S-133)
(S-134)

-continued
(S-135)
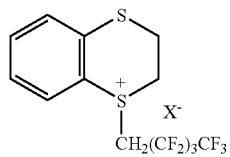
(S-136)
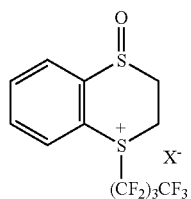
(S-137)
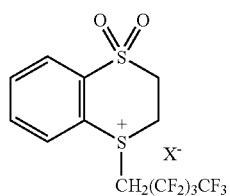
(S-138)
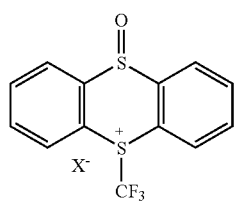
(S-139)
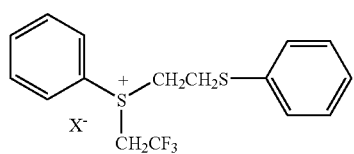
(S-140)
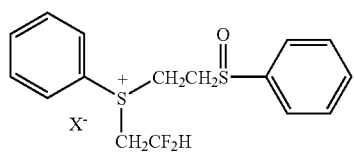
(S-141)
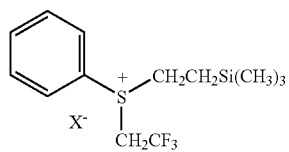
(S-142)
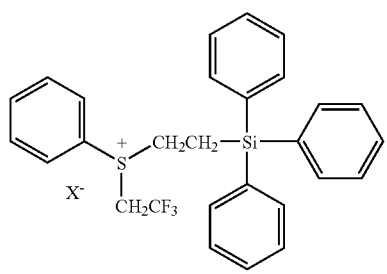
-continued
(S-143)
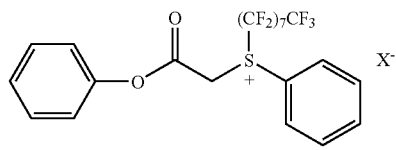
(S-144)
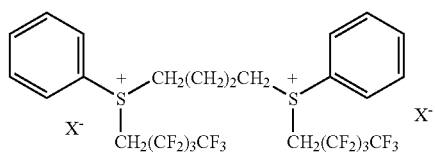
(S-145)
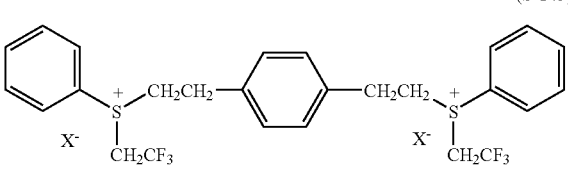
Flouroalkyl onium salt having selenium atom as its center element:
(Se-1)
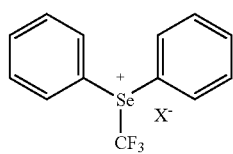
(Se-2)
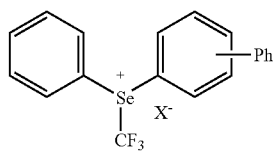
(Se-3)
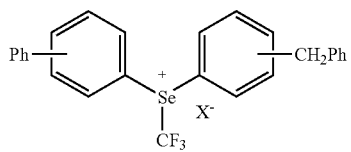
(Se-4)
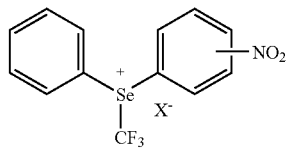
(Se-5)
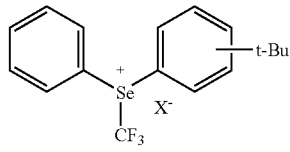
(Se-6)
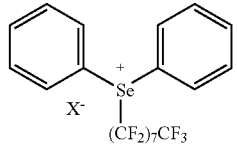

-continued
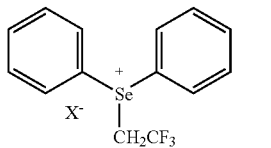 (Se-7)
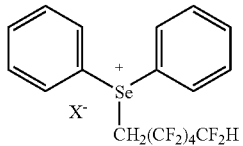 (Se-8)
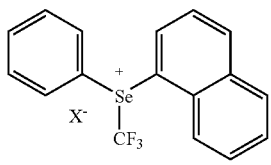 (Se-9)
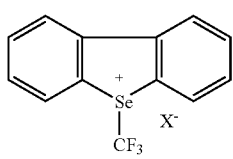 (Se-10)
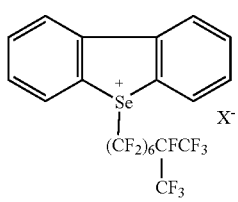 (Se-11)
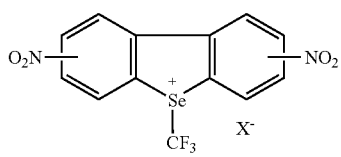 (Se-12)
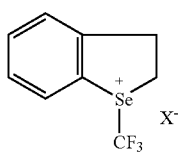 (Se-13)
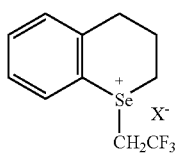 (Se-14)
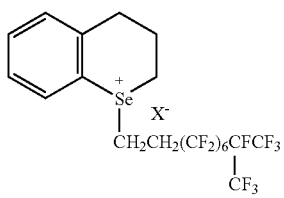 (Se-15)
-continued
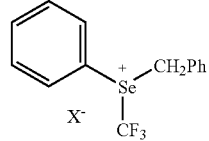 (Se-16)
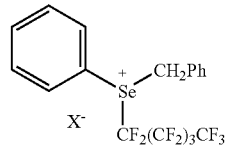 (Se-17)
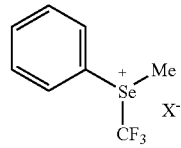 (Se-18)
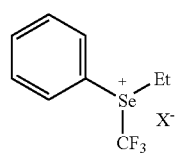 (Se-19)
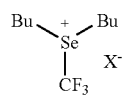 (Se-20)
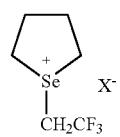 (Se-21)
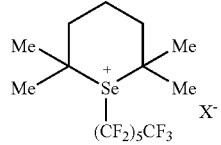 (Se-22)
Fluoroalkyl onium salt having tellurium atom as its center element:
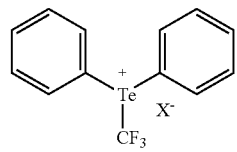 (Te-1)
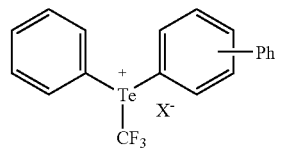 (Te-2)

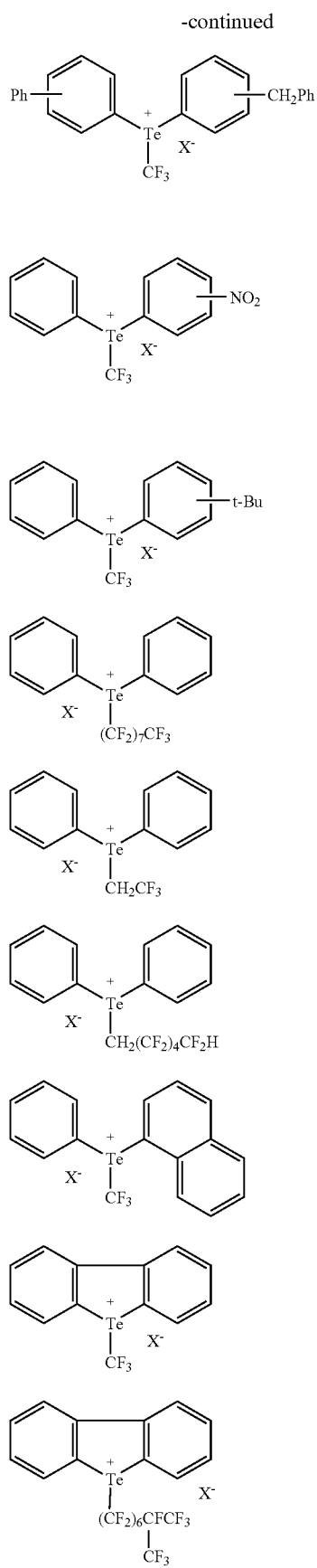

-continued
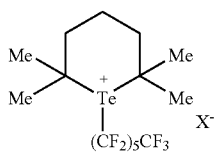 (Te-22)
Fluoroalkyl onium salt having nitrogen atom as its center element:
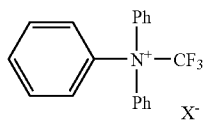 (N-1)
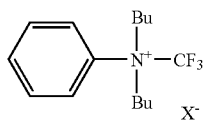 (N-2)
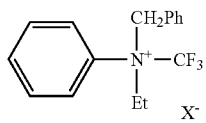 (N-3)
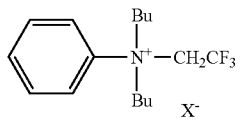 (N-4)
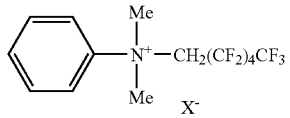 (N-5)
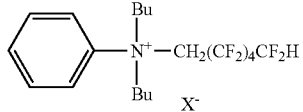 (N-6)
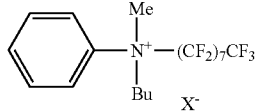 (N-7)
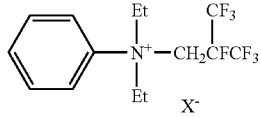 (N-8)
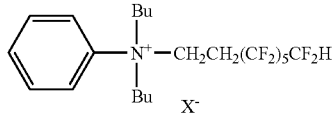 (N-9)
-continued
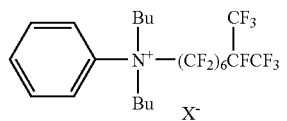 (N-10)
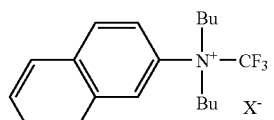 (N-11)
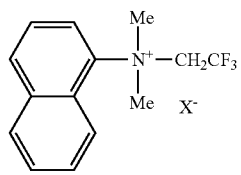 (N-12)
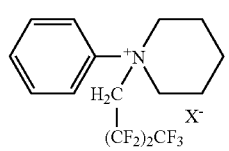 (N-13)
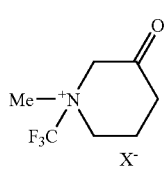 (N-14)
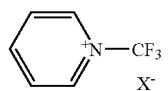 (N-15)
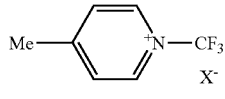 (N-16)
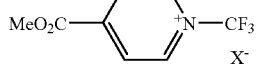 (N-17)
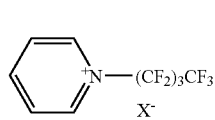 (N-18)
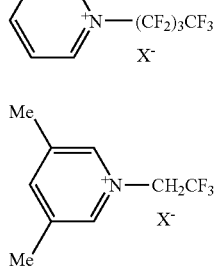 (N-19)
(N-20)

-continued
(N-21) 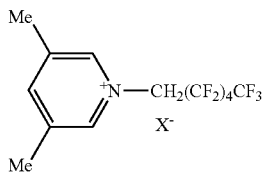
(N-22) 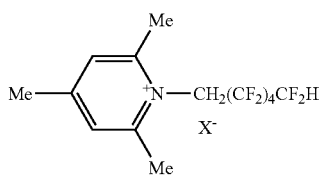
(N-23) 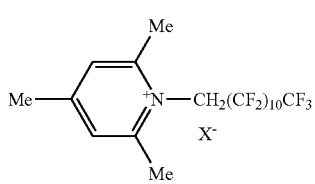
(N-24) 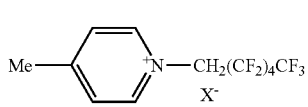
Fluoroalkyl onium salt having phosphorus atom as its center element:
(P-1) 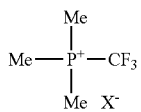
(P-2) 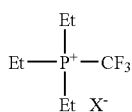
(P-3) 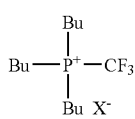
(P-4) 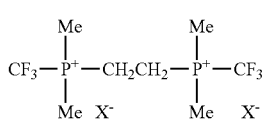
(P-5) 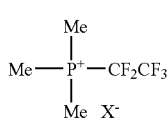
(P-6) 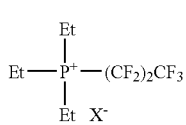
-continued
(P-7) 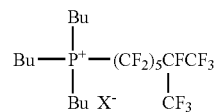
(P-8) 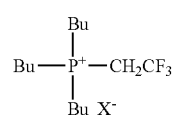
(P-9) 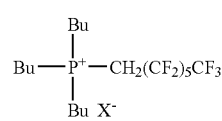
(P-10) 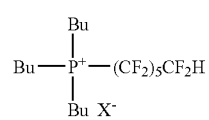
(P-11) 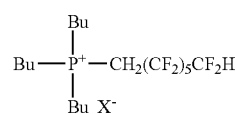
(P-12) 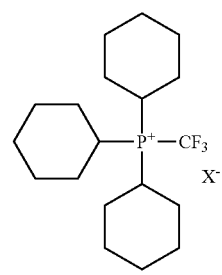
(P-13) 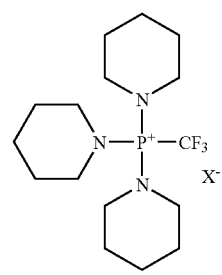
(P-14) 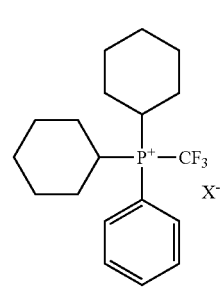

-continued
(P-15)
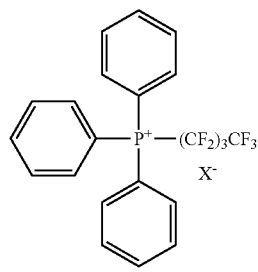
(P-16)
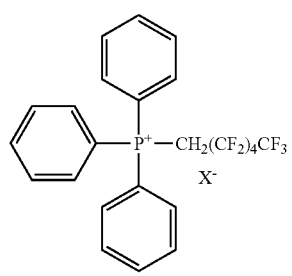
(P-17)
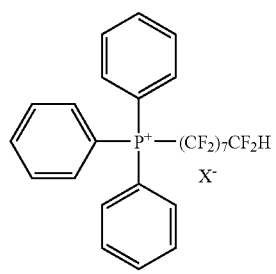
(P-18)
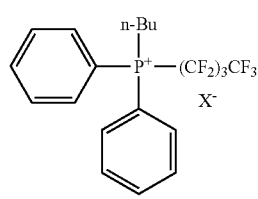
(P-19)
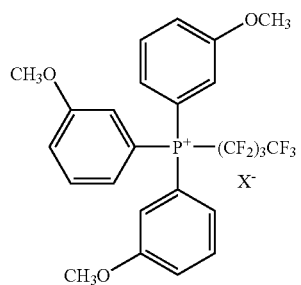
(P-20)
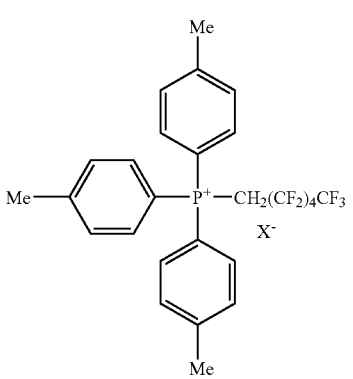
(P-21)
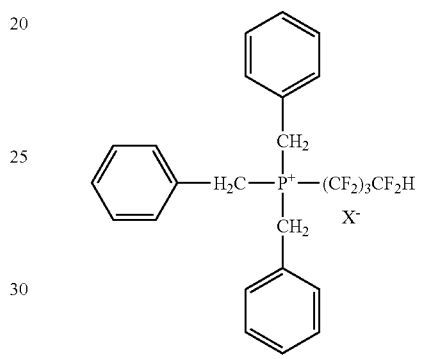
(P-22)
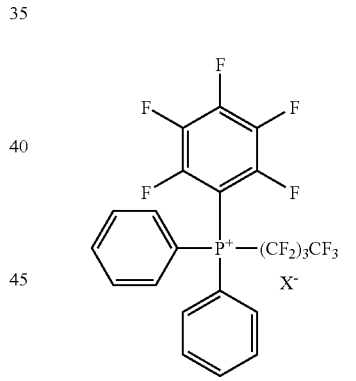
(P-23)
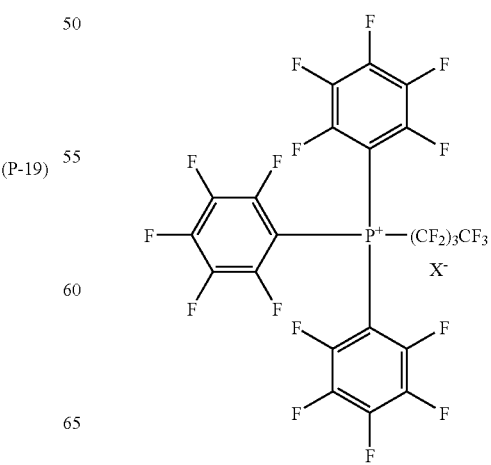

-continued

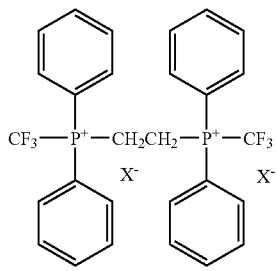
(P-24)

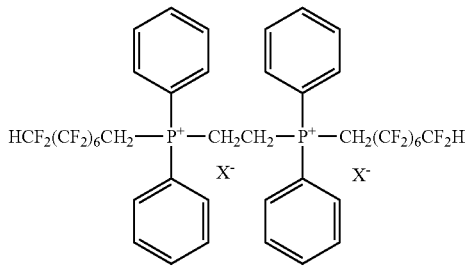
(P-25)

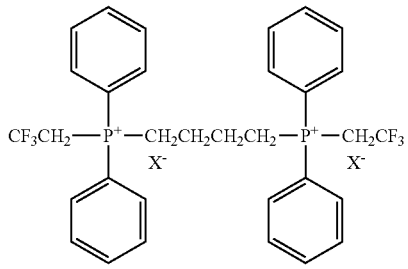
(P-26)

X⁻ in those exemplified fluoroalkyl onium salts is a conjugated base of Brønsted acid. Non-restricted examples of the Brønsted acid are fluoroalkylsulfonic acids such as trifluoromethanesulfonic acid, tetrafluoroethanesulfonic acid, perfluorobutanesulfonic acid, perfluoropentanesulfonic acid, perfluorohexanesulfonic acid, perfluorooctanesulfonic acid and difluoromethanesulfonic acid, methanesulfonic acid, trichloromethanesulfonic acid, benzenesulfonic acid, toluenesulfonic acid, sulfuric acid, fluorosulfonic acid, chlorosulfonic acid, $HBF_4$, $HSbF_6$, $HPF_6$, $HSbCl_5F$, $HSbCl_6$, $HAsF_6$, $HBCl_3F$, $HalCl_4$ and the like. Particularly fluoroalkylsulfonic acids which are strong acids are preferred because neither hydrogen fluoride nor hydrogen chloride is generated.

Those onium salts having a fluorine-containing alkyl group are preferred because transparency thereof is high in a vacuum ultraviolet region and also because of good compatibility with the fluorine-containing polymer having an acid-reactive group in the chemically amplifying photoresist composition of the present invention.

The content of photoacid generator in the photoresist composition of the present invention (chemically amplifying photoresist composition) is preferably from 0.1 to 30 parts by weight, more preferably from 0.2 to 20 parts by weight, most preferably from 0.5 to 10 parts by weight based on 100 parts by weight of the fluorine-containing polymer having an acid-reactive group.

When the content of photoacid generator is less than 0.1 part by weight, sensitivity is lowered, and when the content is more than 30 parts by weight, an amount of light absorbed by the photoacid generator is increased and light does not reach a substrate sufficiently, thereby lowering resolution easily.

Also to the photoresist composition of the present invention may be added an organic base which can act, as a base, on an acid generated from the above-mentioned photoacid generator.

The purpose of adding the organic base is to prevent migration of the acid generated from the photoacid generator and to prevent a resist pattern from undergoing a dimensional change during an interval between the exposure and the PEB treatment. Therefore the organic base is not limited particularly as far as it is a compound being capable of neutralizing the acid generated from the photoacid generator as mentioned above. The organic base is preferred because when an inorganic compound is used as a base, a very small amount of its residue remains after forming a pattern and eliminating the resist and has an adverse effect on the pattern formation. The organic base is an organic amine compound selected from nitrogen-containing compounds. Examples thereof are pyrimidine compounds such as pyrimidine, 2-aminopyrimidine, 4-aminopyrimidine, 5-aminopyrimidine, 2,4-diaminopyrimidine, 2,5-diaminopyrimidine, 4,5-diaminopyrimidine, 4,6-diaminopyrimidine, 2,4,5-triaminopyrimidine, 2,4,6-triaminopyrimidine, 4,5,6-triaminopyrimidine, 2,4,5,6-tetraaminopyrimidine, 2-hydroxypyrimidine, 4-hydroxypyrimidine, 5-hydroxypyrimidine, 2,4-dihydroxypyrimidine, 2,5-dihydroxypyrimidine, 4,5-dihydroxypyrimidine, 4,6-dihydroxypyrimidine, 2,4,5-trihydroxypyrimidine, 2,4,6-trihydroxypyrimidine, 4,5,6-trihydroxypyrimidine, 2,4,5,6-tetrahydroxypyrimidine, 2-amino-4-hydroxypyrimidine, 2-amino-5-hydroxypyrimidine, 2-amino-4,5-dihydroxypyrimidine, 2-amino-4,6-dihydroxypyrimidine, 4-amino-2,5-dihydroxypyrimidine, 4-amino-2,6-dihydroxypyrimidine, 2-amino-4-methylpyrimidine, 2-amino-5-methylpyrimidine, 2-amino-4,5-dimethylpyrimidine, 2-amino-4,6-dimethylpyrimidine, 4-amino-2,5-dimethylpyrimidine, 4-amino-2,6-dimethylpyrimidine, 2-amino-4-methoxypyrimidine, 2-amino-5-methoxypyrimidine, 2-amino-4,5-dimethoxypyrimidine, 2-amino-4,6-dimethoxypyrimidine, 4-amino-2,5-dimethoxypyrimidine, 4-amino-2,6-dimethoxypyrimidine, 2-hydroxy-4-methylpyrimidine, 2-hydroxy-5-methylpyrimidine, 2-hydroxy-4,5-dimethylpyrimidine, 2-hydroxy-4,6-dimethylpyrimidine, 4-hydroxy-2,5-dimethylpyrimidine, 4-hydroxy-2,6-dimethylpyrimidine, 2-hydroxy-4-methoxypyrimidine, 2-hydroxy-5-methoxypyrimidine, 2-hydroxy-4,5-dimethoxypyrimidine, 2-hydroxy-4,6-dimethoxypyrimidine, 4-hydroxy-2,5-dimethoxypyrimidine and 4-hydroxy-2,6-dimethoxypyrimidine, pyridine compounds such as pyridine, 4-dimethylaminopyridine and 2,6-dimethylpyridine, amines substituted with hydroxyalkyl group and having not less than 1 and not more than 4 carbon atoms such as diethanolamine, triethanolamine, triisopropanolamine, tris(hydroxymethyl)aminomethane and bis(2-hydroxyethyl) iminotris(hydroxymethyl)methane, aminophenols such as 2-aminophenol, 3-aminophenol and 4-aminophenol and the like. Preferable organic bases are pyrimidines, pyridines or amines having hydroxyl group, and particularly preferred are amines having hydroxyl group. Those organic bases may be used alone or in a mixture of two or more thereof. The content of organic base in the photoresist composition of the present invention is preferably from 0.1 to 100% by mole, more preferably from 1 to 50% by mole based on the content of photoacid generator. When the content of organic base is less than 0.1% by mole, resolution is lowered, and when the content of organic base is more than 100% by mole, sensitivity tends to be lowered.

In the photoresist composition of the present invention (chemically amplifying photoresist composition), when a negative resist composition is prepared using the fluorine-containing polymer, a crosslinking agent may be used as case demands as mentioned above.

The crosslinking agent is not limited particularly and can be optionally selected from crosslinking agents which have been usually used for negative resists.

Examples of preferable crosslinking agent are, for instance, N-methylol melamine, N-alkoxymethylol melamine compounds, urea compounds, epoxy compounds, isocyanate compounds and the like.

Those crosslinking agents may be used alone or in a combination of two or more thereof. Among them, a combination of the melamine resin and the urea resin is advantageous.

The content of crosslinking agent in the photoresist (particularly negative type) composition of the present invention is from 3 to 70 parts by weight, preferably from 5 to 50 parts by weight, more preferably from 10 to 40 parts by weight based on 100 parts by weight of the fluorine-containing polymer. When the content is less than 3 parts by weight, a resist pattern is difficult to be formed, and the content of more than 70 parts by weight is not preferable because light transmittance is lowered, resolution is easily lowered and developing property is lowered.

The photoresist composition of the present invention may contain, as case demands, various additives which have been usually used in this field, such as dissolution inhibitor, sensitizer, dye, adhesion betterment material and water storage material. While the presence of water is necessary for generating an acid in a chemically amplifying resist, the acid can be generated effectively in the presence of a small amount of water storage material such as polypropylene glycol.

When those additives are used, a total amount thereof is up to about 20% by weight based on the weight of the whole solids in the composition.

In the photoresist composition of the present invention (chemically amplifying photoresist composition), the solvent (C) is one which is capable of dissolving the fluorine-containing polymer, the photoacid generator (B) and the above-exemplified various additives. The solvent is not limited particularly as far as good coatability (surface smoothness, uniformity of coating thickness, etc.) can be obtained.

Examples of the preferable solvent (C) are, for instance, cellosolve solvents such as methyl cellosolve, ethyl cellosolve, methyl cellosolve acetate and ethyl cellosolve acetate, ester solvents such as diethyl oxalate, ethyl pyruvate, ethyl-2-hydroxybutyrate, ethyl acetoacetate, butyl acetate, amyl acetate, ethyl butyrate, butyl butyrate, methyl lactate, ethyl lactate, methyl 3-methoxypropionate, ethyl 3-methoxypropionate, methyl 2-hydroxyisobutyrate and ethyl 2-hydroxyisobutyrate, propylene glycol solvents such as propylene glycol monomethyl ether, propylene glycol monoethyl ether, propylene glycol monobutyl ether, propylene glycol monomethyl ether acetate, propylene glycol monoethyl ether acetate, propylene glycol monobutyl ether acetate and dipropylene glycol dimethyl ether, ketone solvents such as 2-hexanone, cyclohexanone, methyl amino ketone and 2-heptanone, aromatic hydrocarbons such as toluene, xylene, chlorobenzene and chlorotoluene, a solvent mixture of two or more thereof and the like.

Also in order to enhance solubility of the fluorine-containing polymer, a fluorine-containing solvent may be used as case demands.

Examples thereof are, for instance, $CH_3CCl_2F$ (HCFC-141b), a mixture of $CF_3CF_2CHCl_2$ and $CClF_2CF_2CHClF$ (HCFC-225), perfluorohexane, perfluoro(2-butyltetrahydrofuran), methoxy-nonafluorobutane, 1,3-bistrifluoromethylbenzene, and in addition, fluorine-containing alcohols such as:

$H(CF_2CF_2)_nCH_2OH$ (n: an integer of from 1 to 3), $F(CF_2)_nCH_2OH$ (n: an integer of from 1 to 5) and $(CF_3)_2CHOH$, benzotrifluoride, perfluorobenzene, perfluoro(tributylamine), $ClCF_2CFClCF_2CFCl_2$ and the like.

Those fluorine-containing solvents may be used alone, in a mixture of two or more thereof or in a mixture of one or more of the fluorine-containing solvents and non-fluorine-containing solvents.

The amount of the solvent (C) is selected depending on kind of solids to be dissolved, kind of a substrate to be coated, an intended coating thickness, etc. From the viewpoint of easiness of coating, it is preferable that the solvent is used in such an amount that the concentration of the whole solids of the resist composition becomes from 0.5 to 70% by weight, preferably from 1 to 50% by weight, particularly preferably from 5 to 30% by weight.

The photoresist composition of the present invention (chemically amplifying resist composition) is subjected to resist pattern formation according to conventional photoresist technology. In order to form a pattern properly, first, a solution of the resist composition is applied on a substrate such as a silicon wafer by a spinner or the like, and is dried to form a photosensitive layer. A pattern is drawn by irradiating the layer with ultraviolet ray, deep-UV, excimer laser or X-ray by a reduction projection exposure system, etc. through a proper mask pattern or the pattern is drawn with an electron beam, and then heating follows. The layer is then subjected to developing treatment with a developing solution, for example, an aqueous alkaline solution such as an aqueous solution of 1 to 10% by weight of tetramethylammonium hydroxide. Thus an image faithful to the mask pattern can be obtained by the above-mentioned pattern forming method.

It was found that by using the photoresist composition of the present invention (chemically amplifying resist composition), a resist film (photosensitive layer) having a high transparency even in a vacuum ultraviolet region could be formed. Therefore the resist composition of the present invention can be preferably used particularly for a photolithography process using a $F_2$ laser (wavelength of 157 nm) which is under development aiming at a technology node of 0.1 µm.

The tenth of the present invention relates to a fluorine-containing cyclopentene having OH group which is represented by the formula (70):

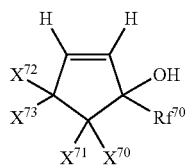

(70)

wherein $Rf^{70}$ is a perfluoroalkyl group having 1 to 20 carbon atoms; $X^{70}$ is fluorine atom or a perfluoroalkyl group having 1 to 20 carbon atoms; $X^{71}$ is hydrogen atom, fluorine atom, a hydrocarbon group having 1 to 20 carbon atoms or a perfluoroalkyl group having 1 to 20 carbon atoms; $X^{72}$ is hydrogen atom, fluorine atom, OH group, a hydrocarbon group having 1 to 20 carbon atoms or a perfluoroalkyl group having 1 to 20 carbon atoms; $X^{73}$ is hydrogen atom, fluorine atom, a hydrocarbon group having 1 to 20 carbon atoms or a perfluoroalkyl group having 1 to 20 carbon atoms; when $X^{72}$ is OH group, $X^{73}$ is not fluorine atom, and the fluorine-containing cyclopentene having OH group can impart recurring units of monocyclic structure to the polymer.

This novel monocyclic monomer is high in copolymerizability with a fluoroolefin as mentioned above, and therefore, OH group can be introduced easily to the polymer and solubility in a developing solution and other functions (for example, transparency in a vacuum ultraviolet region) can be imparted to the polymer. Also since a monocyclic structural unit can be introduced in the polymer trunk chain, a glass transition temperature can be increased and therefore the polymer is preferred from the viewpoint of dry etching resistance.

In the above-mentioned formula (70), it is particularly preferable that both of $X^{70}$ and $X^{71}$ are fluorine atoms or perfluoroalkyl groups having 1 to 20 carbon atoms and further it is preferable that $X^{72}$ is OH group and $X^{73}$ is a perfluoroalkyl group having 1 to 20 carbon atoms, since excellent solubility in a developing solution and transparency can be imparted to the polymer.

Examples of the novel fluorine-containing cyclopentene having OH group of the present invention are, for instance,

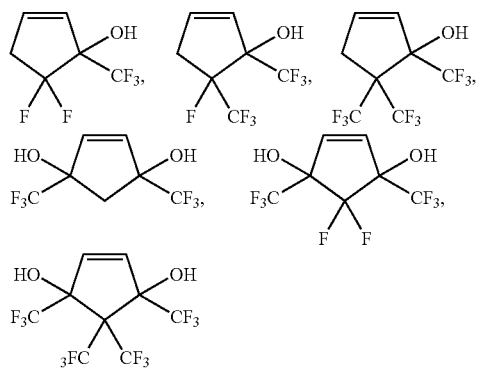

and the like as mentioned above.

Those monomers which are novel cyclopentene derivatives can be synthesized by the processes of the preparation schemes (1) to (4) mentioned supra.

Those monomers can be polymerized alone using a radical polymerization initiator or a cation polymerization initiator, and further can be subjected to radical polymerization with the above-mentioned various fluoroolefins (monomers providing the structural unit M1), acrylic monomers and α-olefins, thereby being capable of imparting hydrophilic property, solubility in a developing solution, transparency and other various functions to the polymer.

EXAMPLE

The present invention is then explained by means of examples but is not limited to them.

In the following Examples, equipment and measuring conditions used for evaluation of physical properties are as follows.

(1) NMR: NMR analyzer is AC-300 available from BRUKER CO., LTD. Measuring conditions of $^1$H-NMR: 300 MHz (tetramethylsilane=0 ppm) Measuring conditions of $^{19}$F-NMR: 280 MHz (trichlorofluoromethane=0 ppm) Measuring conditions of $^{13}$C-NMR: 75 MHz (tetramethylsilane=0 ppm)

(2) IR analysis: Measuring is carried out at room temperature with a Fourier-transform infrared spectrophotometer 1760X available from Perkin Elmer Co., Ltd.

(3) GPC: A number average molecular weight is calculated from data measured by gel permeation chromatography (GPC) by using GPC HLC-8020 available from Toso Kabushiki Kaisha and columns available from Shodex Co., Ltd. (one GPC KF-801, one GPC KF-802 and two GPC KF-806M were connected in series) and flowing tetrahydrofuran (THF) as a solvent at a flowing rate of 1 ml/minute.

Example 1

Synthesis of copolymer comprising cyclopentene and tetrafluoroethylene

A 100 ml autoclave was charged with 3.4 g of cyclopentene:

40 ml of HCFC-141b and 0.3 g of bis(4-tert-butylcyclohexyl)peroxydicarbonate (TCP), and the inside of a system was sufficiently replaced with nitrogen gas while cooling with dry ice/methanol solution. Then 10.0 g of tetrafluoroethylene (TFE) was introduced through a valve, followed by shaking for reaction at 40° C. for 18 hours. With the advance of the reaction, a gauge pressure was decreased from 0.78 MPaG (8.0 kgf/cm$^2$G) before the reaction to 0.75 MPaG (7.7 kgf/cm$^2$G).

After releasing the un-reacted monomer, the polymerization solution was removed, followed by re-precipitation with hexane to separate a copolymer. Until a constant weight was reached, vacuum drying was continued and 1.5 g of a copolymer was obtained. As a result of $^1$H-NMR and $^{19}$F-NMR analyses, the copolymer was one represented by the following formula.

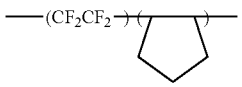

The copolymer was one comprising TFE/cyclopentene in a percent by mole ratio of 50/50 according to an elementary analysis. According to GPC analysis, a number average molecular weight of the copolymer was 5,700.

Example 2

Synthesis of copolymer comprising 2,3-dihydrofuran and tetrafluoroethylene

Reaction was carried out in the same manner as in Example 1 except that 3.5 g of 2,3-dihydrofuran:

was used instead of cyclopentene.

With the advance of the reaction, a gauge pressure was decreased from 0.78 MPaG (8.0 kgf/cm$^2$G) before the reaction to 0.75 MPaG (7.7 kgf/cm$^2$G).

After releasing the un-reacted monomer, a polymer was separated in the same manner as in Example 1 and 2.1 g of a copolymer was obtained. As a result of $^1$H-NMR and $^{19}$F-NMR analyses, the copolymer was one represented by the following formula.

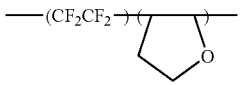

The copolymer was one comprising TFE/2,3-dihydrofuran in a percent by mole ratio of 50/50 according to an elementary analysis. According to GPC analysis, a number average molecular weight of the copolymer was 17,000.

Example 3

Synthesis of copolymer comprising cyclooctene and tetrafluoroethylene

A 100 ml autoclave was charged with 2.8 g of cyclooctene:

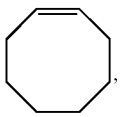

40 ml of HCFC-141b and 0.4 g of bis(4-tert-butylcyclohexyl)peroxydicarbonate (TCP), and the inside of a system was sufficiently replaced with nitrogen gas while cooling with dry ice/methanol solution. Then 10.0 g of tetrafluoroethylene (TFE) was introduced through a valve, followed by shaking for reaction at 40° C. for 18 hours. With the advance of the reaction, a gauge pressure was decreased from 0.88 MPaG (9.0 kgf/cm$^2$G) before the reaction to 0.84 MPaG (8.6 kgf/cm$^2$G).

After releasing the un-reacted monomer, the polymerization solution was removed, followed by re-precipitation with methanol to separate a copolymer. Until a constant weight was reached, vacuum drying was continued and 2.7 g of a copolymer was obtained. As a result of $^1$H-NMR analysis, the copolymer was one represented by the following formula.

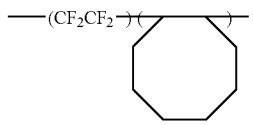

The copolymer was one comprising TFE/cyclooctene in a percent by mole ratio of 52/48 according to an elementary analysis. According to GPC analysis, a number average molecular weight of the copolymer was 9,900.

Example 4

Synthesis of copolymer comprising 3,3'-dimethylcyclopropene and tetrafluoroethylene A 300 ml autoclave was charged with 4.0 g of 3,3'-dimethylcyclopropene:

140 ml of HCFC-141b and 0.8 g of bis(4-tert-butylcyclohexyl)peroxydicarbonate (TCP), and the inside of a system was sufficiently replaced with nitrogen gas while cooling with dry ice/methanol solution. Then 23.5 g of tetrafluoroethylene (TFE) was introduced through a valve, followed by shaking for reaction at 40° C. for 18 hours. With the advance of the reaction, a gauge pressure was decreased from 0.80 MPaG (8.2 kgf/cm$^2$G) before the reaction to 0.65 MPaG (6.6 kgf/cm$^2$G).

After releasing the un-reacted monomer, the polymerization solution was removed, followed by re-precipitation with methanol to separate a copolymer. Until a constant weight was reached, vacuum drying was continued and 1.7 g of a copolymer was obtained. As a result of $^1$H-NMR analysis, the copolymer was one represented by the following formula.

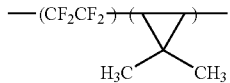

The copolymer was one comprising TFE/3,3'-dimethylcyclopropene in a percent by mole ratio of 61/39 according to an elementary analysis.

Example 5

Synthesis of copolymer comprising dicyclopentene and tetrafluoroethylene

A 100 ml autoclave was charged with 3.4 g of dicyclopentene:

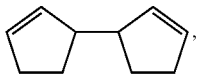

40 ml of HCFC-141b and 0.4 g of bis(4-tert-butylcyclohexyl)peroxydicarbonate (TCP), and the inside of a system was sufficiently replaced with nitrogen gas while cooling with dry ice/methanol solution. Then 10.0 g of tetrafluoroethylene (TFE) was introduced through a valve, followed by shaking for reaction at 40° C. for 18 hours. With the advance of the reaction, a gauge pressure was decreased from 0.90 MPaG (9.2 kgf/cm$^2$G) before the reaction to 0.88 MPaG (9.0 kgf/cm$^2$G).

After releasing the un-reacted monomer, the polymerization solution was removed, followed by re-precipitation with methanol to separate a copolymer. Until a constant weight was reached, vacuum drying was continued and 1.0 g of a copolymer was obtained.

As a result of $^1$H-NMR analysis, the copolymer was one having the following structure. Also according to IR analysis, an absorption of carbon-carbon double bond was recognized.

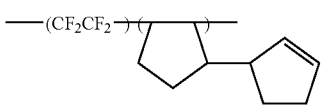

The copolymer was one comprising TFE/dicyclopentene in a percent by mole ratio of 51/49 according to an elementary analysis. Also according to IR analysis, an absorption of carbon-carbon double bond was recognized. According to GPC analysis, a number average molecular weight of the copolymer was 3,800.

Example 6

Synthesis of copolymer comprising 2,3-dihydrofuran, tetrafluoroethylene and tert-butyl-αfluoroacrylate A 500 ml autoclave was charged with 7.0 g of 2,3-dihydrofuran, 5.8 g of tert-butyl-αfluoroacrylate, 40 ml of HCFC-141b and 0.8 g of bis(4-tert-butylcyclohexyl)peroxydicarbonate (TCP), and the inside of a system was sufficiently replaced with nitrogen gas while cooling with dry ice/methanol solution. Then 40.0 g of tetrafluoroethylene (TFE) was introduced through a valve, followed by shaking for reaction at 40° C. for 18 hours. With the advance of the reaction, a gauge pressure was decreased from 0.88 MPaG (9.0 kgf/cm$^2$G) before the reaction to 0.86 MPaG (8.8 kgf/cm$^2$G).

After releasing the un-reacted monomer, the polymerization solution was removed, followed by re-precipitation with hexane to separate a copolymer. Until a constant weight was reached, vacuum drying was continued and 11.2 g of a copolymer was obtained.

As a result of $^1$H-NMR and $^{19}$F-NMR analyses, the copolymer was one comprising TFE/2,3-dihydrofuran/tert-butyl-αfluoroacrylate in a percent by mole ratio of 23/33/44. According to GPC analysis, a number average molecular weight of the copolymer was 18,000.

Example 7

Synthesis of copolymer comprising cyclopentene, tetrafluoroethylene and tert-butyl-αfluoroacrylate A 100 ml autoclave was charged with 3.4 g of cyclopentene, 1.5 g of tert-butyl-αfluoroacrylate, 40 ml of HCFC-141b and 0.3 g of bis(4-tert-butylcyclohexyl)peroxydicarbonate (TCP), and the inside of a system was sufficiently replaced with nitrogen gas while cooling with dry ice/methanol solution. Then 10.0 g of tetrafluoroethylene (TFE) was introduced through a valve, followed by shaking for reaction at 40° C. for 18 hours. With the advance of the reaction, a gauge pressure was decreased from 0.78 MPaG (8.0 kgf/cm$^2$G) before the reaction to 0.77 MPaG (7.9 kgf/cm$^2$G).

After releasing the un-reacted monomer, the polymerization solution was removed, followed by re-precipitation with hexane to separate a copolymer. Until a constant weight was reached, vacuum drying was continued and 2.2 g of a copolymer was obtained.

As a result of $^1$H-NMR and $^{19}$F-NMR analyses, the copolymer was one comprising TFE/cyclopentene/tert-butyl-αfluoroacrylate in a percent by mole ratio of 15.1/39.3/45.6. According to GPC analysis, a number average molecular weight of the copolymer was 12,000.

Example 8

Synthesis of copolymer comprising cyclopentene, tetrafluoroethylene and tert-butyl-αfluoroacrylate Reaction was carried out in the same manner as in Example 7 except that 1.7 g of cyclopentene and 1.5 g of tert-butyl-αfluoroacrylate were used. With the advance of the reaction, a gauge pressure was decreased from 0.78 MPaG (8.0 kgf/cm$^2$G) before the reaction to 0.74 MPaG (7.6 kgf/cm$^2$G).

After releasing the un-reacted monomer, a polymer was isolated in the same manner as in Example 7 and 1.7 g of a copolymer was obtained.

As a result of $^1$H-NMR and $^{19}$F-NMR analyses, the copolymer was one comprising TFE/cyclopentene/tert-butyl-αfluoroacrylate in a percent by mole ratio of 26.7/34.1/39.2. According to GPC analysis, a number average molecular weight of the copolymer was 14,000.

Example 9

Synthesis of copolymer comprising cyclopentene, tetrafluoroethylene and tert-butyl-αfluoroacrylate Reaction was carried out in the same manner as in Example 7 except that 3.4 g of cyclopentene and 4.5 g of tert-butyl-αfluoroacrylate were used. With the advance of the reaction, a gauge pressure was decreased from 0.78 MPaG (8.0 kgf/cm$^2$G) before the reaction to 0.75 MPaG (7.7 kgf/cm$^2$G).

After releasing the un-reacted monomer, a polymer was isolated in the same manner as in Example 7 and 3.5 g of a copolymer was obtained.

As a result of ¹H-NMR and ¹⁹F-NMR analyses, the copolymer was one comprising TFE/cyclopentene/tert-butyl-αfluoroacrylate in a percent by mole ratio of 6.6/51.9/41.5. According to GPC analysis, a number average molecular weight of the copolymer was 21,000.

Example 10

Synthesis of copolymer comprising 2-cyclopentene-1-tert-butylacetate and tetrafluoroethylene A 100 ml autoclave was charged with 4.6 g of 2-cyclopentene-1-tert-butylacetate:

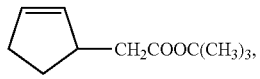

40 ml of HCFC-141b and 0.5 g of bis(4-tert-butylcyclohexyl)peroxydicarbonate (TCP), and the inside of a system was sufficiently replaced with nitrogen gas while cooling with dry ice/methanol solution. Then 10.0 g of tetrafluoroethylene (TFE) was introduced through a valve, followed by shaking for reaction at 40° C. for 18 hours. With the advance of the reaction, a gauge pressure was decreased from 0.98 MPaG (10.0 kgf/cm²G) before the reaction to 0.96 MPaG (9.8 kgf/cm²G).

After releasing the un-reacted monomer, the polymerization solution was removed, followed by re-precipitation with hexane to separate a copolymer. Until a constant weight was reached, vacuum drying was continued and 1.0 g of a copolymer was obtained. As a result of ¹H-NMR analysis, the copolymer was one represented by the following formula.

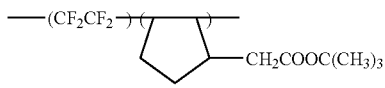

The copolymer was one comprising TFE/2-cyclopentene-1-tert-butylacetate in a percent by mole ratio of 50/50 according to an elementary analysis. According to GPC analysis, a number average molecular weight of the copolymer was 1,800.

Example 11

Synthesis of copolymer comprising diallylmalonate ethyl ester and tetrafluoroethylene A 100 ml autoclave was charged with 9.6 g of diallylmalonate ethyl ester:

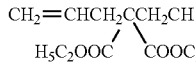

40 ml of HCFC-225 and 0.18 g of bis(4-tert-butylcyclohexyl)peroxydicarbonate (TCP), and the inside of a system was sufficiently replaced with nitrogen gas while cooling with dry ice/methanol solution. Then 8.0 g of tetrafluoroethylene (TFE) was introduced through a valve, followed by shaking for reaction at 40° C. for 20 hours. With the advance of the reaction, a gauge pressure was decreased from 0.78 MPaG (8.0 kgf/cm²G) before the reaction to 0.64 MPaG (6.5 kgf/cm²G).

After releasing the un-reacted monomer, the polymerization solution was removed, followed by concentration and re-precipitation with hexane to separate a copolymer. Until a constant weight was reached, vacuum drying was continued and 12.0 g of a copolymer was obtained.

As a result of an elementary analysis, the copolymer was one comprising TFE/diallylmalonate ethyl ester in a percent by mole ratio of 52/48. According to GPC analysis, a number average molecular weight of the copolymer was 11,000.

As a result of IR and ¹H-NMR analyses, disappearing of a peak of C=C double bond which could be recognized in a diallylmalonate ethyl ester monomer was confirmed. Also according to ¹³C-NMR and DEPT analyses, it was confirmed that the diallylmalonate ethyl ester unit in the copolymer was a 5-membered ring represented by the following formula.

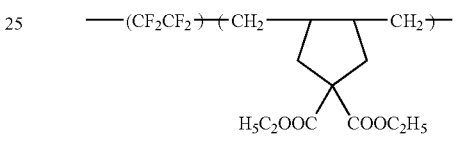

This copolymer was dissolved uniformly in the solvents such as acetone, THF, DMF and HFC-225.

Example 12

Synthesis of cyclopentene having —C(CF₃)₂OH group

A 500 ml four-necked glass flask equipped with a blowing tube was charged with 100 g of cyclopentadiene, followed by stirring in nitrogen gas atmosphere while cooling in dry ice/acetone bath. HCl gas was slowly introduced at a solution temperature of not more than 0° C. through a gas feeding tube and sometimes the flask was separated to measure the weight thereof. HCl gas was introduced up to 90% of theoretical amount to synthesize 3-chlorocyclopentene which was not isolated and used for the following reaction.

Magnesium was put in an amount of 24 g into a 1-liter four-necked glass flask equipped with a blowing tube, dry ice condenser and dropping funnel and was dried by heating in vacuo. Thereto was added 200 ml of THF, followed by cooling in ice bath. A solution obtained by mixing 31 g of previously prepared 3-chlorocyclopentene to 150 ml of THF was slowly added dropwise through the dropping funnel in a state of the solution temperature being 10° to 15° C. After completion of the addition, hexafluoroacetone was introduced slowly through the gas feeding tube so that the solution temperature did not exceed 20° C. Hexafluoroacetone was introduced until generation of heat was not recognized. After completion of the introduction of hexafluoroacetone, stirring was further continued at room temperature for three hours. The reaction mixture was put in 500 ml of 1N hydrochloric acid, followed by separating an organic layer, washing with water, drying and distilling after concentration. As a result, 56.0 g of fluorine-containing alcohol represented by the formula:

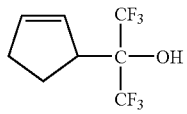

having a boiling point of from 62° to 64° C./45 mmHg was obtained. The monomer obtained above was determined by $^{19}$F-NMR, $^1$H-NMR, $^{13}$C-NMR and IR analyses.

Example 13

Synthesis of copolymer comprising tetrafluoroethylene and cyclopentene having —C(CF$_3$)$_2$OH group A 100 ml autoclave was charged with 5.5 g of the cyclopentene having —C(CF$_3$)$_2$OH group obtained in Example 12, 40 ml of HCFC-141b and 0.7 g of bis(4-tert-butylcyclohexyl)peroxydicarbonate (TCP), and the inside of a system was sufficiently replaced with nitrogen gas while cooling with dry ice/methanol solution. Then10.0 g of tetrafluoroethylene (TFE) was introduced through a valve, followed by shaking for reaction at 40° C. for 18 hours. With the advance of the reaction, a gauge pressure was decreased from 0.88 MPaG (9.0 kgf/cm$^2$G) before the reaction to 0.85 MPaG (8.7 kgf/cm$^2$G).

After releasing the un-reacted monomer, the polymerization solution was removed, followed by re-precipitation with hexane to separate a copolymer. Until a constant weight was reached, vacuum drying was continued and 1.2 g of a copolymer having a structure represented by the following formula was obtained.

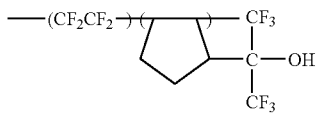

As a result of $^1$H-NMR and $^{19}$F-NMR analyses, the copolymer was one comprising TFE/cyclopentene having —C(CF$_3$)$_2$OH group in a percent by mole ratio of 50/50.

Example 14

Measurement of transparency at a wavelength of 157 nm (1) Preparation of Coating Composition The fluorine-containing polymers prepared in Examples 1 to 3, 6 to 10 and 13 were dissolved in butyl acetate so that the concentration thereof became 3%, respectively. Thus coating compositions were prepared.

(2) Coating (i) Coating on a substrate (MgF$_2$) for measuring transparency

Each coating composition was applied on a MgF$_2$ substrate at room temperature with a spin coater under the condition of 1,000 rpm. After the coating, the coating composition was baked at 100° C. for 15 minutes to form transparent coating films.

(ii) Measurement of coating thickness

Coating films were formed by applying the respective coating compositions under the same conditions as above except that a silicon wafer was used instead of the MgF$_2$ substrate.

The coating thickness was measured with a AFM device (SPI3800 available from SEIKO DENSHI KABUSHIKI KAISHA). The results are shown in Table 1.

(3) Measurement of Transparency in Vacuum Ultraviolet Region (i) Measuring device Setani-Namioka type spectrometer (BL-7B available from HIGH ENERGY KENKYU KIKO)

Slit: 7/8-7/8

Detector: PMT

Grating (GII: Blaze wavelength 160 nm, 1,200 gratings/mm)

For an optical system, refer to Rev. Sic. Instrum., 60(7), 1917 (1989) by H. Namba, et al.

(ii) Measurement of transmitting spectrum

A transmitting spectrum at a wavelength of 200 to 100 nm in a coating film formed by applying each coating composition on the MgF$_2$ substrate by the method of (2)(i) was measured using the above-mentioned device.

A molecular absorption coefficient was calculated from the transmittance at 157 nm and the coating thickness and is shown in Table 1.

Example 15

Evaluation of dry etching resistance

10% butyl acetate solutions of fluorine-containing polymers prepared in Examples 1 to 3, 6 to 10 and 13 were prepared and coated on a Si substrate with a spin coater so that the coating thickness became 200 nm. After the coating film was pre-baked at 120° C. for 2 minutes, the coating thickness was measured with an interference coating thickness meter. Then the coated substrate was put in a chamber of ICP (inductively-coupled plasma) etching equipment to carry out etching. A pressure of etching gas (Ar/N$_2$/C$_4$F$_8$ mixed gas) was 1.33 Pa (10 mTorr). Plasma etching was carried out at 13.56 MHz and 900 W for an upper electrode and at 400 kHz and 100 W for a lower electrode. An etching time was 60 seconds.

The coating thickness after the etching was measured with an interference coating thickness meter and an etching rate was calculated. For comparison, an etching rate was obtained similarly using a resist (TArF-6a-63 available from Tokyo Oka Kabushiki Kaisha) used for lithography for ArF laser. The etching rate is represented in comparison with the rate obtained for comparison. Namely, each etching rate is shown by a ratio to the etching rate of comparative polymer (the above-mentioned resist for ArF laser) provided that the latter etching rate is 1. The results are shown in Table 1.

Example 16

Evaluation of solubility in developing solution (1) Deprotection Reaction of Protective Group Each protective group contained in the fluorine-containing polymers of Examples 6 to 10 and 13 was subjected todeprotection by reacting the fluorine-containing polymers with trifluoroacetic acid by using dichloromethane solvent.

It was confirmed by ¹H-NMR and IR analyses that 85% or more of protective groups were deprotected and converted to COOH group.

(2) Coating

10% butyl acetate solutions of fluorine-containing polymers prepared in Examples 6 to 10 and 13 and deprotected fluorine-containing polymers obtained above were prepared and coated on a Si substrate with a spin coater so that a coating thickness became 200 nm, followed by drying.

(3) Determination of Solubility

The Si substrate after the drying was dipped in a 2.38% aqueous solution of tetramethylammonium hydroxide for 60 seconds. Then the substrate was removed and dried at room temperature, and whether or not there was a remaining film was checked with naked eyes.

When there remain no film, solubility is assumed to be ○. The results are shown in Table 1

Example 17

(1) Preparation of Coating Composition

The fluorine-containing polymers prepared in Examples 6 to 10 and 13 and a photoacid generator (B) in an amount of 5% by weight based on the polymer were dissolved in butyl acetate as the solvent (C) and a concentration of the polymer was diluted to 5% by weight.

As the photoacid generator, S-(trifluoromethyl)-dibenzothiopheniumtrifluoromethane sulfonate:

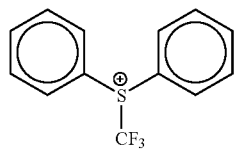

was used.

(2) Coating

Coating compositions were coated on a Si substrate with a spin coater so that a coating thickness became 200 nm, followed by drying.

(3) Measurement of Transparency in Vacuum Ultraviolet Region

Measurement was made in the same manner as in Example 14. A molecular absorption coefficient at 157 nm is shown in Table 1.

TABLE 1

| Fluorine-containing polymer | Ex. 14 Absorption coefficient at 157 nm ($\mu m^{-1}$) | Ex. 15 Etching rate (to ArF resist) | Ex. 16 Solubility in developing solution | | Ex. 17 Absorption coefficient at 157 nm ($\mu m^{-1}$) |
|---|---|---|---|---|---|
| | | | Before deprotection | After deprotection | |
| Ex. 1 | 0.9 | 0.8 | — | — | — |
| Ex. 2 | 1.0 | 0.9 | — | — | — |
| Ex. 3 | 1.1 | 0.9 | — | — | — |
| Ex. 6 | 3.5 | 1.05 | X | ○ | 3.7 |
| Ex. 7 | 3.6 | 1.2 | X | ○ | 3.9 |
| Ex. 8 | 3.7 | 1.1 | X | ○ | 3.9 |
| Ex. 9 | 4.1 | 1.5 | X | ○ | 4.4 |
| Ex. 10 | 3.2 | 0.9 | X | ○ | 3.4 |
| Ex. 13 | 0.7 | 1.0 | ○ | — | 1.0 |

Example 18

Synthesis of fluorine-containing cyclopentene derivative having OH group (1) Synthesis of $CF_3COCF_2COCF_3$ A 500 ml four-necked glass flask was charged with 31.2 g of $CF_3COCH_2COCF_3$ and 250 ml of acetonitrile, followed by replacement with nitrogen at 0° C. The mixture was cooled to −10° C. and thereto was introduced 10% by volume of $F_2/N_2$ (600 mmol as $F_2$, four times the molar quantity) over five hours. As a result, the solution temperature was increased to a temperature near 5° C. After the introduction of fluorine gas, nitrogen gas was flowed at 0° C. for 30 minutes to purge fluorine gas. Then a solution prepared by dissolving 52 g of $BF_3.NEt_3$ in 20 ml of acetonitrile was added dropwise at 0° C. After completion of the addition, stirring was further carried out at room temperature for 15 hours and the flask was heated to 50° C. in an oil bath, followed by distilling in nitrogen gas atmosphere to obtain 26.4 g of $CF_3COCF_2COCF_3$ (boiling point: 34° to 35° C.). According to ¹⁹F-NMR, ¹H-NMR, ¹³C-NMR and IR analyses, the obtained product was determined as $CF_3COCF_2COCF_3$.

(2) Synthesis of diene.diol derivative with $CH_2$=CHMgBr and $C_2H_5OCH_2Cl$

The inside of a 500 ml four-necked glass flask was replaced with nitrogen and 10.5 g of $CF_3COCF_2COCF_3$ and 50 ml of THF were introduced thereto, followed by cooling the flask in an ice bath. Then 129 ml of 1N THF solution of $CH_2$=CHMgBr was slowly added thereto dropwise so that the solution temperature did not exceed 10° C. After completion of the addition, the solution temperature was increased to room temperature over one hour and the flask was again cooled to 0° C. in an ice bath. Then 21.3 g of $C_2H_5OCH_2Cl$ and 81 ml of DMF were slowly added thereto dropwise through a dropping funnel so that the solution temperature did not exceed 10° C. After stirring at room temperature for 24 hours, the reaction solution was poured into 1 liter of water to separate an organic layer. An aqueous layer was extracted with 200 ml of hexane, and washed together with the organic layer using 200 ml of 1N HCl two times and 200 ml of saturated brine once, followed by drying with potassium carbonate, concentrating with an evaporator and separating and collecting a concentrated residue with a silica gel column (a developing solvent was ethyl acetate:hexane=1:15, Rf value was 0.2). The obtained fraction was concentrated with an evaporator and 15.2 g of diene-diol derivative represented by the formula:

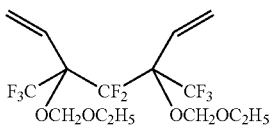

was obtained. The above-mentioned structure was determined according to $^{19}$F-NMR, $^1$H-NMR, $^{13}$C-NMR and IR analyses.

(3) Synthesis of Cyclopentene-diol Derivative by Metathesis Ring-Closing Reaction In 50-liter two-necked flask was put 0.8 g of PhCH=RuCl$_2$(PCy$_3$)$_2$ (Cy represents cyclohexyl), followed by replacement with nitrogen. Then thereto were added 2 liter of CH$_2$Cl$_2$ subjected to drying and deaeration and 8.32 g of diene-diol derivative prepared above. Stirring was continued at room temperature for 24 hours, followed by concentrating and separating and collecting with a silica gel column (a developing solvent was ethyl acetate:hexane=1:20, Rf value was 0.25). The obtained fraction was concentrated with an evaporator and 6.21 g of cyclopentene-diol derivative represented by the formula:

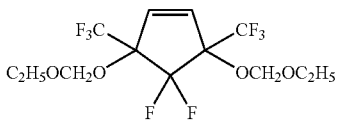

was obtained. The above-mentioned structure was determined according to $^{19}$F-NMR, $^1$H-NMR, $^{13}$C-NMR and IR analyses.

(4) Deprotection of cyclopentene-diol derivative

In a four-necked flask equipped with a refluxing tube were put 15 g of cyclopentene-diol derivative obtained above, 40 ml of dichloromethane, 4 g of trifluoroacetic acid and 1 g of water, followed by refluxing at 40° C. for 12 hours. The separation of solution and distillation were carried out and 8.5 g of fluorine-containing cyclopentene-diol represented by the formula:

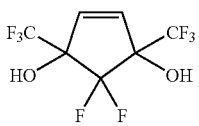

was obtained. The above-mentioned structure was determined according to 19F-NMR, $^1$H-NMR, $^{13}$C-NMR and IR analyses.

Experimental Example 1

Relation between pKa Value and ΔH of Fluorine-Containing Ethylenic Monomer Having OH Group (1) Calculation of ΔH of Fluorine-Containing Ethylenic Monomers Having OH Group With respect to various fluorine-containing ethylenic monomers having OH group shown in Table 2, calculation of molecular orbital was carried out by the above-mentioned MOPAC97, AM1 method to calculate a produced enthalpy H(M-OH) before acid dissociation and a produced enthalpy H(M-O$^-$) after acid dissociation. With respect to the monomers having a long chain, calculation of molecular orbital was carried out using the model structures shown in Table 2. Then provided that a produced enthalpy of hydrogen ion is a constant of 200 kJ/mol, each produced enthalpy was substituted in the following Equation 3:

$$\Delta H = H(M-O^-) + 200 - H(M-OH) \quad \text{(Equation 3)}$$

to obtain ΔH (kJ/mol). The results are shown in Table 2.

(2) (Measurement of pKa Value of Various Fluorine-Containing Compounds Having OH Group)

Measurement of pKa value of cyclopentene derivative having —C(CF$_3$)$_2$OH group

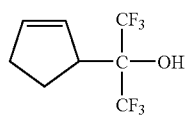

In a water/acetone mixture (10/15 ml) solution was put 0.4045 g of the above-mentioned cyclopentene derivative, followed by stirring at room temperature. After it was confirmed that the solution became homogeneous, titration was carried out with about 0.2 mol/liter NaOH solution. A titration curve was obtained by adding a NaOH solution dropwise in increments of 0.15 ml and recording a pH value at every addition. An equivalence point was determined by an inflection point (maximum differential value of titration curve=dpH/dml) of the titration curve. In this case, the equivalence point was 8.0 ml. A pH value at 4.0 ml which was a half of the equivalence point was read from the titration curve and was found to be 11.12. From a titration curve of water/acetone solution and aqueous solution which had been measured previously as a blank solution, a difference in a pH value derived from an electric potential difference between the solutions at titration of 4.0 ml was 1.50. Therefore from 11.12−1.50=9.62, a pKa value of this norbornene derivative was determined as 9.62.

In the case of titration of 0.8104 g of cyclopentene derivative by the same procedures as above, an equivalence point was 16.4 ml and a half of equivalence point was 8.4 ml. A pH value at a half of the equivalence point was 11.14.

A difference in a pH value between the both solutions at 8.4 ml was 1.19, and from 11.14−1.19=9.95, a pKa value of the cyclopentene derivative was determined as 9.95.

In the case of titration of 0.9812 g of cyclopentene derivative by the same procedures as above, an equivalence point thereof was 18.95 ml and a half of equivalence point was 9.48 ml. A pH value at this time was 11.03. A difference in a pH value between the both solutions at 9.48 ml was 1.17, and from 11.03−1.17=9.86, a pKa value of the cyclopentene derivative was determined as 9.86.

in which calculated ΔH and actually measured pKa are plotted in an abscissa and an ordinate, respectively. As shown in FIG. 1, it was found that a good proportional relation is exhibited.

From the graph, an equation:

$$(pKa) = 0.0442 \cdot \Delta H + 6.8613 \qquad \text{(Equation 4)}$$

($R^2 = 0.9224$) was Obtained.

TABLE 2

| Fluorine-containing compound having OH group | Model structure | (1) ΔH | (2) pKa |
|---|---|---|---|
| cyclopentenyl–C(CF$_3$)$_2$OH | cyclopentyl H,H –C(CF$_3$)$_2$OH | 60.5 | 9.8 |
| norbornenyl–C(CF$_3$)$_2$OH | norbornyl H,H –C(CF$_3$)$_2$OH | 59.5 | 10.2 |
| F-substituted norbornenyl–C(CF$_3$)$_2$OH | F-substituted norbornyl H,H –C(CF$_3$)$_2$OH | 40.4 | 9.0 |
| tri-F-substituted norbornenyl–C(CF$_3$)$_2$OH | tri-F-substituted norbornyl H,H –C(CF$_3$)$_2$OH | 29.9 | 8.3 |
| F-substituted norbornenyl–CF$_3$, OH | F-substituted norbornyl H,H –CF$_3$, OH | 116.3 | 11.5 |
| CH$_2$=CHCH$_2$C(CF$_3$)$_2$OH | CH$_2$=CHCH$_2$C(CF$_3$)$_2$OH | 74.2 | 9.6 |
| CF$_2$=CF—C(CF$_3$)$_2$OH | CH$_2$=CHCH$_2$C(CF$_3$)$_2$OH | 13.2 | 7.1 |
| CF$_3$CH(CF$_3$)—OH | CH$_2$=CHCH$_2$C(CF$_3$)$_2$OH | 50.4 | 9.3 |
| CH$_2$=CF—C(CF$_3$)$_2$OH | CH$_2$=CHCH$_2$C(CF$_3$)$_2$OH | 38.7 | 8.0 |
| CH$_2$=CFCF$_2$OCFCF$_2$OCFCH$_2$OH (with CF$_3$, CF$_3$ branches) | HCF$_2$OCFCH$_2$OH (with CF$_3$ branch) | 122.3 | 12.6 |

From those experiments carried out three times, a pKa value of the cyclopentene derivative was determined as 9.8.

With respect to the various fluorine-containing compounds having OH group shown in Table 2, a pKa value was measured by the same procedures as above. The results are shown in Table 2.

(3) Relation between ΔH and Actually Measured pKa

With respect to the various fluorine-containing compounds having OH group shown in Table 2, FIG. 1 is a graph The novel fluorine-containing polymer of the present invention possesses dry etching resistance higher than that of polymers prepared using norbornene and transparency thereof even in a vacuum ultraviolet region is excellent as compared with polymers prepared using norbornene.

Also the copolymer obtained by copolymerizing a fluoroolefin with the novel unsaturated compound having a monocyclic structure of the present invention which has an acid-reactive functional group directly bonded to a ring and partly contains fluorine possesses an excellent dry etching resistance and high transparency when used for a resist.

The invention claimed is:

1. A fluorine-containing polymer having an aliphatic monocyclic structure in the polymer trunk chain which has a number average molecular weight of from 500 to 1,000,000 and is represented by the formula (Mb):

-(M1)-(M2b)-(N)—   (Mb)

in which
the structural unit M1 is a structural unit derived from an ethylenic monomer having 2 or 3 carbon atoms and at least one fluorine atom, the structural unit M2b is at least one structural unit which introduces an aliphatic monocyclic structure in the polymer trunk chain and is represented by the formula (b):

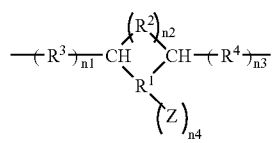
(b)

wherein $R^1$ is at least one hydrocarbon group selected from the group consisting of a divalent hydrocarbon group which has 1 to 8 carbon atoms and constitutes a ring (which may be further substituted with a hydrocarbon group or a fluorine-containing alkyl group) and a divalent hydrocarbon group having ether bond which has the sum of carbon atoms and oxygen atoms of 2 to 8 and constitutes a ring (which may be further substituted with a hydrocarbon group or a fluorine-containing alkyl group); $R^2$ is an alkylene group which has 1 to 3 carbon atoms and constitutes a ring; $R^3$ and $R^4$ are the same or different and each is a divalent alkylene group having 1 or 2 carbon atoms; n1, n2 and n3 are the same or different and each is 0 or 1; Z are the same or different and each is:

wherein $Z^1$ is at least one functional group selected from the group consisting of OH group, COOH group, a derivative of carboxylic acid group and a functional group protected by a protective group which can convert the functional group to OH group by reaction with an acid; $R^5$ is a divalent organic group; n5 is 0 or 1; n4 is an integer of from 1 to 3, the structural unit N is a structural unit derived from a monomer copolymerizable with the monomers to introduce the structural units M1 and M2a, and
the structural units M1, M2b and N are contained in amounts of from 1 to 99% by mole, from 1 to 99% by mole and from 0 to 98% by mole, respectively.

2. The fluorine-containing polymer of claim 1, wherein the structural unit M2b is a structural unit represented by the formula (b-1):

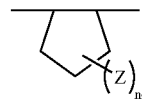
(b-1)

wherein Z and n4 are as defined in the formula (b).

3. The fluorine-containing polymer of claim 1, wherein the structural unit M2b is a structural unit represented by the formula (b-2):

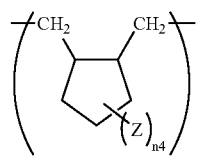
(b-2)

wherein Z and n4 are as defined in the formula (b).

4. The fluorine-containing polymer of claim 1, wherein in the formula (b) representing the structural unit M2b, $R^5$ in Z is a divalent alkylene group having 1 to 30 carbon atoms or a fluorine-containing alkylene group which has 1 to 30 carbon atoms and may have ether bond.

5. The fluorine-containing polymer of claim 1, wherein in the formula (b) representing the structural unit M2b, Z is represented by the formula:

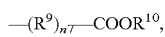

wherein $R^9$ is an alkylene group which has 1 to 10 carbon atoms and may have ether bond or a fluorine-containing alkylene group which has 1 to 10 carbon atoms and may have ether bond; $R^{10}$ is hydrogen atom or an alkyl group having 1 to 10 carbon atoms; n7 is 0 or 1.

6. The fluorine-containing polymer of claim 1, wherein in the formula (b) representing the structural unit M2b, Z is represented by the, formula:

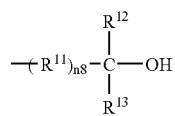

wherein $R^{11}$ is an alkylene group which has 1 to 5 carbon atoms and may have ether bond or a fluorine-containing alkylene group which has 1 to 5 carbon atoms and may have ether bond; $R^{12}$ and $R^{13}$ are the same or different and each is hydrogen atom, an alkyl group having 1 to 10 carbon atoms, an aryl group having 3 to 10 carbon atoms, a fluorine-containing alkyl group which has 1 to 10 carbon atoms and may have ether bond or an aryl group which has 3 to 10 carbon atoms and may have ether bond; n8 is 0 or 1.

7. The fluorine-containing polymer of claim 6, wherein Z is represented by the formula:

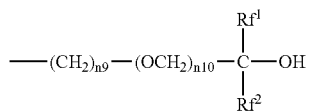

wherein $Rf^1$ is a fluorine-containing alkyl group which has 1 to 10 carbon atoms and may have ether bond; $Rf^2$ is hydrogen atom, an alkyl group having 1 to 10 carbon atoms, an aryl group having 3 to 10 carbon atoms or a fluorine-containing alkyl group which has 1 to 10 carbon atoms and may have ether bond; n9 is 0 or an integer of from 1 to 5; n10 is 0 or 1.

8. The fluorine-containing polymer of claim 7, wherein $Rf^1$ and $Rf^2$ are the same or different and each is a perfluoroalkyl group having 1 to 5 carbon atoms.

9. The fluorine-containing polymer of claim 1, wherein the structural unit M1 is a structural unit derived from tetrafluoroethylene or chlorotrifluoroethylene.

* * * * *